US010478428B2

(12) United States Patent
Blanchette et al.

(10) Patent No.: US 10,478,428 B2
(45) Date of Patent: *Nov. 19, 2019

(54) COMBINATION THERAPY FOR CANCER TREATMENT

(71) Applicant: Ipsen Biopharm Ltd., Wrexham (GB)

(72) Inventors: Sarah F. Blanchette, Lynnfield, MA (US); Daryl C. Drummond, Lincoln, MA (US); Jonathan Basil Fitzgerald, Arlington, MA (US); Victor Moyo, Ringoes, NJ (US)

(73) Assignee: Ipsen Biopharm Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/852,551

(22) Filed: Dec. 22, 2017

(65) Prior Publication Data

US 2018/0117034 A1 May 3, 2018

Related U.S. Application Data

(63) Continuation of application No. 15/337,274, filed on Oct. 28, 2016, now Pat. No. 9,895,365, which is a (Continued)

(51) Int. Cl.
*A61K 31/4745* (2006.01)
*A61K 31/436* (2006.01)

(Continued)

(52) U.S. Cl.
CPC ........ *A61K 31/4745* (2013.01); *A61K 9/0019* (2013.01); *A61K 9/127* (2013.01);

(Continued)

(58) Field of Classification Search
CPC ................................................. A61K 31/4745
See application file for complete search history.

(56) References Cited

U.S. PATENT DOCUMENTS 4,604,463 A 8/1986 Miyasaka et al.
5,013,556 A 5/1991 Woodle et al.

(Continued)

FOREIGN PATENT DOCUMENTS

WO 1997028156 A1 8/1997
WO 2003013536 A2 2/2003

(Continued)

OTHER PUBLICATIONS

Alagoz, M. et al., "DNA Repair and Resistance to Topoisomerase I Inhibitors: Mechanisms, Biomarkers and Therapeutic Targets", Current Medicinal Chemistry, 2012, pp. 3874-388, vol. 19.

(Continued)

*Primary Examiner* — Benjamin J Packard
(74) *Attorney, Agent, or Firm* — McNeill Baur PLLC

(57) ABSTRACT

Combination therapies for treating cancer comprising administration of a topoisomerase-1 inhibitor and a PARP inhibitor are provided. The topoisomerase-1 inhibitor can be delivered as a liposomal formulation that provides for prolonged accumulation of the topoisomerase-1 inhibitor within a tumor relative to outside of the tumor. Therapeutic benefit can thereby be obtained by delaying the administration of the PARP inhibitor after each administration of a liposomal irinotecan formulation until the accumulation of the topoisomerase inhibitor in the tumor is sufficiently greater than outside the tumor to result in increased efficacy of the PARP inhibitor and topoisomerase inhibitor within the tumor, while reducing the peripheral toxicity of the combination therapy. The therapies disclosed herein are useful in the treatment of human cancers with solid tumors, including cervical cancer.

17 Claims, 30 Drawing Sheets

ME-180 cells viability (1000cells/well in 384-well plate) treated with SN-38 and with different PARP inhibitors (0.33 ug/ml) for 24hrs, washed and incubated for additional 72hrs with fresh media MS-751 cells viability (1000cells/well in 384-well plate) treated with SN-38 and with different PARP inhibitors (0.33 ug/ml) for 24hrs, washed and incubated for additional 72hrs with fresh media

Related U.S. Application Data continuation of application No. PCT/US2016/047827, filed on Aug. 19, 2016.

(60) Provisional application No. 62/323,422, filed on Apr. 15, 2016, provisional application No. 62/308,924, filed on Mar. 16, 2016, provisional application No. 62/269,511, filed on Dec. 18, 2015, provisional application No. 62/269,756, filed on Dec. 18, 2015, provisional application No. 62/207,709, filed on Aug. 20, 2015, provisional application No. 62/207,760, filed on Aug. 20, 2015.

(51) Int. Cl.

| | |
|---|---|
| ***A61K 31/04*** | (2006.01) |
| ***A61K 31/166*** | (2006.01) |
| ***A61K 31/416*** | (2006.01) |
| ***A61K 31/4184*** | (2006.01) |
| ***A61K 31/475*** | (2006.01) |
| ***A61K 31/502*** | (2006.01) |
| ***A61K 31/55*** | (2006.01) |
| ***A61K 47/06*** | (2006.01) |
| ***A61K 9/127*** | (2006.01) |
| ***A61K 9/00*** | (2006.01) |
| ***A61K 31/454*** | (2006.01) |
| ***A61K 31/5025*** | (2006.01) |
| ***A61K 45/06*** | (2006.01) |

(52) U.S. Cl.

CPC ............ *A61K 31/04* (2013.01); *A61K 31/166* (2013.01); *A61K 31/416* (2013.01); *A61K 31/4184* (2013.01); *A61K 31/436* (2013.01); *A61K 31/454* (2013.01); *A61K 31/475* (2013.01); *A61K 31/502* (2013.01); *A61K 31/5025* (2013.01); *A61K 31/55* (2013.01); *A61K 45/06* (2013.01); *A61K 47/06* (2013.01)

(56) References Cited

U.S. PATENT DOCUMENTS

| | | | |
|---|---|---|---|
| 5,077,056 | A | 12/1991 | Bally et al. |
| 5,192,549 | A | 3/1993 | Barenolz et al. |
| 5,316,771 | A | 5/1994 | Barenholz et al. |
| 5,538,954 | A | 7/1996 | Koch et al. |
| 5,593,622 | A | 1/1997 | Yoshioka et al. |
| 5,676,971 | A | 10/1997 | Yoshioka et al. |
| 5,783,568 | A | 7/1998 | Schlessinger et al. |
| 5,785,987 | A | 7/1998 | Hope et al. |
| 5,846,458 | A | 12/1998 | Yoshioka et al. |
| 6,110,491 | A | 8/2000 | Kirpotin |
| 6,210,707 | B1 | 4/2001 | Papahadjopoulos et al. |
| 6,214,388 | B1 | 4/2001 | Benz et al. |
| 6,241,999 | B1 | 6/2001 | Ye et al. |
| 6,355,268 | B1 | 3/2002 | Slater et al. |
| 6,403,569 | B1 | 6/2002 | Achterrath |
| 6,465,008 | B1 | 10/2002 | Slater et al. |
| 6,545,010 | B2 | 4/2003 | Bissery |
| 6,720,001 | B2 | 4/2004 | Chen et al. |
| 6,794,370 | B2 | 9/2004 | Achterrath |
| 7,022,336 | B2 | 4/2006 | Papahadjopoulos et al. |
| 7,060,828 | B2 | 6/2006 | Madden et al. |
| 7,135,177 | B2 | 11/2006 | Benz et al. |
| 7,219,016 | B2 | 5/2007 | Rimm et al. |
| 7,244,826 | B1 | 7/2007 | Marks et al. |
| 7,507,407 | B2 | 3/2009 | Benz et al. |
| 7,829,113 | B2 | 11/2010 | Okada et al. |
| 7,846,440 | B2 | 12/2010 | Schoeberl et al. |
| 7,846,473 | B2 | 12/2010 | Yoshino et al. |
| 7,871,620 | B2 | 1/2011 | Benz et al. |
| 7,892,554 | B2 | 2/2011 | Marks et al. |
| 8,067,432 | B2 | 11/2011 | Anderson et al. |
| 8,147,867 | B2 | 4/2012 | Hong et al. |
| 8,329,213 | B2 | 12/2012 | Hong et al. |
| 8,496,961 | B2 | 7/2013 | Hong et al. |
| 8,658,203 | B2 | 2/2014 | Drummond et al. |
| 8,703,181 | B2 | 4/2014 | Hong et al. |
| 8,992,970 | B2 | 3/2015 | Hong et al. |
| 9,339,497 | B2 | 5/2016 | Bayever et al. |
| 9,364,473 | B2 | 6/2016 | Bayever et al. |
| 9,452,162 | B2 | 9/2016 | Bayever et al. |
| 9,492,442 | B2 | 11/2016 | Bayever et al. |
| 9,717,724 | B2 | 8/2017 | Bayever et al. |
| 9,895,365 | B2 | 2/2018 | Blanchette et al. |
| 2002/0102298 | A1 | 8/2002 | Needham |
| 2002/0146450 | A1 | 10/2002 | Slater et al. |
| 2002/0192275 | A1 | 12/2002 | Zalipsky et al. |
| 2003/0138481 | A1 | 7/2003 | Zadi |
| 2004/0002505 | A1 | 1/2004 | Ozawa et al. |
| 2007/0110798 | A1 | 5/2007 | Drummond et al. |
| 2007/0265324 | A1 | 11/2007 | Wernet et al. |
| 2008/0108135 | A1 | 5/2008 | Marks et al. |
| 2009/0123419 | A1 | 5/2009 | Sherman et al. |
| 2009/0149397 | A1 | 6/2009 | Ossovskaya et al. |
| 2010/0056761 | A1 | 3/2010 | Schoeberl et al. |
| 2010/0068255 | A1 | 3/2010 | Benz et al. |
| 2011/0059076 | A1 | 3/2011 | McDonagh et al. |
| 2011/0123523 | A1 | 5/2011 | Schoeberl et al. |
| 2012/0003160 | A1 | 1/2012 | Wolf et al. |
| 2012/0045524 | A1 | 2/2012 | Wernet et al. |
| 2012/0269812 | A1 | 10/2012 | Baum et al. |
| 2013/0209481 | A1 | 8/2013 | Zhou et al. |
| 2013/0236459 | A1 | 9/2013 | Baum et al. |
| 2013/0274281 | A1 | 10/2013 | Bradley |
| 2014/0065204 | A1 | 3/2014 | Hayes et al. |
| 2014/0170075 | A1 | 6/2014 | Drummond et al. |
| 2015/0182460 | A1 | 7/2015 | Hong et al. |
| 2015/0182521 | A1 | 7/2015 | Bayever et al. |
| 2015/0328156 | A1 | 11/2015 | Bayever et al. |
| 2015/0374682 | A1 | 12/2015 | Bayever et al. |
| 2016/0030341 | A1 | 2/2016 | Hong et al. |
| 2016/0030342 | A1 | 2/2016 | Hong et al. |
| 2016/0074382 | A1 | 3/2016 | Bayever et al. |
| 2016/0206615 | A1 | 7/2016 | Tangutoori et al. |

FOREIGN PATENT DOCUMENTS

| | | | |
|---|---|---|---|
| WO | 2003030864 | A1 | 4/2003 |
| WO | 2003101474 | A1 | 12/2003 |
| WO | 2005000900 | A1 | 1/2005 |
| WO | 2005107712 | A1 | 11/2005 |
| WO | 2006110816 | A2 | 10/2006 |
| WO | 2007076117 | A2 | 7/2007 |
| WO | 2009126920 | A3 | 3/2010 |
| WO | 2011153010 | A1 | 12/2011 |
| WO | 2012012454 | A1 | 1/2012 |
| WO | 2012078695 | A2 | 6/2012 |
| WO | 2012079582 | A1 | 6/2012 |
| WO | 2012146610 | A1 | 11/2012 |
| WO | 2013006547 | A2 | 1/2013 |
| WO | 2013158803 | A1 | 10/2013 |
| WO | 2014113167 | A1 | 7/2014 |
| WO | 2016094402 | A1 | 6/2016 |
| WO | 2017031442 | A1 | 2/2017 |
| WO | 2017031445 | A1 | 2/2017 |

OTHER PUBLICATIONS

Clinical Trials Archive: "Liposomal Irinotecan and Veliparib in Treating Patients with Solid Tumors That Are Metastatic or Cannot be Removed by Surgery", NCT02631733, Updated: Dec. 15, 2015, Retrieved from the Internet: https:/clinicaltrials.gov/archive/NCT02631733/2015_12_15, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Feb. 16, 2016, Retrieved from the Internet: https://clinicaltrials.gov/archive/NCT02631733/2016_02_16, pp. 1-6.

(56) References Cited

OTHER PUBLICATIONS

Clinical Trials Archive: "Liposomal Irinotecan and Veliparib in Treating Patients With Solid Tumors That Are Metastatic or Cannot Be Removed by Surgery", NCT02631733, Updated: Jun. 20, 2016, Retrieved from the Internet: https://clinicaltrials.gov/archive/NCT02631733/2016_06_20, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Jun. 21, 2016, Retrieved from the Internet: https://clinicaltrials.gov/archive/NCT02631733/2016_06_21, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Jul. 6, 2016, Retrieved from the Internet: https://clinicaltrials.gov/archive/NCT02631733/2016_07_06, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Jul. 11, 2016, Retrieved from the Internet: https://clinicaltrials.gov/archive/NCT02631733/2016_07_11, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Jul. 19, 2016, Retrieved from the Internet: https://clinicaltrials.gov/archive/NCT02631733/2016_07_19, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Aug. 7, 2016, Retrieved from the Internet: https://clinicaltrials.gov/archive/NCT02631733/2016_08_07, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Sep. 21, 2016, Retrieved from the Internet: https://clinicaltrials.gov/archive/NCT02631733/2016_09_21, pp. 1-6.

Davidson, D. et al., "The PARP inhibitor ABT-888 synergizes irinotecan treatment of colon cancer cell lines", Invest New Drugs; DOI: 10.1007/s10637-012-9886-7; Published online: Oct. 9, 2012, 8 pages.

Douillard J. et al, "Irinotecan Combined With Fluorouracil Compared with Fluorouracil Alone as First-Line Treatment for Metastatic Colorectal Cancer: A Multicentre Randomised Trial," The Lancet, 2000, pp. 1041-1047, vol. 355, No. 9209.

Gilbert, D.C. et al., "Topoisomerase I inhibition in colorectal cancer: biomarkers and therapeutic targets", British Journal of Cancer, 2012, pp. 18-24, vol. 106, No. 1.

Hare, J. et al., "Treatment of Colorectal Cancer Using a Combination of Liposomal Irinotecan (Irinophore C(TM)) and 5-Fluorouracil," PLOS ONE, 2013, pp. 1-12, vol. 8, No. 4, E62349.

Kalra, A. V., et al. "Preclinical activity of nanoliposomal irinotencan Is governed by tumor deposition and intratumor pro-drug conversion", Cancer Research; Author Manuscript Published OnlineFirst Oct. 1, 2014, 31 pages.

Kalra, A. V., et al., "Preclinical Activity of Nanoliposomal Irinotecan Is Governed by Tumor Deposition and Intratumor Prodrug Conversion", Cancer Research; Published OnlineFirst Oct. 1, 2014, 12 pages.

Koshkaryev, A., et al., Differential Tissue Clearance Results in Improved Therapeutic Index for Nanoliposomal Irinotecan (nal-IRI; Onivyde) when Combined with the PARP inhibitor veliparib; Poster presented at AACR Meeting on Apr. 16-20, 2016, 1 page.

Lo Russo, P. M., et al., Phase I Safety, Pharmacokinetic, and Pharmacodynamic Study of the Poly(ADP-ribose) Polymerase (PARP) Inhibitor Veliparib (ABT-888) in Combination with Irinotecan in Patients with Advanced Solid Tumors; Clinical Cancer Research, 2016, pp. 3227-3237.

Lynparza™ (olaparib) capsules Prescribing Information, © AstraZeneca 2014, Revised: Dec. 2014, 6 pages.

Messerer C. L. et al., "Liposomal Irinotecan: Formulation Development and Therapeutic Assessment in Murine Xenograft Models of Colorectal Cancer," Clinical Cancer Research : An Official Journal of the American Association For Cancer Research, 2004, pp. 6638-6649, vol. 10, No. 19.

Murai, J. et al., "Rationale for Poly(ADP-ribose) Ploymerase (PARP) Inhibitors in Combination Therapy with Campothecins or Temozolomide Based on PARP Trapping versus Catalytic Inhibition", The Journal of Pharmacology and Experimental Therapeutics, 2014, pp. 408-416, vol. 349.

Murai, J. et al., "Identification of novel PARP inhibitors using a cell-based TDP1 inhibitory assay in a quantitative high-throughput screening platform" Author manuscript; Published in final edited form as: DNA Repair (Amst)., 2014, pp. 177-182, vol. 21.

PCT/US2016/047814 International Search Report, dated Nov. 17, 2016, 3 pages.

PCT/US2016/047827 International Search Report, dated Nov. 17, 2016, 3 pages.

Tahara, M. et al., "The Use of Olaparib (AZD2281) Potentiates SN-38 Cytotoxicity in Colon Cancer Cells by Indirect Inhibition of Rad51-Mediated Repair of DNA Double-Strand Breaks", Molecular Cancer Therapeutics; 13(5) May 2014, pp. 1170-1180.

Tentori, L. et al."Influence of MLH1 on colon cancer sensitivity to poly(ADP-ribose) polymerase inhibitor combined with irinotecan", Internal Journal of Oncology, 2013, pp. 210-218, vol. 43.

Williams, S. M. Genther et al., "Treatment with the PARP Inhibitor, Niraparib, Sensitizes Colorectal Cancer Cell Lines to Irinotecan Regardless of MSI/MSS Status," Cancer Cell International, 2015, pp. 1-11, vol. 15, No. 1, 14.

Zander, S. A. et al. EZN-2208 (PEG-SN38) Overcomes ABCG2-Mediated Topotecan Resistance in BRCA1-Deficient Mouse Mammary Tumors, PLOS One, Sep. 2012, pp. 1-9, vol. 7, Issue 9.

Zhang, Y. et al. "Poly(ADP-ribose) polymerase and XPF-ERCC1 participate in distinct pathways for the repair of topoisomerase I-induced DNA damage in mammalian cells", Nucleic Acids Research, 2011, pp. 3607-3620, vol. 39, No. 9.

Znojek, P. et al. "Preferential Potentiation of Topoisomerase I Poison cytotoxicity by PARP Inhibition in S Phase", British Journal of Cancer, 2014, pp. 1319-1326, vol. 111.

Kummar, S., et al. "Phase I Study of PARP Inhibitor ABT-888 in Combination with Topotecan in Adults with Refractory Solid Tumors and Lymphomas," Cancer Research, 71(17); pp. 5626-5634; 2011.

Lo Russo, P. M., et al., Phase I Study of the Safety, Pharmacokinetics (PK), and Pharmacodynamics (PD) of the Poly(ADP-ribose) Polymerase (PARP) Inhibitor Veliparib (ABT-888; V) in Combination with Irinotecan (CPT-11; Ir) in Patients (pts) with Advanced Solid Tumors; J Clin Oncol 29: 2011 (Suppl, Abstract 3000); 1 page.

Lo Russo, P. M., et al., Phase I Study of the Safety, Pharmacokinetics, and Pharmacodynamics of the Poly(ADP-ribose) Polymerase (PARP) Inhibitor Veliparib (ABT-888) in Combination with Irinotecan (CPT-11) in Patients with Advanced Solid Tumors; Presentation at American Society of Clinical Oncology 2011 Meeting; 37 pages.

U.S. Appl. No. 15/241,106: Jul. 10, 2017 Final Office Action, 16 pages.

U.S. Appl. No. 15/241,128: Nov. 25, 2016 Nonfinal Office Action, 6 pages.

U.S. Appl. No. 15/296,536: Mar. 8, 2017 Nonfinal Office Action, 6 pages.

U.S. Appl. No. 15/331,393: Jan. 19, 2017 Pre-Interview Communication, 4 pages.

U.S. Appl. No. 15/331,393: Mar. 20, 2017 Examiner's Interview Summary and First Action Interview Office Action Summary, 5 pages.

U.S. Appl. No. 15/331,648: Jan. 19, 2017 Pre-Interview Communication, 4 pages.

U.S. Appl. No. 15/331,648: Mar. 17, 2017 Examiner's Interview Summary, 3 pages.

U.S. Appl. No. 15/337,274: Mar. 24, 2017 Nonfinal Office Action, 10 pages.

U.S. Appl. No. 15/341,377: Jan. 30, 2017 Nonfinal Office Action, 12 pages.

U.S. Appl. No. 15/341,377: Apr. 18, 2017 Final Office Action, 13 pages.

(56) References Cited

OTHER PUBLICATIONS

U.S. Appl. No. 15/341,619: Apr. 3, 2017 Pre-Interview Communication, 3 pages.
U.S. Appl. No. 15/363,761: Jan. 18, 2017 Nonfinal Office Action, 15 pages.
U.S. Appl. No. 15/363,761: Aug. 1, 2017 Final Office Action, 18 pages.
U.S. Appl. No. 15/363,761: Dec. 14, 2017 Examiner Interview Summary, 3 pages.
U.S. Appl. No. 15/363,923: Feb. 1, 2017 Nonfinal Office Action, 24 pages.
U.S. Appl. No. 15/363,923: Sep. 13, 2017 Final Office Action, 29 pages.
U.S. Appl. No. 15/363,978: Feb. 7, 2017 Nonfinal Office Action, 16 pages.
U.S. Appl. No. 15/363,978: Aug. 21, 2017 Final Office Action, 19 pages.
U.S. Appl. No. 15/363,978: Dec. 14, 2017 Examiner Interview Summary, 3 pages.
U.S. Appl. No. 15/364,021: Mar. 9, 2017 Nonfinal Office Action, 18 pages.
U.S. Appl. No. 15/364,021: Oct. 4, 2017 Final Office Action, 20 pages.
U.S. Appl. No. 15/375,039: Feb. 16, 2018 Nonfinal Office Action, 11 pages.
U.S. Appl. No. 15/403,441: Dec. 21, 2017 Nonfinal Office Action, 9 pages.
U.S. Appl. No. 15/645,645: Dec. 1, 2017 Nonfinal Office Action, 16 pages.
U.S. Appl. No. 15/652,513: Dec. 20, 2017 Nonfinal Office Action, 13 pages.
U.S. Appl. No. 15/661,868: Dec. 1, 2017 Nonfinal Office Action, 15 pages.
U.S. Appl. No. 15/664,930: Dec. 20, 2017 Nonfinal Office Action, 7 pages.
U.S. Appl. No. 15/664,976: Sep. 11, 2018 Nonfinal Office Action, 23 pages.
U.S. Appl. No. 15/664,976: May 21, 2019 Nonfinal Office Action, 11 pages.
U.S. Appl. No. 15/768,352: Feb. 14, 2019 Non-Final Office Action, 15 pages.
U.S. Appl. No. 15/809,815: Mar. 6, 2018 Nonfinal Office Action, 12 pages.
U.S. Appl. No. 15/809,815: Sep. 11, 2018 Final Office Action, 14 pages.
U.S. Appl. No. 15/852,551: Jan. 11, 2019 Nonfinal Office Action, 5 pages.
U.S. Appl. No. 15/967,638: Jan. 14, 2019 Nonfinal Office Action, 14 pages.
U.S. Appl. No. 16/012,351: Mar. 8, 2019 Non-Final Office Action, 13 pages.
U.S. Appl. No. 16/012,372: Mar. 8, 2019 Non-Final Office Action, 8 pages.
Kirpotin D, et al. "Antibody Targeting of Long-Circulating Lipidic Nanoparticles Does Not Increase Tumor Locatlization out Does Increase Internalization in Animal Models," Cancer Res. 66(13):6732-40 (2006).
Klinz S, et al., "Identifying Differential Mechanisms of Action for MM-398/PEP02, a Novel Nanotherapeutic Encapsulation of Irinotecan." Poster presented at MCR, Nov. 12-16, 2011, 8 pages.
Klinz S, et al., "Identifying Differential Mechanisms of Action for MM-398/PEP02, a Novel Nanotherapeutic Encapsulation of Irinotecan," Mol Cancer Ther. 10(11 Suppl):Abstract C207. Molecular Targets and Therapeutics Meeting (2011), 2 printed pages.
Klinz S, et al., "Nanoliposomal Irinotecan (nal-IRI) is an Active Treatment and Reduces Hypoxia as Measured Through Longitudinal Imaging Using [18F]FAZA-PET in an Orthotopic Patient-Derived Tumorgraft Model of Pancreatic Cancer." Poster presented at AACR Pancreatic meeting Orlando, FL, May 12-15, 2016, 10 pages.
Klinz S, et al., Abstract C293: "Irinotecan Sucrosofate Liposome Injection, MM-398, Demonstrates Superior Activity and Control of Hypoxia as Measured Through Longitudinal Imaging Using [18F] FAZA PET Compared to Free Irinotecan in a Colon Adenocarcinoma Xenografl Model." Poster presented at AACR-NCI-EORTC International Conference on Molecular Targets and Cancer Therapeutics on Oct. 19, 2013, 7 pages.
Klinz S, et al.,"MM-302 a HER2-targeted Liposomal Doxorubicin, Shows Binding/Uptake and Efficacy in HER2 2+ Cells and Xenografl Models," Cancer Res. 71:Abstract 3637 (2011), 1 printed page.
Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013).
Ko A, et al., "A Multinational Phase II Study of PEP02 (Liposome Irinotecan) for Patients with Gemcitabine-Refractory Metastatic Pancreatic Cancer," J Clin Oncol. 29:2011 (Suppl; Abstract 4069). 2011 ASCO Annual Meeting (2011), 2 printed pages.
Ko A, et al., "A Multinational Phase II Study of PEP02 (MM-398), Liposome Irinotecan, for Patients with Gemcitabine-refractory Metastatic Pancreatic Cancer." Poster presented at the American Society of Clinical Oncology meeting, Jun. 3-Jun. 7, 2011, Chicago, Illinois, 9 pages.
Ko A, et al., "Excess Toxicity Associated with Docetaxel and Irinotecan in Patients with Metastatic, Gemcitabine-Refractory Pancreatic Cancer: Results of a Phase II Study," Cancer Invest. 26(1):47-52 (2008).
Kohne C, et al., "Randomized Phase III Study of High-Dose Fluorouracil Given as a Weekly 24-Hour Infusion With or Without Leucovorin Versus Bolus Fluorouracil Plus Leucovorin in Advanced Colorectal Cancer: European Organization of Research and Treatment of Cancer Gastrointestinal Group Study 40952," J Clin Oncol. 21(20):3721-8 (2003).
Kom R, "Advanced Imaging with Ferumoxytol MRI to Predict Drug Delivery." Presentation presented at Pancreatic Cancer 2014, Feb. 22, 2014, 23 pages.
Kozuch P, et al., "Irinotecan Combined with Gemcitabine, 5-Fluorouracil, Leucovorin, and Cisplatin (G-FLIP) is an Effective and Noncrossresistant Treatment for Chemotherapy Refractory Metastatic Pancreatic Cancer," Oncologist. 6(6):488-95 (2001).
Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007).
Landry R, et al., "Pharmacokinetic Study of Ferumoxytol: A New Iron Repalcement Therapy in Normal Subjects and Hemodialysis Patients," Am J Nephrol. 25(4):400-10 (2005).
Lee C, et al. "Novel Chondroitin Sulfate-binding Cationic Liposomes Loaded with Cisplatin Efficiently Suppress the Local Growth and Liver Metastasis of Tumor Cells in Vivo," Cancer Res. 62(15):4282-8 (2002).
Lee H, et al., A Novel 64Cu-Liposome PET Agent (MM-DX-929) Predicts Response to Liposomal Chemotherapeutics in Preclinical Breast Cancer Models, Cancer Res. 72(24 Suppl): Abstract nrP4-02-05 (2012), San Antonio Breast Cancer Symposium, Dec. 4-8, 2012, 2 printed pages.
Lee H, et al., A Novel 64Cu-Liposome PET Agent (MM-DX-929) Predicts Response to Liposomal Chemotherapeutics in Preclinical Breast Cancer Models, Poster presented at San Antonio Breast Cancer Symposium, Dec. 4-8, 2012, 13 pages.
Lee H, et al., "Delivery and Anti-Tumor Activity of Nanoliposomal Irinotecan (Nal-IRI, MM-398) in Metastatic Xenograft Models of Triple Negative Breast Cancer." Poster presented at 39th Annual San Antonio Breast Cancer Symposium, Dec. 6-10, 2016, 8 pages.
Lee M, et al., "5-Fluorouracil/Leucovorin Combined wtih Irinotecan and Oxaliplatin (FOLFIRINOX) as Second-Line Chemotherapy in Patients with Advanced Pancreatic Cancer Who Have Progressed on Gemcitabine-Based Therapy," Chemotherapy. 59(4):273-9 (2013).
Fordick F, et al., "Phase II Study of Weekly Oxaliplatin Plus Infusional Fluorouracil and Folinic Acid (FUFOX Regiment) as First-Line Treatment in Metastatic Gastric Cancer," Br J Cancer 93(2):190-4 (2005).

(56) References Cited

OTHER PUBLICATIONS

Louvet C, et al., "Gemcitabine in Combination With Oxaliplatin Compared With Gemcitabine Alone in Locally Advanced or Metastatic Pancreatic Cancer: Results of a GERCOR and GISCAD Phase III Trial," J Clin Oncol. 23(15):3509-16 (2005).
Ma W, et al., "Nanoliposomal Irinotecan (nal-IRI, nal-IRI) Population Pharmacokinetics (PK) and Its Association with Efficacy and Safety in Patients with Solid Tumors." Poster presented at 2015 European Cancer Congress, Vienna, Austria, Sep. 25, 2015, 7 pages.
Maddison J, et al., "Sucralfate," In Small Animal Clinical Pharmacology at p. 474, published by W. B. Saunders (2002).
Mahaseth H, et al., "Modified FOLFIRINOX Regimen With Improved Safety and Maintained Efficacy in Pancreatic Adenocarcinoma," Pancreas. 42(8):1311-5 (2013).
Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011).
Mamot C, et al., "Epidermal Growth Factor Receptor-Targeted Immunoliposomes Significantly Enhance the Efficacy of Multiple Anticancer Drugs In Vivo," Cancer Res. 65(24):11631-8 (2005).
Mamot C, et al., "Extensive Distribution of Liposomes in Rodent Brains and Brain Tumors Following Convection-Enhanced Delivery," J Neurooncol. 68(1):1-9 (2004).
Mans D, et al., "Sequence-Dependent Growth Inhibition and DNA Damage Formation by the Irinotecan-5-Fluorouracil Combination in Human Colon Carcinoma Cell Lines," Eur J Cancer. 35(13):1851-61 (1999).
Mathé G, et al., "A Phase I Trial of Trans-1-diamino-cyclohexane Oxalate-platinum (I-OHP)," Biomed Pharmacother, 40(10):372-376 (1986).
Mathé G, et al., "Oxalato-platinum or 1-OHP, a Third-Generation Platinum Complex: An Experimental and Clinical Appraisal and Preliminary Comparison with Cis-platinum and Carboplatinum," Biomed Pharmacother, 43(4):237-50 (1989).
Merrimack Pharmaceuticals, "Merrimack Announces Inclusion of ONIVYDE (irinotecan liposome injection) as a Category 1 Treatment Option in the 2016 NCCN Guidelines for Pancreatic Adenocarcinoma," Mar. 24, 2016. Retrieved from http://investors.merrimack.com/news-releases/news-release-details/merrimack-announces-inclusion-onivyder-irinotecan-liposome, 2 printed pages.
Miles D, et al., "Combination Versus Sequential Single-Agent Therapy in Metastatic Breast Cancer," Oncologist. 7(suppl 6):13-19 (2002).
Miller M, et al. "Predicting Therapeutic Nanomedicine Efficacy Using a Companion Magnetic Resonance Imaging Nanoparticule," Sci Transl Med. 7:314ra183 (2015), pp. 1-12, Editor's Summary (1 page), and Supplementary Materials (24 pages).
Miller M, et al., "Tumour-Associated Macrophages Act as a Slow-Release Reservoir of Nano-Therapeutic Pt(IV) Pro-Drug," Nat. Commun. 6:8692, doi: 10.1038/ncomms9692, 13 pages (2015), Supplementary Figures 1-9 (9 pages), Supplementary Table 1 (1 page), and Supplementary References (1 page).
Minami H, et al., "Irinotecan Pharmacokinetics/Pharmacodynamics and UGT1A Genetic Polymorphisms in Japanese: Roles of UGT1A1*6 and *28," Pharmacogenet Genomics. 17(7):497-504 (2007).
Mizuno N., "Randomized Phase II Trial of S-1 versus S-1 Plus Irinotecan (IRIS) in Patients with Gemcitabine-Refractory Pancreatic Cancer," J Clin Oncol. 31(Suppl 4):Abstract 263 (2013), 2 printed pages.
Mohammad A, et al., "Liposomal Irinotecan Accumulates in Metastatic Lesions, Crosses the Blood-Tumor Barrier (BTB), and Prolongs Survival in an Experimental Model of Brain Metastases of Triple Negative Breast Cancer," Pharm Res. 35(2):31; doi.org/10.1007/s11095-017-2278-0 (2018), 10 pages.
Morgan R, et al., "Human Cell Line (COLO 357) of Metastatic Pancreatic Adenocarcinoma," Int J Cancer 25(5):591-8 (1980).
Mukhtar R, et al., "Elevated PCNA+ Tumor-Associated Macrophages in Breast Cancer are Associated with Early Recurrence and Non-Caucasian Ethnicity," Breast Cancer Res Treat. 130(2):635-44 (2011).
Mullany S, et al., "Effect of Adding the Topoisomerase I Poison 7-ethyl-10-hydroxy-camptothecin (SN-38) to 5-Fluorouracil and Folinic Acid in HCT-8 Cells: Elevated dTTP Pools and Enhanced Cytotoxicity," Cancer Chemother Pharmacol. 42(5):391-9 (1998).
Münstedt K, et al., "Role of Dexamethasone Dosage in Combination with 5-HT3 Antagonists for Prophylaxis of Acute Chemotherapy-Induced Nausea and Vomiting," Br J Cancer 79(3-4):637-9 (1999).
National Comprehensive Cancer Network Clinical Practice Guidelines in Oncology (NCCN Guidelines). "Pancreatic Adenocarcinoma." Version I.2016. Mar. 22, 2016 (PANC-9), 133 pages.
Nentwich, F., "Doxorubicin Hydrochloride," In Intravenous Therapy: A Comprehensive Application of Intravenous Therapy and Medication Administration at p. 310. Published by Jones & Bartlett Learning, 1990.
Neuzillet C, et al., "FOLFIRI Regimen in Metastatic Pancreatic Adenocarcinoma Resistant to Gemcitabine and Platinum-Salts," World J Gastroenterol. 18(33):4533-41 (2012).
Neuzillet C., et al., "FOLFIRI Regimen as Second-/Third-line Chemotherapy in Patients with Advanced Pancreatic Adenocarcinoma Refradory to Gemcitabine and Platinum Salts: A Retrospective Series of 70 Patients." J Clin Oncol. 29: 2011 (Suppl 4; Abstract 272). 2011 Gastrointestinal Cancers Symposium (2011), 2 printed pages.
NIH National Cancer Institute, "FDA Approves Irinotecan Liposome to Treat Pancreatic Cancer," Nov. 24, 2015 by NCI Staff, 2 printed pages.
Noble C, et al., "Novel Nanoliposomal CPT-11 Infused by Convection-Enhanced Delivery in Intracranial Tumors: Pharmacology and Efficacy," Cancer Res. 66(5):2801-6 (2006).
Noble C, et al., "Pharmacokinetics, Tumor Accumulation and Antitumor Activity of Nanoliposomal Irinotecan Following Systemic Treatment of Intracranial Tumors," Nanomedicine. 9(14):2099-108 (2014).
O'Dwyer P, et al., "Uridine Diphosphate Glucuronosyltransferase (UGT) 1A1 and Irinotecan: Practical Pharmacogenomics Arrives in Cancer Therapy," J Clin Oncol. 24(28):4534-8 (2006).
Oettle H, et al., "Second-Line Oxaliplatin, Folinic Acid, and Fluorouracil Versus Folinic Acid and Fluorouracil Alone for Gemcitabine-Refractory Pancreatic Cancer: Outcomes From the CONKO-003 Trial," J Clin Oncol. 32(23):2423-9 (2014).
Oh S, et al., "Pilot Study of Irinotecan/Oxaliplatin (IROX) Combination Chemotherapy for Patients with Gemcitabine- and 5-Fluorouracil-Refractory Pancreatic Cancer," Invest New Drugs. 28(3):343-9 (2010), Epub May 15, 2009.
Ohkawa S, et al., "Randomised Phase II Trial of S-1 Plus Oxaliplatin vs S-1 in Patients with Gemcitabine-Refractory Pancreatic Cancer," Br J Cancer. 112(9):1428-34 (2015).
Okusaka T, et al., "Phase II Study of Folfirinox for Chemotherapy-Naive Japanese Patients with Metastatic Pancreatic Cancer," Cancer Sci. 105(10):1321-6 (2014).
Onivyde [MM-398] package insert, revision Oct. 22, 2015, retrieved from http://www.accessdata.fda.gov/drugsatfda_docs/label/2015/207793lbl.pdf, 18 pages.
Oxaliplatin package insert, revision Nov. 2013, retrieved from https://www.accessdata.fda.gov/drugsatfda_docs/label/2013/022160s009lbl.pdf, 43 pages.
Palomaki G, et al., "Can UGT1A1 Genotyping Reduce Morbidity and Mortality in Patients with Metastatic Colorectal Cancer Treated with Irinotecan? An Evidence-Based Review," Genet Med. 11(1):21-34 (2009).
Park J, et al., "Anti-HER2 Immunoliposomes: Enhanced Efficacy Attributable to Targeted Delivery," Clin Cancer Res. 8(4):1172-81 (2002).
Patton W, "Detection Technologies in Proteome Analysis," J Chromatogr B. 771(1-2):3-31 (2002).
Pavillard V, et al., "Combination of Irinotecan (CPT11) and 5-Fluorouracil with an Analysis of Cellular Determinants of Drug Activity," Biochem Pharmacol. 56(10):1315-22 (1998).
PCT/US2013/045495: International Preliminary Report on Patentability dated Dec. 16, 2014, 8 pages.
PCT/US2013/045495: International Search Report and Written Opinion dated Aug. 22, 2013, 11 pages.

(56) References Cited

OTHER PUBLICATIONS

PCT/US2013/046914: International Preliminary Report on Patentability dated Dec. 23, 2014, 7 pages.
PCT/US2013/046914: PCT International Search Report dated Sep. 2, 2013, 3 pages.
PCT/US2013/075513: PCT International Preliminary Report on Patentability dated Jun. 16, 2015, 7 pages.
PCT/US2013/075513: PCT International Search Report dated Jun. 6, 2014, 2 pages.
PCT/US2014/062007: PCT International Preliminary Report on Patentability dated Apr. 26, 2016, 10 pages.
PCT/US2014/062007: PCT International Search Report dated Jan. 9, 2015, 3 pages.
PCT/US2015/064491: PCT International Preliminary Report on Patentability dated Jun. 13, 2017, 7 pages.
PCT/US2015/064491: PCT International Search Report dated Feb. 19, 2016, 4 pages.
PCT/US2016/047727: International Preliminary Report on Patentability dated Feb. 27, 2018, 6 pages.
PCT/US2016/047727: PCT International Search Report and Written Opinion dated Nov. 16, 2016, 8 pages.
Peddi P, et al., “Multi-Institutional Experience with FOLFIRINOX in Pancreatic Adenocarcinoma,” Journal of the Pancreas (JOP). 13(5):497-501 (2012), online access, 11 printed pages.
Pelzer U, et al., “A Randomized Trial in Patients With Gemcitabine Refractory Pancreatic Cancer. Final Results of the CONKO 003 Study,” J Clin Oncol. 2008 ASCO Annual Meeting Proceedings. 26(15S):4508 (2008), 2 printed pages.
Pelzer U, et al., “Second-Line Therapy in Refractory Pancreatic Cancer. Results of a Phase II Study,” Onkologie. 32(3):99-102 (2009).
Petrioli R, et al., “Gemcitabine, Oxaliplatin, and Capecitabine (GEMOXEL) Compared with Gemcitabine Alone in Metastatic Pancreatic Cancer: A Randomized Phase II Study,” Cancer Chemother Pharmacol. 75(4):683-90 (2015).
Pfizer Background Document on the UGT1A1 Polymorphisms and Irinotecan Toxicity: ACPS Nov. 3, 2004 4dvisory Committee Meeting, 19 pages.
Pliarchopoulou K, et al., “Pancreatic Cancer: Current and Future Treatment Strategies,” Cancer Treat Rev. 35(5):431-6 (2009).
Poplin E, et al., “Phase III, Randomized Study of Gemcitabine and Oxaliplatin Versus Gemcitabine (Fixed-Dose Rate Infusion) Compared With Gemcitabine (30-Minute Infusion) in Patients With Pancreatic Carcinoma E6201: A Trial of the Eastern Cooperative Oncology Group,” J Clin Oncol. 27(23):3778-85 (2009).
Qin B, et al., “In-vitro Schedule-Dependent Interaction Between Oxaliplatin and 5-Fluorouracil in Human Gastric Cancer Cell Lines,” Anti-Cancer Drugs. 17(4):445-53 (2006).
Rahib L, et al., “Projecting Cancer Incidence and Deaths to 2030: The Unexpected Burden of Thyroid, Liver, and Pancreas Cancers in the United States,” Cancer Res. 74(11):2913-21 (2014).
Rahma O, et al., “Second-Line Treatment in Advanced Pancreatic Cancer: A Comprehensive Analysis of Published Clinical Trials,” Ann Oncol. 24(8):1972-9 (2013), epub doi:10.1093/annonc/mdt166, May 12, 2013, pp. 1-8.
Ramanathan R, et al., “Correlation between Ferumoxytol Uptake in Tumor Lesions by MRI and Response to Nanoliposomal Irinotecan in Patients with Advanced Solid Tumors: A Pilot Study,” Clin Cancer Res. 23(14):3638-48 (2017).
Ramanathan R, et al., “Lesion Characterization with Ferumoxytol MRI in Patients with Advanced Solid Tumors and Correlation with Treatment Response to MM-398, Nanoliposomal Irinotecan (nal-IRI).” Poster presented at EORTC-NCI-AACR International Conference on Molecular Targets and Cancer Therapeutics on Nov. 20, 2014, 7 pages.
Ramanathan R, et al., “Pilot Study in Patients with Advanced Solid Tumors to Evaluate Feasibility of Ferumoxytol (FMX) as a Tumor Imaging Agent Prior to MM-398, a Nanoliposomal Irinotecan (nal-IRI).” Poster presented at AACR Annual Meeting 2014, San Diego, CA, 9 pages.
Reni M, et al., “Salvage Chemotherapy with Mitomycin, Docetaxel, and Irinotecan (MDI Regimen) in Metastatic Pancreatic Adenocarcinoma: A Phase I and II Trial,” Cancer Invest. 22(5):688-96 (2004).
Rivory L, et al., “Pharmacokinetic Interrelationships of Irinotecan (CPT-11) and Its Three Major Plasma Metabolites in Patients Enrolled in Phase I/II Trials,” Clin Cancer Res. 3(8):1261-6 (1997).
Rombouts S, et al., “FOLFIRINOX in Locally Advanced and Metastatic Pancreatic Cancer: A Single Centre Cohort Study,” J Cancer 7(13):1861-6 (2016).
Rothenberg M, et al., “Phase I and Pharmacokinetic Trial of Weekly CPT-11,” J Clin Oncol. 11(11):2194-204 (1993).
Sachdev J, et al., A Phase 1 Study in Patients with Metastatic Breast Cancer to Evaluate the Feasibility of Magnetic Resonance Imaging with Ferumoxytol as a Potential Biomarker for Response to Treatment with Irinotecan Liposome Injection (nal-IRI, MM-398). Poster presented at 38th Annual San Antonio Breast Cancer Symposium on Dec. 8, 2015, 10 pages.
Sachdev J, et al., “Characterization of Metastatic Breast Cancer Lesions with Ferumoxytol MRI and Clinical Response to MM-398, Nanoliposomal Irinotecan (nal-IRI), in 3 Subjects.” Poster presented at San Antonio Breast Cancer Symposium 2014, 8 pages.
Sachdev J, et al., “Characterization of Metastatic Breast Cancer Lesions with Ferumoxytol MRI and Treatment Response to MM-398, Nanoliposomal Irinotecan (nal-IRI),” Cancer Res.75(9 Suppl): Abstract P5-01-06 (2015), 3 printed pages.
Sadzuka Y, et al. “Effect of Liposomalization on the Antitumor Activity, Side-Effects and Tissue Distribution of CPT-11,” Cancer Lett. 127(1-2): 99-106 (1998).
Saito R, et al., “Distribution of Liposomes into Brain and Rat Brain Tumor Models by Convection-Enhanced Delivery Monitored with Magnetic Resonance Imaging,” Cancer Res. 64(7):2572-9 (2004).
Saito R, et al., “Gadolinium-loaded Liposomes Allow for Real-Time Magnetic Resonance Imaging of Convection-Enhanced Delivery in the Primate Brain,” Exp Neurol. 196(2):381-9 (2005).
Saito R, et al., “Tissue Affinity of the Infusate Affects the Distribution Volume During Convection-Enhanced Delivery into Rodent Brains: Implications for Local Drug Delivery,” J Neurosci Methods. 154(1-2):225-32 (2006).
Saltz L, et al., “Irinotecan Plus Fluorouracil and Leucovorin for Metastatic Colorectal Cancer. Irinotecan Study Group,” N Engl J Med. 343(13):905-14 (2000).
Shimoda S, et al., “Irinotecan Plus Low-Dose Cisplatin for a-Fetoprotein-Producing Gastric Carcinoma with Multiple Liver Metastases: Report of Two Cases,” Surg Today. 32(12):1075-80 (2002).
Siegel R, et al., “Cancer Statistics, 2015,” CA Cancer J Clin. 65(1):5-29 (2015).
Stein S, et al., “Final Analysis of a Phase II Study of Modified Folfirinox in Locally Advanced and Metastatic Pancreatic Cancer,” Br J Cancer 114(7):737-43 (2016).
Abraxane package insert, revision Dec. 23, 2011, retrieved from https://www.accessdata.fda.gov/drugsatfda_docs/label/2011/021660s025s026s029lbl.pdf, 13 pages.
Abraxane package insert, revision Jul. 21, 2015, retrieved from https://www.accessdatafda.gov/drugsatfda_docs/label/2015/021660s041lbl.pdf, 24 pages.
Ahmad I, et al., “Antibody-Targeted Delivery of Doxorubicin Entrapped in Stoically Stabilized Liposomes Can Eradicate Lung Cancer in Mice,” Cancer Res. 53(7):1484-8 (1993).
Alberts S., et al. “Gemcitabine and Oxaliptatin for Metastatic Pancreatic Adenocarcinoma: A North Central Cancer Treatment Group Phase II Study,” Ann Oncol. 14(4):580-5 (2003).
Alcindor T, et al., “Oxaliplatin: A Review in the Era of Molecularly Targeted Therapy,” Curr Oncol. 18(1):18-25 (2011).
Alfert M, et al., “A Selective Staining Method for the Basic Proteins of Cell Nuclei,” Proc Natl Acad Sci Usa. 39(10):991-9 (1953).
American Chemical Society (ACS), http://www.cancer.org/cancer/pancreaticcancer/detailedguide/pancreatic-cancer-what-is-pancreatic-cancer, retrieved Dec. 10, 2017, 7 printed pages.
American Chemical Society (ACS), http://www.cancer.org/cancer/pancreaticcancer/detailedguide/pancreatic-cancer-what-is-pancreatic-cancer, retrieved Dec. 1, 2016, 4 printed pages.

(56) References Cited

OTHER PUBLICATIONS

Assaf E, et al., "5-Fluorouracil/Leucovorin Combined with Irinotecan and Oxaliplatin (FOLFIRINOX) as Second-Line Chemotherapy in Patients with Metastatic Pancreatic Adenocarcinoma," Oncology. 80(5-6):301-6 (2011).

Author Unknown, "From Antinutrient to Phytonutrient: Phytic Acid Gains Respect." HighBeam Research, Environmental Nutrition, Apr. 1, 2004, 2 printed pages. URL: http://www.highbeam.com/doc/1G1-116341390.html/print (accessed Nov. 4, 2011).

Azrak R, et al., "Therapeutic Synergy Between Irinotecan and 5-Fluorouracil against Human Tumor Xenografts," Clin Cancer Res. 10(3):1121-9 (2004).

Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22):7260-71 (2008).

Boeck S, et al., "Capecitabine Plus Oxaliplatin (CapOx) versus Capecitabine Plus Gemcitabine (CapGem) versus Gemcitabine Plus Oxaliplatin (mGemOx): Final Results of a Multicenter Randomized Phase II Trial in Advanced Pancreatic Cancer," Ann Oncol. 19(2):340-7 (2008), Epub Oct. 24, 2007.

Brixi-Benmansour H, et al., "Phase II Study of First-line Folfiri for Progressive Metastatic Well-differentiated Pancreatic Endocrine Carcinoma," Dig Liver Dis. 43(11):912-6 (2011).

Burris H, et al., "Phase II Trial of Oral Rubitecan in Previously Treated Pancreatic Cancer Patients," Oncologist. 10(3):183-90 (2005).

Butt R, et al., "Postfractionation for Enhanced Proteomic Analyses: Routine Electrophoretic Methods Increase the Resolution of Standard 2D-PAGE," J Proteome Res. 4(3):982-91 (2005).

CAMPTOSAR package insert, revised May 16, 2002, 37 pages.

CAMPTOSAR package insert, revision Dec. 19, 2014, retrieved from https://www.accessdata.fda.gov/drugsatfda_docs/label/2014/020571s048lbl.pdf, initial U.S. approval 1996, 40 printed pages.

CAMPTOSAR package insert, revision May 14, 2010, retrieved from https://www.accessdata.fda.gov/drugsatfda_docs/label/2010/020571s0315032s0335036s037lbl.pdf, 37 pages.

Cantore M, et al., "Combined Irinotecan and Oxaliplatin in Patients with Advanced Pre-Treated Pancreatic Cancer," Oncology 67(2):93-7 (2004).

CAS Registry Record for 23214-92-8 (doxorubicin), entered STN Nov. 16, 1984, 2 pages.

CAS Registry Record for 97682-44-5 (irinotecan), entered STN Aug. 18, 1985, 1 page.

Cereda S, et al., "XELIRI or FOLFIRI as Salvage Therapy in Advanced Pancreatic Cancer," Anticancer Res. 30(11):4785-90 (2010).

Chang T, et al., "Phase I Study of Nanoliposomal Irinotecan (PEP02) in Advanced Solid Tumor Patients," Cancer Chemother Pharmacol. 75(3):579-86 (2015).

Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster presented at the Gastrointestinal Cancers Symposium of the ASCO meeting of Jan. 21-23, 2016, San Francisco, California, 16 pages.

Chen L, et al., "Expanded Analyses of NAPOLI-1: Phase 3 Study of MM-398 (nal-IRI), With or Without 5-Fluorouracil and Leucovorin, Versus 5-Fluorouracil and Leucovorin, in Metastatic Pancreatic Cancer (mPAC) Previously Treated with Gemcitabine-Based Therapy." Poster presented at the ASCO meeting of May 29-Jun. 2, 2015, Chicago, Illinois, 7 pages.

Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 1 page.

Chen L, et al., "Phase I Study of Liposome Encapsulated Irinotecan (PEP02) in Advanced Solid Tumor Patients," Poster presented at the ASCO meeting of May 30-Jun. 3, 2008, Chicago, Illinois, 9 pages.

Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page.

Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012.

Chibaudel B, et al., "PEPCOL: A Randomized Non-Comparative Phase II Study to Evaluate the Efficacy and Safety of PEP02 (MM-398) or Irinotecan in Combination with Leucovorin and 5-Fluorouracil as Second-Line Treatment for Patients with Unresectable Metastatic Colorectal Cancer. A GERCOR Study." Poster presented at ASCO 2015, 6 pages.

Chiesa M, et al., "A Pilot Phase Ii Study of Chemotherapy with Oxaliplatin, Folinic Acid, 5-Fluorouracil and Irinotecan in Metastatic Gastric Cancer," Tumori. 93(3):244-7 (2007).

Chou T, et al., "Effect of Composition on the Stability of Liposomal Irinotecan Prepared by a pH Gradient Method," J Biosci Bioeng. 95(4):405-8 (2003).

Clarke J, et al., "A Phase 1 Trial of Intravenous Liposomal Irinotecan in Patients with Recurrent High-Grade Glioma," Cancer Chemother Pharmacol. 79(3):603-10 (2017).

Clinical Trials Identifier NCT00104754: Jul. 20, 2016 update, first posted Mar. 4, 2005, "Phase II Trial of Liposome Encapsulated SN38 (LE-SN38) in the Treatment of Small Cell Lung Cancer." Retrieved from ClinicalTrials.gov archive, 8 printed pages.

Clinical Trials Identifier NCT00311610: Jun. 29, 2016 update, first posted Apr. 6, 2006, "Phase II Trial of LE SN38 in Patients with Metastatic Colorectal Cancer After Progression on Oxaliplatin." Retrieved from ClinicalTrials.gov archive, 8 printed pages.

Clinical Trials Identifier NCT00364143: Jan. 26, 2012 update, first posted Aug. 15, 2006, "A Phase I Study of IHL-305 (Irinotecan Liposome Injection) in Patients With Advanced Solid Tumors." Retrieved from ClinicalTrials.gov archive, 8 printed pages.

Clinical Trials Identifier NCT00734682: Jan. 7, 2015 update, first posted Aug. 14, 2008, "A Phase I Trial of Nanoliposomal CPT-11 (NL CPT-11) in Patients With Recurrent High-Grade Gliomas." Retrieved from ClinicalTrials.gov archive, 6 printed pages.

Clinical Trials Identifier NCT00813072: Mar. 2, 2012 update, first posted Dec. 22, 2008, "A Randomized Phase II Study of PEP02, Irinotecan or Docetaxel as a Second Line Therapy in Patients With Locally Advanced or Metastatic Gastric or Gastroesophageal Junction Adenocarcinoma." Retrieved from ClinicalTrials.gov archive, 9 printed pages.

Clinical Trials Identifier NCT00813163: Jan. 11, 2011 update, "A Phase II Study of PEP02 as a Second Line Therapy for Patients With Metastatic Pancreatic Cancer." Retrieved from ClinicalTrials.gov archive, 3 printed pages.

Clinical Trials Identifier NCT00813163: Mar. 1, 2012 update, "A Phase II Study of PEP02 as a Second Line Therapy for Patients With Metastatic Pancreatic Cancer." Retrieved from ClinicalTrials.gov archive, 3 printed pages.

Clinical Trials Identifier NCT00813163: Jan. 12, 2015 update, "A Phase II Study of PEP02 as a Second Line Therapy for Patients with Metastatic Pancreatic Cancer." Retrieved from ClinicalTrials.gov archive, 3 printed pages.

Clinical Trials Identifier NCT00813163: Apr. 6, 2017 update, first posted Dec. 22, 2008, "A Phase II Study of PEPO2 as a Second Line Therapy for Patients With Metastatic Pancreatic Cancer." Retrieved from ClinicalTrials.gov archive, 6 printed pages.

Clinical Trials Identifier NCT00940758: Jul. 16, 2009 update, "Pharrnacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.

Clinical Trials Identifier NCT00940758: Feb. 3, 2010 update, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.

Clinical Trials Identifier NCT00940758: Mar. 1, 2012 update, "Phase I and Pharmacokinetic Study of Biweekly PEP02 (Liposome

(56) References Cited

OTHER PUBLICATIONS

Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Apr. 6, 2017 update, first posted Jul. 16, 2009, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 5 printed pages.
Clinical Trials Identifier NCT01359007: May 23, 2011 update, "A Phase II Study Evaluating the Rate of RO Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer." Retrieved from ClinicalTrials.gov archive, 3 printed pages.
PCT/US2016/047814: PCT International Preliminary Report on Patentability dated Feb. 20, 2018, 6 pages.
PCT/US2016/047827: PCT International Preliminary Report on Patentability dated Feb. 20, 2018, 6 pages.
U.S. Appl. No. 11/121,294: Aug. 17, 2009 Nonfinal Office Action, 33 pages.
U.S. Appl. No. 11/121,294: Mar. 12, 2010 Final Office Action, 15 pages.
U.S. Appl. No. 11/121,294: May 19, 2010 Advisory Action, 3 pages.
U.S. Appl. No. 11/121,294: Aug. 4, 2010 Nonfinal Office Action, 14 pages.
U.S. Appl. No. 11/121,294: Dec. 6, 2010 Final Office Action, 17 pages.
U.S. Appl. No. 11/121,294: Apr. 13, 2011 Nonfinal Office Action, 10 pages.
U.S. Appl. No. 11/121,294: Jul. 12, 2011 Examiner Interview Summary, 3 pages.
U.S. Appl. No. 11/121,294: Nov. 23, 2011 Final Office Action, 20 pages.
U.S. Appl. No. 11/601,451: Jan. 11, 2010 Nonfinal Office Action, 14 pages.
U.S. Appl. No. 11/601,451: Aug. 27, 2010 Final Office Action, 17 pages.
U.S. Appl. No. 11/601,451: Jul. 12, 2011 Examiner Interview Summary, 4 pages.
U.S. Appl. No. 13/416,204: May 8, 2012 Pre-Interview Communication, 4 pages.
U.S. Appl. No. 13/416,204: Jun. 29, 2012 Interview Summary and First Action Interview Office Action, 6 pages.
U.S. Appl. No. 13/654,373: Aug. 12, 2013 Nonfinal Office Action and Interview Summary, 10 pages.
U.S. Appl. No. 14/151,632: Apr. 18, 2016 Nonfinal Office Action, 9 pages.
U.S. Appl. No. 14/175,365: Jun. 26, 2014 Nonfinal Office Action, 20 pages.
U.S. Appl. No. 14/406,776: Feb. 26, 2016 Nonfinal Office Action, 9 pages.
U.S. Appl. No. 14/632,422: Jan. 10, 2017 Nonfinal Office Action, 18 pages.
U.S. Appl. No. 14/812,950: Oct. 2, 2015 Pre-Interview Communication, 3 pages.
U.S. Appl. No. 14/844,500: Dec. 16, 2015 Nonfinal Office Action, 25 pages.
U.S. Appl. No. 14/851,111: Feb. 25, 2016 Nonfinal Office Action, 13 pages.
U.S. Appl. No. 14/879,302: Aug. 15, 2016 Nonfinal Office Action, 30 pages.
U.S. Appl. No. 14/879,302: Dec. 15, 2016 Nonfinal Office Action, 14 pages.
U.S. Appl. No. 14/879,358: Dec. 28, 2015 Nonfinal Office Action, 20 pages.
U.S. Appl. No. 14/879,358: Jul. 12, 2016 Nonfinal Office Action, 14 pages.
U.S. Appl. No. 14/964,239: Nov. 4, 2016 Nonfinal Office Action, 21 pages.
U.S. Appl. No. 14/964,239: Apr. 26, 2017 Examiner Interview Summary, 2 pages.
U.S. Appl. No. 14/964,239: Jun. 21, 2017 Nonfinal Office Action, 16 pages.
U.S. Appl. No. 14/964,239: Dec. 11, 2017 Nonfinal Office Action, 15 pages.
U.S. Appl. No. 14/964,571: Feb. 13, 2017 Nonfinal Office Action, 8 pages.
U.S. Appl. No. 14/964,571: Nov. 1, 2017 Final Office Action, 14 pages.
U.S. Appl. No. 14/964,571: Sep. 25, 2018 Nonfinal Office Action, 12 pages.
U.S. Appl. No. 14/965,140: Mar. 10, 2016 Nonfinal Office Action, 24 pages.
U.S. Appl. No. 14/965,140: Jul. 13, 2016 Interview Summary and Nonfinal Office Action, 14 pages.
U.S. Appl. No. 14/965,140: Dec. 19, 2016 Nonfinal Office Action, 9 pages.
U.S. Appl. No. 14/966,458: Dec. 6, 2016 Nonfinal Office Action, 34 pages.
U.S. Appl. No. 14/966,458: Apr. 27, 2017 Examiner Interview Summary, 2 pages.
U.S. Appl. No. 14/979,666: Dec. 9, 2016 Nonfinal Office Action, 20 pages.
U.S. Appl. No. 15/059,640: Dec. 2, 2016 Nonfinal Office Action, 9 pages.
U.S. Appl. No. 15/227,561: Jul. 14, 2017 Nonfinal Office Action, 25 pages.
U.S. Appl. No. 15/227,561: Apr. 26, 2018 Nonfinal Office Action, 13 pages.
U.S. Appl. No. 15/227,561: Dec. 10, 2018 Final Office Action, 18 pages.
U.S. Appl. No. 15/227,631: Jul. 17, 2017 Nonfinal Office Action, 24 pages.
U.S. Appl. No. 15/227,631: Apr. 10, 2018 Nonfinal Office Action, 13 pages.
U.S. Appl. No. 15/227,631: Aug. 31, 2018 Nonfinal Office Action, 15 pages.
U.S. Appl. No. 15/227,631: Dec. 19, 2018 Final Office Action, 15 pages.
U.S. Appl. No. 15/241,106: Oct. 28, 2016 Pre-Interview Communication, 4 pages.
U.S. Appl. No. 15/241,106: Dec. 29, 2016 Nonfinal Office Action, 15 pages.
Taïeb J., "FOLFIRI.3, a New Regimen Combining 5-Fluorouracil, Folinic Acid and Irinotecan, for Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec. 8, 2006.
Takahara N, et al., "Uridine Disphosphate Glucuronosyl Transferase 1 Family Polypeptide A1 Gene (UGT1A1) Polymorphisms are Associated with Toxicity and Efficacy in Irinotecan Monotherapy for Refractory Pancreatic Cancer," Cancer Chemother Pharmacol. 71(1):85-92 (2013), Epub Sep. 29, 2012.
Tanaka R, et al., "Synergistic Interaction Between Oxaliplatin and SN-38 in Human Gastric Cancer Cell Lines In Vitro," Oncol Rep. 14(3):683-8 (2005).
Tsai C, et al., "Nanovector-Based Therapies in Advanced Pancreatic Cancer," J Gastroint Oncol 2(3):185-94 (2011).
Tsubamoto H, et al., "Combination Chemotherapy with Itraconazole for Treating Metastatic Pancreatic Cancer in the Second-line or Additional Setting,". Anticancer Res. 35(7):4191-6 (2015).
Ueno H, et al., "A Phase II Study of Weekly Irinotecan as First-Line Therapy for Patients with Metastatic Pancreatic Cancer," Cancer Chemother Pharmacol. 59(4):447-54 (2007), Epub Jul. 20, 2006.
Ulrich-Pur H, et al., "Irinotecan Plus Raltitrexed vs Raltitrexed Alone in Patients with Gemcitabine-Pretreated Advanced Pancreatic Adenocarcinoma," Br J Cancer. 88(8):1180-4 (2003).

(56) References Cited

OTHER PUBLICATIONS

Umemura A, et al., "Modified FOLFIRINOX for Locally Advanced and Metastatic Pancreatic Cancer Patients Resistant to Gemcitabine and S-1 in Japan: A Single Institutional Experience," Hepato-Gastroenterology. 61:00-00 doi10.5754/hge14111, pp. 6-12 (2013).
Van Cutsem E, et al., "A Phase Ib Dose-Escalation Study of Erlotinib, Capecitabine and Oxaliplatin in Metastatic Colorectal Cancer Patients," Ann Oncol. 19(2):332-9 (2008), Epub Nov. 6, 2007.
Ventura M, et al., "Imaging-Based Assessment of the Treatment Efficacy of Nanoliposomal Irinotecan (nal-IRI) in a Triple Negative Breast Cancer Model of Spontaneous Metastasis." Poster presented at Annual World Molecular Imaging Congress, Sep. 7-10, 2016, 8 pages.
Verreault M, et al., "Vascular Normalization in Orthotopic Glioblastoma Following Intravenous Treatment with Lipid-Based Nanoparticulate Formulations of Irinotecan (Irinophore C™), Doxorubicin (Caelyx®) or Vincristine," BMC Cancer. 11:124, pp. 1-18 (2011).
Von Hoff D, et al., "NAPOLI 1: Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or following Gemcitabine-Based Therapy." Poster presented at the ESMO World Congress on Gastrointestinal Cancer 2014, 11 pages.
Wagener D, et al., "Phase II Trial of CPT-11 in Patients with Advanced Pancreatic Cancer: An EORTC Early Clinical Trials Group Study," Ann Oncol. 6(2):129-32 (1995).
Wählby C, et al., "Sequential Immunofluorescence Staining and Image Analysis for Detection of Large Numbers of Antigens in Individual Cell Nuclei," Cytometry. 47(1):32-41 (2002).
Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015).
Wasserman E, et al., "Combination of Oxaliplatin Plus Irinotecan in Patients With Gastrointestinal Tumors: Results of Two Independent Phase I Studies with Pharmacokinetics," J Clin Oncol. 17(6):1751-9 (1999).
Waterhouse D, et al., "Lipid-Based Nanoformulation of Irinotecan: Dual Mechanism of Action Allows for Combination Chemo/ Angiogenic Therapy," Nanomedicine 6(9):1645-54 (2011).
Wilson W, et al., "Targeting Hypoxia in Cancer Therapy," Nat Rev Cancer. 11(6):393-410 (2011).
Ychou, M, et al., "An Open Phase I Study Assessing the Feasibility of the Triple Combination: Oxaliplatin Plus Irinotecan Plus Leucovorin/ 5-Fluorouracil Every 2 Weeks in Patients With Advanced Solid Tumors," Ann Oncol. 14(3):481-9 (2003).
Yeh B, et al. "Structural Basis for Activation of Fibroblast Growth Factor Signaling by Sucrose Octasulfate," Mol Cell Biol. 22(20):7184-92 (2002).
Yi S, et al, "Irinotecan Monotherapy as Second-Line Treatment in Advanced Pancreatic Cancer," Cancer Chemother Pharmacol. 63(6):1141-5 (2009), Epub Oct. 7, 2008.
Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer 101(10):1658-63 (2009).
Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012).
Zeghari-Squalli, N et al., "Cellular Pharmacology of the Combination of the DNA Topoisomerase I Inhibitor SN-38 and the Deaminocyclohexane Platinum Derivative Oxaliplatin," Clin Cancer Res. 5(5):1189-96 (1999).
Zheng J, et al., "[18F]FAZA-PET Detection of Hypoxia Changes following Anti-cancer Therapy." Poster presented at Annual World Molecular Imaging Congress, Sep. 18-21, 2013, 7 pages.
Zheng J, et al., "Longitudinal Tumor Hypoxia Imaging with [18F[FAZA-PET Provides Early Prediction of Nanoliposomal Irinotecan (nal-IRI) Treatment Activity," EJNMMI Res 5(1):57, 10 pages (2015).
Clinical Trials Identifier NCT01375816: Jun. 4, 2015 update, first posted Jun. 17, 2011, "A Randomized Phase II Study of PEP02 or Irinotecan in Combination With Leucovorin and 5-Fluorouracil in Second Line Therapy of Metastatic Colorectal Cancer." Retrieved from ClinicalTrials.gov archive, 10 printed pages.
Clinical Trials Identifier NCT01446458: Oct. 4, 2011 update, "Phase I Study of Stereotactic Body Radiation Therapy and 5-Fluorouracil, Oxaliplatin and Irinotecan (FOLFIRINOX) in the Neoadjuvant Therapy of Pancreatic Cancer." Retrieved from ClinicalTrials.gov archive, 5 printed pages.
Clinical Trials Identifier NCT01494506: Dec. 16, 2011 update, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages.
Clinical Trials Identifier NCT01494506: Aug. 9, 2012 update, "A Randomized, Open Label Phase 3 Study of MM-398, With or Without 5-Fluorouracil and Leucovorin, Versus 5-Fluorouracil and Leucovorin in Patients With Metastatic Pancreatic Cancer Who Have Failed Prior Gemcitabine-based Therapy." Retrieved from ClinicalTrials.gov archive, 3 printed pages.
Clinical Trials Identifier NCT01494506: Aug. 1, 2013 update, "A Randomized, Open Label Phase 3 Study of MM-398, With or Without S~Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 3 printed pages.
Clinical Trials Identifier NCT01494506: Jun. 16, 2016 update, "A Randomized, Open Label Phase 3 Study of MM-398, With or Without 5-Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 5 printed pages.
Clinical Trials Identifier NCT01523457: Jan. 31, 2012 update, "Phase II Study of Modified FOLFIRINOX in Advanced Pancreatic Cancer." Retrieved from ClinicalTrials.gov archive, 4 printed pages.
Clinical Trials Identifier NCT01643499: Jul. 17, 2012 update, "A Genotype-guided Dosing Study of mFOLFIRINOX in Previously Untreated Patients with Advanced Gastrointestinal Malignancies." Retrieved from ClinicalTrials.gov archive, 5 printed pages.
Clinical Trials Identifier NCT01688336: Sep. 18, 2012 update, "Phase II Single Arm Clinical Trial of FOLFIRINOX for Unresectable Locally Advanced and Borderline Resectable Pancreatic Cancer." Retrieved from ClinicalTrials.gov archive, 5 printed pages.
Clinical Trials Identifier NCT01770353: Aug. 9, 2013 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 3 printed pages.
Clinical Trials Identifier NCT01770353: Apr. 26, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.
Clinical Trials Identifier NCT01770353: May 6, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.
Clinical Trials Identifier NCT01770353: Mar. 22, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.
Clinical Trials Identifier NCT01770353: Jul. 7, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages

(56) References Cited

OTHER PUBLICATIONS and to Predict Patient Response to Treatment." Retrieved from ClinicalTrials.gov archive, 4 printed pages.

Clinical Trials Identifier NCT01771146: Jan. 17, 2013 update, "A Prospective Evaluation of Neoadjuvant FOLFIRINOX Regimen in Patients with Non-metastatic Pancreas Cancer (Baylor University Medical Center and Texas Oncology Experience)." Retrieved from ClinicalTrials.gov archive, 3 printed pages.

Clinical Trials Identifier NCT01926197: Aug. 19, 2013 update, "A Randomized Phase III Study Evaluating Modified FOLFIRINOX (mFFX) With or Without Stereotactic Body Radiotherapy (SBRT) in the Treatment of Locally Advanced Pancreatic Cancer." Retrieved from ClinicalTrials.gov archive, 3 printed pages.

Clinical Trials Identifier NCT01992705: Nov. 22, 2013 update, "Neoadjuvant FOLFIRINOX and Stereotactic Body Radiotherapy (SBRT) Followed by Definitive Surgery for Patients with Borderline Resectable Pancreatic Adenocarcinoma: A Single-Arm Pilot Study." Retrieved from ClinicalTrials.gov archive, 5 printed pages.

Clinical Trials Identifier NCT02013336: Feb. 6, 2017 update, first posted Dec. 17, 2013, "Phase 1 Dose-escalating Study of MM-398 (Irinotecan Sucrosofate Liposome Injection) Plus Intravenous Cyclophosphamide in Recurrent or Refractory Pediatric Solid Tumors" Retrieved from ClinicalTrials.gov archive, 6 printed pages.

Clinical Trials Identifier NCT02022644: May 8, 2017 update, first posted Dec. 30, 2013, "A Phase I Study of Convection-Enhanced Delivery of Liposomal-Irinotecan Using Real-Time Imaging With Gadolinium in Patients With Recurrent High Grade Glioma." Retrieved from ClinicalTrials.gov archive, 9 printed pages.

Clinical Trials Identifier NCT02028806: Jan. 6, 2014 update, "Phase II Trial to Investigate the Efficacy and Safety of mFOLFIRINOX in Patients with Metastatic Pancreatic Cancer in China." Retrieved from ClinicalTrials.gov archive, 4 printed pages.

Clinical Trials Identifier NCT02047474: Jan. 27, 2014 update, "Phase II Study of Peri-Operative Modified Folfirinox in Localized Pancreatic Cancer." Retrieved from ClinicalTrials.gov archive, 5 printed pages.

Clinical Trials Identifier NCT02109341: Apr. 8, 2014 update, "Phase I/II Study to Evaluate Nab-paclitaxel in Substitution of CPT11 or Oxaliplatin in FOLFIRINOX Schedule as First Line Treatment on Metastatic Pancreatic Cancer." Retrieved from ClinicalTrials.gov archive, 5 printed pages.

Clinical Trials Identifier NCT02143219: May 20, 2014 update, "Phase-2 Study Evaluating Overall Response Rate (Efficacy) and Autonomy Daily Living Preservation (Tolerance) of 'FOLFIRINOX' Pharmacogenic Dose Adjusted, in Elderly Patients (70 yo. or Older) With a Metastatic Pancreatic Adenocarcinoma." Retrieved from ClinicalTrials.gov archive, 5 printed pages.

Clinical Trials Identifier NCT02148549: May 27, 2014 update, "The Pilot Study of Neoadjuvant Chemotherapy of FIRINOX for Patients With Borderline Resectable Pancreatic Cancer" Retrieved from ClinicalTrials.gov archive, 4 printed pages.

Clinical Trials Identifier NCT02631733: Oct. 4, 2017 update, first posted Dec. 16, 2015, "A Phase I Study of a Combination of MM-398 and Veliparib in Solid Tumors." Retrieved from ClinicalTrials.gov archive, 10 printed pages.

Clinical Trials Identifier NCT02884128: Aug. 25, 2016 update, "A Study of PEP02 in Combination With 5-fluorouracil (5-FU) and Leucovorin (LV) in Advanced Solid Tumors." Retrieved from ClinicalTrials.gov archive, 3 printed pages.

Clinical Trials Identifier NCT02884128: Aug. 30, 2016 update, first posted Aug. 30, 2016, "A Multi-Center, Open-Label Phase I Dose-Escalation Study of PEP02 in Combination With 5-fluorouracil (5-FU) and Leucovorin (LV) in Advanced Solid Tumors." Retrieved from ClinicalTrials.gov archive, 5 printed pages.

Clinical Trials Identifier NCT02896803: Sep. 11, 2016 update, "A Phase II Trial of Bolus Fluorouracil and Oxaliplatin (mFLOX) as First-line Regimen for Patients With Unresectable or Metastatic Pancreatic Cancer Not Eligible for Infusional Fluorouracil, Irinotecan and Oxaliplatin." Retrieved from ClinicalTrials.gov archive, 4 printed pages.

Clinical Trials Identifier NCT02896907: Sep. 11, 2016 update, "A Pilot Study of Intravenous Ascorbic Acid and Folfirinox in the Treatment of Advanced Pancreatic Cancer" Retrieved from ClinicalTrials.gov archive, 4 printed pages.

Conroy T, et al., "FOLFIRINOX versus Gemcitabine for Metastatic Pancreatic Cancer," N Engl J Med. 364(19):1817-25 (2011).

Conroy T, et al., "Irinotecan Plus Oxaliplatin and Leucovorin-Modulated Fluorouracil in Advanced Pancreatic Cancer—A Groupe Tumeurs Digestives of the Federation Nationale des Centres de Lutte Contre le Cancer Study," J Clin Oncol. 23(6):1228-36 (2005).

Dawidczyk C, et al., "State-of-the-art in Design Rules for Drug Delivery Platforms: Lessons Learned from FDA-Approved Nanomedicines," J Control Release. 187:133-44 (2014).

Dean A, et al., "A Phase 2, Open-Label Dose-Exploration Study of Liposomal Irinotecan (nal-IRI) Plus 5-Flurouracil/Leucovorin (5-FU/LV) plus Oxaliplatin (OX) in Patients With Previously Untreated Metastatic Pancreatic Cancer." Poster presented at the American Society of Clinical Oncology Annual Conference, Chicago, IL, Jun. 1-5, 2018, 11 pages.

Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster presented at the Gastrointestinal Cancers Symposium ASCO 2016, 11 pages.

Delord J, et al., "Population Pharmacokinetics of Oxaliplatin," Cancer Chemother Pharmacol. 51(2):127-31 (2003), Epub Dec. 4, 2002.

Dickinson P, et al., "Canine Model of Convection-Enhanced Delivery of Liposomes Containing CPT-11 Monitored with Real-Time Magnetic Resonance Imaging," J. Neurosurg. 108(5):989-98 (2008).

Dickinson P, et al., "Canine Spontaneous Glioma: A Translational Model System for Convection-Enhanced Delivery," Neuro Oncol. 12(9):928-40; Epub 10:1093/neuonc/noq046, 1-13 (2010).

Dósa E, et al., "Magnetic Resonance Imaging of Intracranial Tumors: Intra-Patient Comparison of Gadoteridol and Ferumoxytol," Neuro Oncol. 13(2):251-60 (2011) doi: 10.1093/neuonc/noq172. Epub 2010.

DOXIL package insert, revision Apr. 16, 2015, retrieved from https://www.accessdata.fda.gov/drugsatfda_docs/label/2015/050718s048lbl.pdf, 28 pages.

DOXIL package insert, revision Aug. 30, 2013, retrieved from https://www.accessdata.fda.gov/drugsatfda_docs/label/2013/050718s045lbl.pdf, 35 pages.

DOXIL package insert, revision Jun. 10, 2008, retrieved from https://www.accessdata.fda.gov/drugsatfda_docs/label/2008/050718s033lbl.pdf, 34 pages.

Drummond D, et al., "Development of a Highly Active Nanoliposomal Irinotecan Using a Novel Intraliposomal Stabilization Strategy," Cancer Res. 66(6):3271-77 (2006).

Drummond D, et al., "Optimizing Liposomes for Delivery of Chemotherapeutic Agents to Solid Tumors," Pharmacol Rev. 51(4):691-743 (1999).

Ducreax M, et al., "Randomized Phase II Study Evaluating Oxaliplatin Alone, Oxaliplatin Combined with Infusional 5-FU, and Infusional 5-FU Alone in Advanced Pancreatic Carcinoma Patients," Ann Oncol. 15(3): 467-73 (2004).

Eisenhauer E, et al., "New Response Evaluation Criteria in Solid Tumours: Revised Recist Guideline (version 1.1)," Eur J Cancer 45(2):228-47 (2009).

ELOXATIN package insert, revision Dec. 28, 2011, retrieved from https://www.accessdata.fda.gov/drugsatfda_docs/label/2011/021492s012lbl.pdf, 51 pages.

EP2861210: Communication of Notices of Opposition (R. 79(1) EPC), dated Feb. 16, 2018, 1 page.

EP2861210: Notice of Opposition dated Feb. 5, 2018, 6 pages.

EP2861210: Opposition dated Feb. 5, 2018, Annex to Notice of Opposition, Facts and Arguments, 8 pages.

EP2861210: Opposition dated Feb. 5, 2018, D1 (FUSILEV package insert, 2008, 7 pages).

EP2861210: Opposition dated Feb. 5, 2018, D2 (Gebbia V, et al., "Irinotecan Plus Bolus/Infusional 5-Fluorouracil and Leucovorin in Patients With Pretreated Advanced Pancreatic Carcinoma: A Mul-

(56) References Cited

OTHER PUBLICATIONS ticenter Experience of the Gruppo Oncologico Italia Meridionale," Am J Clin Oncol. 33(5):461-64 (2010)).
EP2861210: Opposition dated Feb. 5, 2018, D3 (Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012)).
EP2861210: Opposition dated Feb. 5, 2018, D4 (Neuzillet C, et al., "Folfiri Regimen in Metastatic Pancreatic Adenocarcinoma Resistant to Gemcitabine and Platinum-Salts," World J Gastroenterol. 18(33):4533-41 (2012)).
EP2861210: Opposition dated Feb. 5, 2018, D5 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009)).
EP2861210: Opposition dated Feb. 5, 2018, D6 (Taïeb J., "FOLFIRI. 3, a New Regimen Combining 5-Fluorouracil, Folinic Acid and Irinotecan, for Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec. 8, 2006).
EP2861210: Opposition dated Feb. 5, 2018, D7 (Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 2 pages).
EP2861210: Opposition dated Feb. 5, 2018, D8 (Infante J, et al., "Phase I and Pharmacokinetic Study of IHL-305 (PEGylated Liposomal Irinotecan) in Patients With Advanced Solid Tumors," Cancer Chemother Pharmacol. 70(5): 699-705 (2012)).
EP2861210: Opposition dated Feb. 5, 2018, D9 (Waterhouse D, et al., "Lipid-Based Nanoformulation of Irinotecan: Dual Mechanism of Action Allows for Combination Chemo/Angiogenic Therapy," Nanomedicine 6(9):1645-54 (2011)).
EP2861210: Opposition filed Feb. 5, 2018, D10 (CAMPTOSAR package insert, 2012, 39 pages).
EP2861210: Opposition filed Feb. 5, 2018, D11 (Hoskins J, et al., "UGT1A1*28 Genotype and Irinotecan-Induced Neutropenia: Dose Matters," J Natl Cancer Inst. 99(17):1290-95 (2007)).
EP2861210: Opposition dated Feb. 5, 2018, D12 (Tsai C, et al., "Nanovector-Based Therapies in Advanced Pancreatic Cancer," J Gastroint Oncol 2(3):185-94 (2011)).
EP2861210: Opposition dated Feb. 5, 2018, D13 (Ko A, et al., "A Multinational Phase II Study of Liposome Irinotecan (PEP02) for Patients with Gemcitabine-Refractory Metastatic Pancreatic Cancer," J Clin Oncol. 29:2011 (Suppl; Abstract 237). 2011 ASCO Annual Meeting (2011), 2 printed pages).
EP2861210: Opposition dated Feb. 5, 2018, D15 (Clinical Trials Identifier NCT01494506: Jan. 25, 2013 version, "A Randomized, Open Label Phase 3 Study of MM-398, With or Without 5-Fluorouracil and Leucovorin, Versus 5 Fluorouracil and Leucovorin in Patients With Metastatic Pancreatic Cancer Who Have Failed Prior Gemcitabine-based Therapy," Retrieved from ClinicalTrials.gov archive, 1 printed page).
EP2861210: Response to EP Opposition Proceedings filed Aug. 24, 2018, 22 pages.
EP2861210: Response to EP Opposition Proceedings filed Aug. 24, 2018, D15a (Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages).
EP2861210: Response to EP Opposition Proceedings filed Aug. 24, 2018, D17 (European Commission Implementing Decision granting marketing authorisation for Onivyde, Oct. 14, 2016), 39 pages.
EP2861210: Response to EP Opposition Proceedings filed Aug. 24, 2018, D18 (FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages).
EP2861210: Response to EP Opposition Proceedings filed Aug. 24, 2018, D19 (Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1 pp. 1-13 (2015)).
EP2861210: Response to EP Opposition Proceedings filed Aug. 24, 2018, D20 (MHRA Public Assessment Report for 5-Fluorouracil, 2006, 60 pages).
Extra J, et al., "Phase I Study of Oxaliplatin in Patients with Advanced Cancer," Cancer Chemother Pharmacol. 25(4):299-303 (1990).
FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages.
Fischel J, et al., "Ternary Combination of Irinotecan, Fluorouracil-Folinic Acid and Oxaliplatin: Results on Human Colon Cancer Cell Lines," Br J Cancer. 84(4):579-85 (2001).
Fitzgerald J, et al., "Systems Pharmacology Identification of Tumour Nanoparticle Permeability as Predictor of Clinical Anti-Cancer Activity of MM-398, Nanoliposomal Irinotecan, nal-IRI." Poster presented at 15th International Conference on Systems Biology. Sep. 14-18, 2014, 10 pages.
Fleming D. "Importance of sequence in chemotherapy administration," retrieved from http://www.oncologynurseadvisor.com/advisor-forum/importance-of-sequence-in-chemotherapy-administration/article/378072/ (2014).
Fuchs C, et al., "Phase III Comparison of Two Irinotecan Dosing Regimens in Second-Line Therapy of Metastatic Colorectal Cancer," J Clin Oncol. 21(5):807-14 (2003).
Gaddy D, et al., "Preclinical Anti-tumor Activity of Nanoliposomal Irinotecan (nal-IRI, MM-398) + 5-FU + Oxaliplatin in Pancreatic Cancer." Poster presented at AACR 2016, 5 pages.
Gaddy D., "Preclinical Anti-tumor Activity of Nanoliposomal Irinotecan (Nal-IRI, MM-398) + 5-FU + Oxaliplatin in Pancreatic Cancer." Abstract presented at AACR 2016, 1 page.
Gahramanov S, et al., "Pseudoprogression of Glioblastoma After Chemo- and Radiation Therapy: Diagnosis by Using Dynamic Susceptibility-Weighted Contrast-Enhanced Perfusion MR Imaging with Ferumoxytol versus Gadoteridol and Correlation with Survival," Radiology. 266(3):842-52 (2013). doi: 10.1148/radiol.12111472. Epub Nov. 30, 2012.
Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010).
GEMZAR package insert, revision Feb. 4, 2011, retrieved from https://www.accessdata.fda.gov/drugsatfda_docs/label/2011/020509s069lbl.pdf, 21 pages.
GEMZAR package insert, revision May 8, 2014, retrieved from https://www.accessdata.fda.gov/drugsatfda_docs/label/2014/020509s077lbl.pdf, 18 pages.
GLOBOCAN Cancer Facts Sheets: All Cancers 2012. Available from: http://globocan.iarc.fr/old/FactSheets/cancers/all-new.asp, accessed on Oct. 3, 2016, 9 printed pages.
Goldstein D, et al., "nab-Paclitaxel Plus Gemcitabine for Metastatic Pancreatic Cancer: Long-Term Survival From a Phase III Trial," J Natl Cancer Inst. 107(2): dju413, pp. 1-10 (2015).
Grant S, et al., "Dose-Ranging Evaluation of the Substituted Benzamide Dazopride When Used as an Antiemetic in Patients Receiving Anticancer Chemotherapy," Cancer Chemother Pharmacol. 31(6):442-44 (1993).
Guichard S, et al., "Combination of Oxaliplatin and Irinotecan on Human Colon Cancer Cell Lines: Activity In Vitro and In Vivo," Anticancer Drugs. 12(9):741-51 (2001).
Hayashi H, et al., "Phase II Study of Bi-Weekly Irinotecan for Patients with Previously Treated HER2-Negative Metastatic Breast Cancer: KMBOG0610B," Breast Cancer. 20(2):131-6 (2013); doi: 10.1007/s12282-011-0316-z. Epub Nov. 29, 2011.

(56) References Cited

OTHER PUBLICATIONS

Hayes M, et al., "Assembly of Nucleic Acid-Lipid Nanoparticles from Aqueous-Organic Monophases," Biochim Biophys Acta. 1758(4):429-42 (2006).
Hong K, et al., "Anti-HER2 Immunoliposomes for Targeted Drug Delivery," Ann N Y Acad Sci. 886:293-6 (1999).
Hosein P, et al., "A Retrospective Study of Neoadjuvant FOLFIRINOX in Unresectable or Borderline-Resectable Locally Advanced Adenocarcinoma," BMC Cancer. 12:199, pp. 1-7 (2012).
Hoskins J, et al., "UGT1A1*28 Genotype and Irinotecan-Induced Neutropenia: Dose Matters," J Natl Cancer Inst. 99(17):1290-95 (2007).
Infante J, et al., "Phase I and Pharmacokinetic Study of IHL-305 (PEGylated Liposomal Irinotecan) in Patients with Advanced Solid Tumors," Cancer Chemother Pharmacol. 70(5):699-705 (2012).
Jacobs A, et al., "A Randomized Phase III Study of Rubitecan (ORA) vs. Best Choice (BC) in 409 Patients with Refractory Pancreatic Cancer Report from a North-American Multi-Center Study," J Clin Oncol., 2004 ASCO Annual Meeting Proceedings 22(14S):4013 (2004).
Kalra A, et al., "Preclinical Activity of Nanoliposomal Irinotecan Is Governed by Tumor Deposition and Intratumor Prodrug Conversion," Cancer Res. Author queries on manuscript, pp. 1-11 (2014), 13 total pages.
Kalra A, et al., Abstract 2065: "Magnetic Resonance Imaging with an Iron Oxide Nanoparticle Demonstrates Preclinically the Feasibility of Predicting Intratumoral Uptake and Activity of MM-398, a Nanoliposomal Irinotecan (nal-IRI)." Poster presented at American Association for Cancer Research annual meeting 2014, San Diego, CA, 5 pages.
Kalra A., "Magnetic Resonance Imaging (MRI) to Predict Tumor Drug Delivery and Response to Nanoliposomal Therapy." Presentation presented at Tumor Models Boston 2014, 32 pages.
Kambe M, et al., "Phase I Study of Irinotecan by 24-h Intravenous Infusion in Combination with 5-Fluorouracil in Metastatic Colorectal Cancer," Int J Clin Oncol. 17(2):150-4 (2012).
Kang M, et al., "Activity of MM-398, Nanoliposomal Irinotecan (nal-IRI), in Ewing's Family Tumor Xenografts Is Associated with High Exposure of Tumor to Drug and High SLFN11 Expression," Clin Cancer Res. 21(5):1139-50 (2015).
Katsu T, et al., "Ion-Selective Electrode for Transmembrane pH Difference Measurements," Anal. Chem. 73(8):1849-54 (2001).
Kim J, et al., "Sustained Intratumoral Activation of MM-398 Results in Superior Activity over Irinotecan Demonstrated by Using a Systems Pharmacology Approach." Poster presented at the AACR Pancreatic Cancer Symposium, Jun. 18-21, 2012, New York, New York, 8 pages.
Kim J, et. al., "Systems Pharmacology Based Biomarker Potentially Predicts Clinical Anti-Cancer Activity of MM-398, Nanoliposomal Irinotecan, nal-IRI." Poster presented at American Conference on Pharmacometrics, Oct. 12-15, 2014, 10 pages.
Kirpotin D, et al. "Antibody Targeting of Long-Circulating Lipidic Nanoparticles Does Not Increase Tumor Locatlization but Does Increase Internalization in Animal Models," Cancer Res. 66(13):6732-40 (2006).
Korn R, "Advanced Imaging with Ferumoxytol MRI to Predict Drug Delivery." Presentation presented at Pancreatic Cancer 2014, Feb. 22, 2014, 23 pages.
Lordick F, et al., "Phase II Study of Weekly Oxaliplatin Plus Infusional Fluorouracil and Folinic Acid (FUFOX Regiment) as First-Line Treatment in Metastatic Gastric Cancer," Br J Cancer 93(2)190-4 (2005).
U.S. Appl. No. 11/121,294, filed May 2, 2005, U.S. Pat. No. 8,147,867, Issued.
U.S. Appl. No. 11/601,451, filed Nov. 17, 2006, U.S. Pat. No. 8,658,203, Issued.
U.S. Appl. No. 13/416,204, filed Mar. 9, 2012, U.S. Pat. No. 8,329,213, Issued.
U.S. Appl. No. 13/654,373, filed Oct. 17, 2012, U.S. Pat. No. 8,703,181, Issued.
U.S. Appl. No. 14/151,632, filed Jan. 9, 2014, Abandoned.
U.S. Appl. No. 14/175,365, filed Feb. 7, 2014, U.S. Pat. No. 8,992,970, Issued.
U.S. Appl. No. 14/632,422, filed Feb. 26, 2015, U.S. Pat. No. 9,717,723, Issued.
U.S. Appl. No. 14/879,302, filed Oct. 9, 2015, U.S. Pat. No. 9,730,891, Issued.
U.S. Appl. No. 14/879,358, filed Oct. 9, 2015, Abandoned.
U.S. Appl. No. 14/964,239, filed Dec. 9, 2015, Abandoned.
U.S. Appl. No. 14/965,140, filed Dec. 10, 2015, U.S. Pat. No. 9,724,303, Issued.
U.S. Appl. No. 14/966,458, filed Dec. 11, 2015, U.S. Pat. No. 9,782,349, Issued.
U.S. Appl. No. 14/979,666, filed Dec. 28, 2015, Abandoned.
U.S. Appl. No. 15/227,561, filed Aug. 3, 2016, Published.
U.S. Appl. No. 15/227,631, filed Aug. 3, 2016, Published.
U.S. Appl. No. 15/213,127, filed Jul. 18, 2016, Abandoned.
U.S. Appl. No. 15/296,536, filed Oct. 18, 2016, U.S. Pat. No. 9,737,528, Issued.
U.S. Appl. No. 15/363,761, filed Nov. 29, 2016, Published.
U.S. Appl. No. 15/363,923, filed Nov. 29, 2016, Abandoned.
U.S. Appl. No. 15/363,978, filed Nov. 29, 2016, Published.
U.S. Appl. No. 15/364,021, filed Nov. 29, 2016, Abandoned.
U.S. Appl. No. 15/664,976, filed Jul. 31, 2017, Published.
U.S. Appl. No. 15/896,389, filed Feb. 14, 2018, Published.
U.S. Appl. No. 15/896,436, filed Feb. 14, 2018, Published.
U.S. Appl. No. 14/406,776, filed Dec. 10, 2014, U.S. Pat. No. 9,452,162, Issued.
U.S. Appl. No. 14/812,950, filed Jul. 29, 2015, U.S. Pat. No. 9,339,497, Issued.
U.S. Appl. No. 14/844,500, filed Sep. 3, 2015, U.S. Pat. No. 9,364,473, Issued.
U.S. Appl. No. 14/851,111, filed Sep. 11, 2015, U.S. Pat. No. 9,492,442, Issued.
U.S. Appl. No. 15/059,640, filed Mar. 3, 2016, Abandoned.
U.S. Appl. No. 15/241,128, filed Aug. 19, 2016, U.S. Pat. No. 9,717,724, Issued.
U.S. Appl. No. 15/341,377, filed Nov. 2, 2016, Abandoned.
U.S. Appl. No. 15/341,619, filed Nov. 2, 2016, Abandoned.
U.S. Appl. No. 15/652,513, filed Jul. 18, 2017, Abandoned.
U.S. Appl. No. 15/664,930, filed Jul. 31, 2017, Abandoned.
U.S. Appl. No. 16/012,351, filed Jun. 19, 2018, Published.
U.S. Appl. No. 16/012,372, filed Jun. 19, 2018, Published.
U.S. Appl. No. 14/964,571, filed Dec. 9, 2015, Published.
U.S. Appl. No. 15/375,039, filed Dec. 9, 2016, Abandoned.
U.S. Appl. No. 15/928,649, filed Mar. 22, 2018, Abandoned.
U.S. Appl. No. 16/036,885, filed Jul. 16, 2018, Pending.
U.S. Appl. No. 15/337,274, filed Oct. 28, 2016, U.S. Pat. No. 9,895,365, Issued.
U.S. Appl. No. 15/241,106, filed Aug. 19, 2016, Abandoned.
U.S. Appl. No. 15/809,815, filed Nov. 10, 2017, Published.
U.S. Appl. No. 15/403,441, filed Jan. 11, 2017, Abandoned.
U.S. Appl. No. 15/331,648, filed Oct. 21, 2016, Abandoned.
U.S. Appl. No. 15/331,393, filed Oct. 21, 2016, Abandoned.
U.S. Appl. No. 15/331,318, filed Oct. 21, 2016, Abandoned.
U.S. Appl. No. 15/645,645, filed Jul. 10, 2017, Abandoned.
U.S. Appl. No. 15/655,592, filed Jul. 20, 2017, Abandoned.
U.S. Appl. No. 15/661,868, filed Jul. 27, 2017, Abandoned.
U.S. Appl. No. 15/908,443, filed Feb. 28, 2018, Abandoned.
U.S. Appl. No. 15/768,352, filed Apr. 13, 2018, Published.
U.S. Appl. No. 15/967,633, filed May 1, 2018, Abandoned.
U.S. Appl. No. 15/967,638, filed May 1, 2018, Published.
U.S. Appl. No. 15/598,633, filed May 18, 2017, Abandoned.
U.S. Appl. No. 15/948,571, filed Apr. 9, 2018, Abandoned.
U.S. Appl. No. 16/302,050, filed Nov. 15, 2018, Pending.
U.S. Appl. No. 16/346,436, filed Apr. 30, 2019, Pending.
Clinical Trials Identifier NCT01359007: May 28, 2015 update, "A Phase II Study Evaluating the Rate of R0 Resection (Microscopically Negative Margins) After Induction Therapy With 5-Fluorouracil, Leucovorin, Oxaliplatln, Irinotecan (FOLFIRINOX) in Patients With Borderline Resectable or Locally Advanced Inoperable Pancreatic Cancer." Retrieved from ClinicalTrials.gov archive, 3 printed pages.

(56) References Cited

OTHER PUBLICATIONS

Clinical Trials Identifier NCT01375816: Jun. 16, 2011 update, "A Randomized Phase II Study of PEP02 or Irinotecan in Combination With Leucovorin and 5-Flourouracil in Second Line Therapy of Metastatic Colorectal Cancer." Retrieved from ClinicalTrials.gov archive, 5 printed pages.

ME-180 cells viability (1000cells/well in 384-well plate) treated with SN-38 and with different PARP inhibitors (0.33 ug/ml) for 24hrs, washed and incubated for additional 72hrs with fresh media MS-751 cells viability (1000cells/well in 384-well plate) treated with SN-38 and with different PARP inhibitors (0.33 ug/ml) for 24hrs, washed and incubated for additional 72hrs with fresh media SW756 cells viability (1000cells/well in 384-well plate) treated with SN-38 and with different PARP inhibitors (0.33 ug/ml) for 24hrs, washed and incubated for additional 72hrs with fresh media BT20 cell survival treated with SN-38 and Talazoparib HCC38 cell survival treated with SN-38 and Talazoparib

| Dose Escalation Cohorts | | | |
|---|---|---|---|
| Dose Level | Veliparib Dose (mg BID) | Veliparib Start Day | nal-IRI Dose (salt) (mg/m$^2$ q2w) |
| 1 | 100 | Day 5 | 80 |
| 2 | 200 | Day 5 | 80 |
| 3 | 200 | Day 3 | 80 |
| 4 | 300 | Day 3 | 80 |
| 5 | 400 | Day 3 | 80 |

COMBINATION THERAPY FOR CANCER TREATMENT

CROSS-REFERENCE OF RELATED APPLICATIONS

This application is a continuation of U.S. Application No. 15/337,274, filed Oct. 28, 2016, which is a continuation of PCT Application No. PCT/US2016/047827, filed on Aug. 19, 2016, which claims the benefit of priority under 35 U.S.C. § 119 to United States Provisional Application Serial No(s). 62/323,422, filed on Apr. 15, 2016, 62/308,924, filed on Mar. 16, 2016, 62/269,511, filed on Dec. 18, 2015, 62/269,756, filed on Dec. 18, 2015, 62/207,709, filed on Aug. 20, 2015, and 62/207,760, filed on Aug. 20, 2015. The contents of each of the foregoing applications are incorporated herein by reference in their entirety.

TECHNICAL FIELD

This invention relates to the treatment of cancer with a Poly(ADP-ribose) polymerase (PARP) inhibitor and a topoisomerase inhibitor.

BACKGROUND

Liposomal irinotecan and PARP inhibitors are therapies useful in the treatment of cancer. Liposome encapsulated irinotecan formulations of the topoisomerase inhibitor irinotecan provide sustained exposure of irinotecan and the metabolite SN-38 in a tumor. ONIVYDE (irinotecan liposome injection) is an example of liposomal irinotecan recently approved in the United States for the treatment of patients with metastatic adenocarcinoma of the pancreas after disease progression following gemcitabine-based therapy. Poly(ADP-ribose) polymerases are a family of enzymes involved in DNA repair believed to act via two mechanisms: catalytic inhibition and trapping of PARP-DNA complexes, and inhibition of this repair pathway can result in cell death following DNA damage. PARP inhibitors are a new class of chemotherapeutic agents currently in development for the treatment of various cancer types.

While certain combinations of PARP and topoisomerase inhibitors have shown to be synergistic in in vitro assays, the clinical development of PARP inhibitor and topoisomerase inhibitor combinations has been limited due to increased toxicities and resultant dose reductions, thereby limiting the potential clinical utility of the combination. For example, significant myelosuppression was seen in a dose-escalation study of veliparib and topotecan, wherein the maximum tolerated dose was exceeded at the first planned dose level. Most PARP inhibitors are being developed to date solely as monotherapies. As a result, there is a need for methods to safely and effectively combine a PARP inhibitor with a Top1 inhibitor to treat cancer.

SUMMARY

The present disclosure provides methods of treating cancer by administering a topoisomerase inhibitor and a PARP inhibitor with reduced peripheral toxicity. This can be accomplished by administering the topoisomerase inhibitor in a form (e.g., liposomal irinotecan) that prolongs accumulation of the topoisomerase inhibitor in a tumor relative to sites outside the tumor, and then subsequently administering the PARP inhibitor(s) to the patient after an interval between the administration of the topoisomerase inhibitor and the PARP inhibitor. The interval can be selected to provide enough time for the topoisomerase inhibitor (e.g., irinotecan and/or its metabolite SN-38) to clear plasma or tissue outside of the tumor to a greater extent than inside the tumor. Preferably, the interval is an effective topoisomerase-1 inhibitor plasma clearing interval. As used herein, the term “effective topoisomerase-1 inhibitor plasma clearing interval” (e.g., irinotecan plasma clearing interval) is that interval between concluding the administration of a topoisomerase-1 inhibitor formulation (e.g., liposomal irinotecan) and initiating the administration of one or more PARP inhibitors, where the time interval is selected to allow sufficient clearance of the topoisomerase-1 inhibitor (e.g., irinotecan or its active metabolite SN-38) from the blood plasma (or peripheral tissue) but allows an effective quantity of the topoisomerase-1 inhibitor (e.g., irinotecan and/or SN38) to remain in one or more tumors within the patient during the subsequent administration of the PARP inhibitor in an amount effective to provide a desired effect on the tumor (e.g., heightened combined toxicity localized within the tumor). Preferably, she PARP inhibitor is administered after an irinotecan plasma clearing interval of 3-5 days (e.g., 3, 4 or 5 days) after completing the administration of liposomal irinotecan on days 1 and 15 during each of one or more 28-day treatment cycles.

Methods of treating cancer disclosed herein include the treatment of solid tumors. In certain examples, the cancer treated can be selected from the group consisting of cervical cancer, ovarian cancer, triple negative breast cancer, non-small cell lung cancer, small cell lung cancer, gastrointestinal stromal tumors gastric cancer, pancreatic cancer, colorectal cancer, and a neuroendocrine cancer. Preferably, the cancer is cervical cancer.

The topoisomerase inhibitor can be provided as a liposome formulation. Preferably, the topoisomerase inhibitor is a liposomal irinotecan. The liposomal irinotecan can provide an irinotecan terminal elimination half-life of 26.8 hours and a maximal irinotecan plasma concentration of 38.0 micrograms/ml. In some examples, the liposomal irinotecan can include irinotecan sucrose octasulfate encapsulated within phospholipid vesicles having a size of about 110 nm. For example, the liposomal irinotecan can be the product ONIVYDE® (irinotecan liposome injection) (Merrimack Pharmaceuticals, Inc. Cambridge, Mass.), previously designated “MM-398.” The PARP inhibitor can include one or more compounds selected from the group consisting of niraparib, olaparib, veliparib, and rucaparib, preferably veliparib or olaparib.

The topoisomerase-1 inhibitor is preferably a liposomal irinotecan (e.g., MM-398), which can be administered at dose of 80 $mg/m^2$ (salt) irinotecan once every 2 weeks in combination with a PARP inhibitor (e.g., veliparib, olaparib. niraparib or rucaparib) administered daily during each two week cycle starting 3-5 days after administration of liposomal irinotecan without administering the PARP inhibitor on days when the liposomal irinotecan is administered (e.g., without administering the PARP inhibitor 1, 2 or 3 days before the next liposomal irinotecan administration). Preferably, the PARP inhibitor is not administered within 3 days of (i.e., neither 3 days after nor 3 days before) the administration of liposomal irinotecan.

Specific methods of treating a cancer provided herein include administering an antineoplastic therapy consisting of the administration of liposomal irinotecan every 2 weeks (e.g., on days 1 and 15 of a 28-day treatment cycle), and the administration of a PARP inhibitor one or more times per day (e.g., twice per day) for one or more days (e.g., 7-9 days)

starting at least 3 days (e.g., 3, 4 or 5 days) after each administration of the liposomal irinotecan, without administering other antineoplastic agents during the antineoplastic therapy. For example, one antineoplastic therapy is a 28-day treatment cycle consisting of: administering 70 mg/$m^2$ MM-398 liposomal irinotecan (free base) on days 1 and 15, and administering a therapeutically effective amount of the PARP inhibitor (e.g., 50-400 mg twice per day for veliparib) on each of days 5-12 and days 19-25 of the treatment cycle, where no other antineoplastic agent is administered during the treatment cycle. Another antineoplastic therapy is a 28-day treatment cycle consisting of: administering 70 mg/$m^2$ MM-398 liposomal irinotecan (free base) on days 1 and 15, and administering a therapeutically effective amount of the PARP inhibitor (e.g., 50-400 mg twice per day for veliparib) on each of days 3-12 and days 17-25 of the treatment cycle, where no other antineoplastic agent is administered during the treatment cycle.

In some examples, liposomal irinotecan and a PARP inhibitor can be combined in an antineoplastic therapy for the treatment of a solid tumor, comprising a 28-day antineoplastic therapy treatment cycle consisting of: administering the liposomal irinotecan on days 1 and 15 of the treatment cycle, and administering the PARP inhibitor on one or more days starting at least 3 days after the liposomal irinotecan and ending at least 1 day prior to administration of additional liposomal irinotecan. In some examples, the PARP inhibitor is not administered for at least 3 days after the administration of liposomal irinotecan. For example, the PARP inhibitor can be administered on one or more of days 5-12 of she antineoplastic therapy treatment cycle, and administered on one or more of days 19-25 of the antineoplastic therapy treatment cycle. In some examples, the PARP inhibitor is administered on one or more of days 3-12 of the antineoplastic therapy treatment cycle, and administered on one or more of days 17-25 of the antineoplastic therapy treatment cycle. In some examples, the PARP inhibitor is not administered within 3 days before or after the administration of the liposomal irinotecan.

In addition, therapeutically effective doses of the topoisomerase inhibitor and PARP inhibitor compounds are provided herein. In some examples, each administration of liposomal irinotecan is administered at a dose of 80 mg/$m^2$ (salt) of MM-398. In some examples, each administration of the PARP inhibitor is administered at a dose of from about 20 mg/day to about 800 mg/day. Each administration of the PARP inhibitor can be administered once or twice daily at a dose of from about 20 mg/day to about 400 mg/day.

BRIEF DESCRIPTION OF THE DRAWINGS

FIG. 17 outlines two different schedules of veliparib dosing that will be explored in combination with MM-398 bi-weekly dosing.

DETAILED DESCRIPTION

Figure 1A:
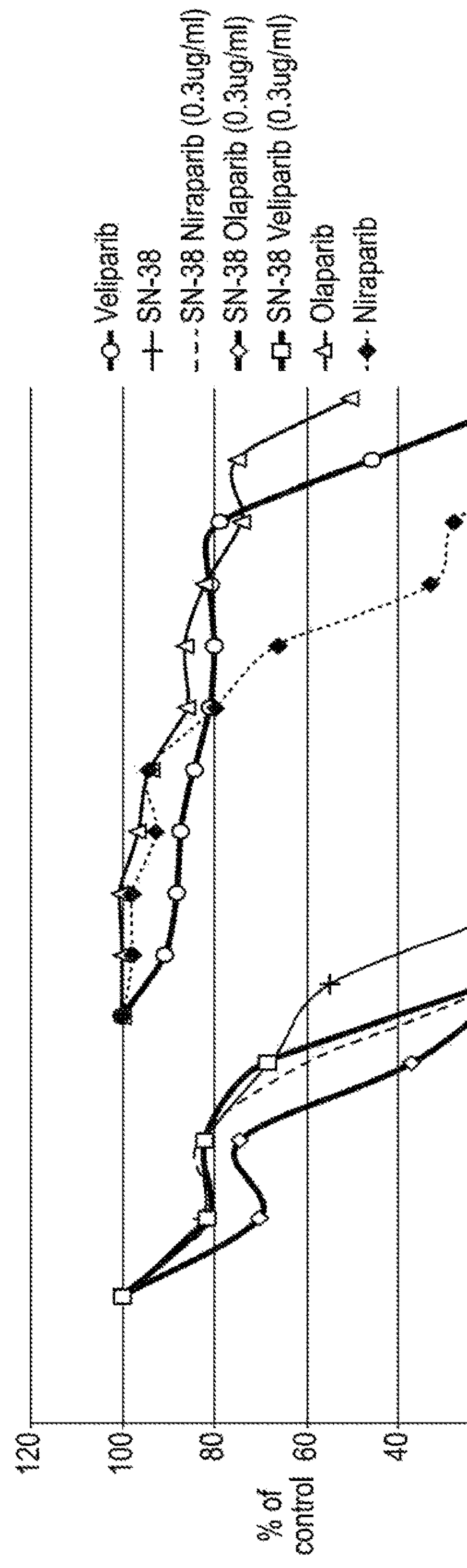
FIG. 1A is a graph showing the results of a cell viability in vitro measurement of ME-180 human cervical cancer cells treated with the topoisomerase 1 inhibitor SN-38 and various PARP inhibitors.
Figure 1B:
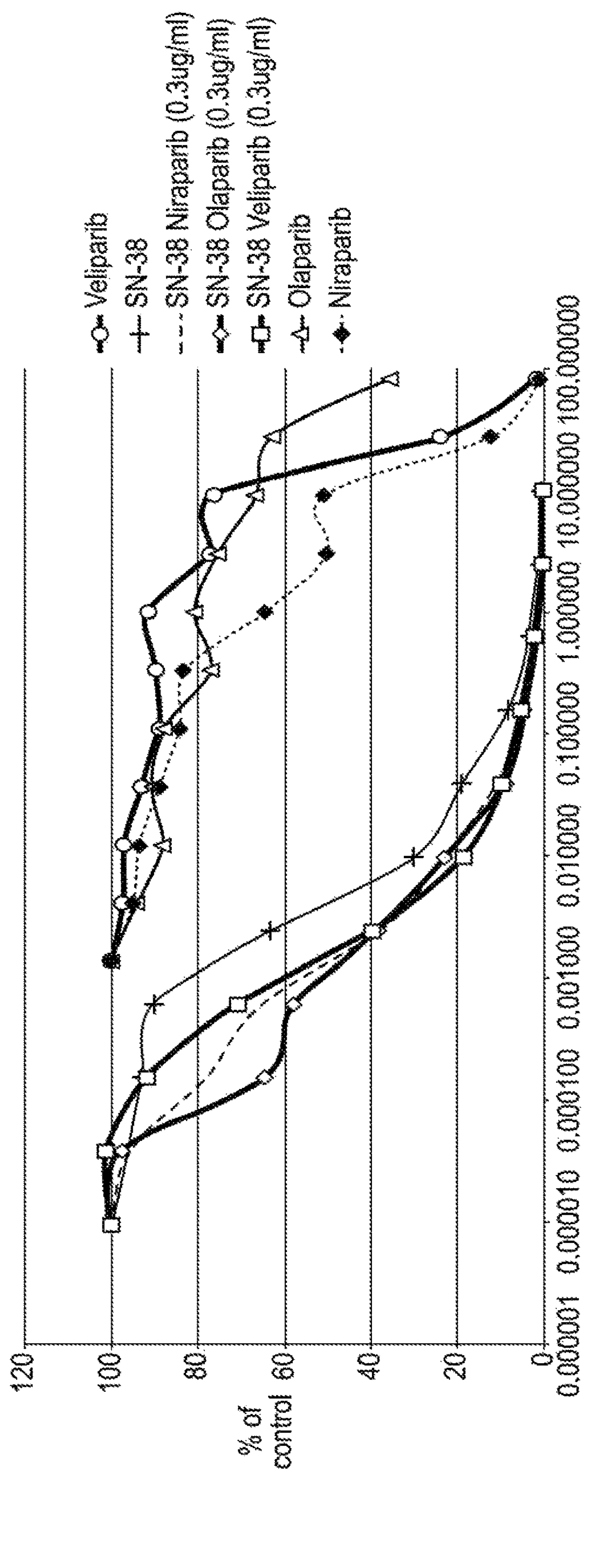
FIG. 1B is a graph showing the results of a cell viability in vitro measurement of MS-751 human cervical cancer cells treated with the topoisomerase 1 inhibitor SN-38 and various PARP inhibitors.
Figure 1C:
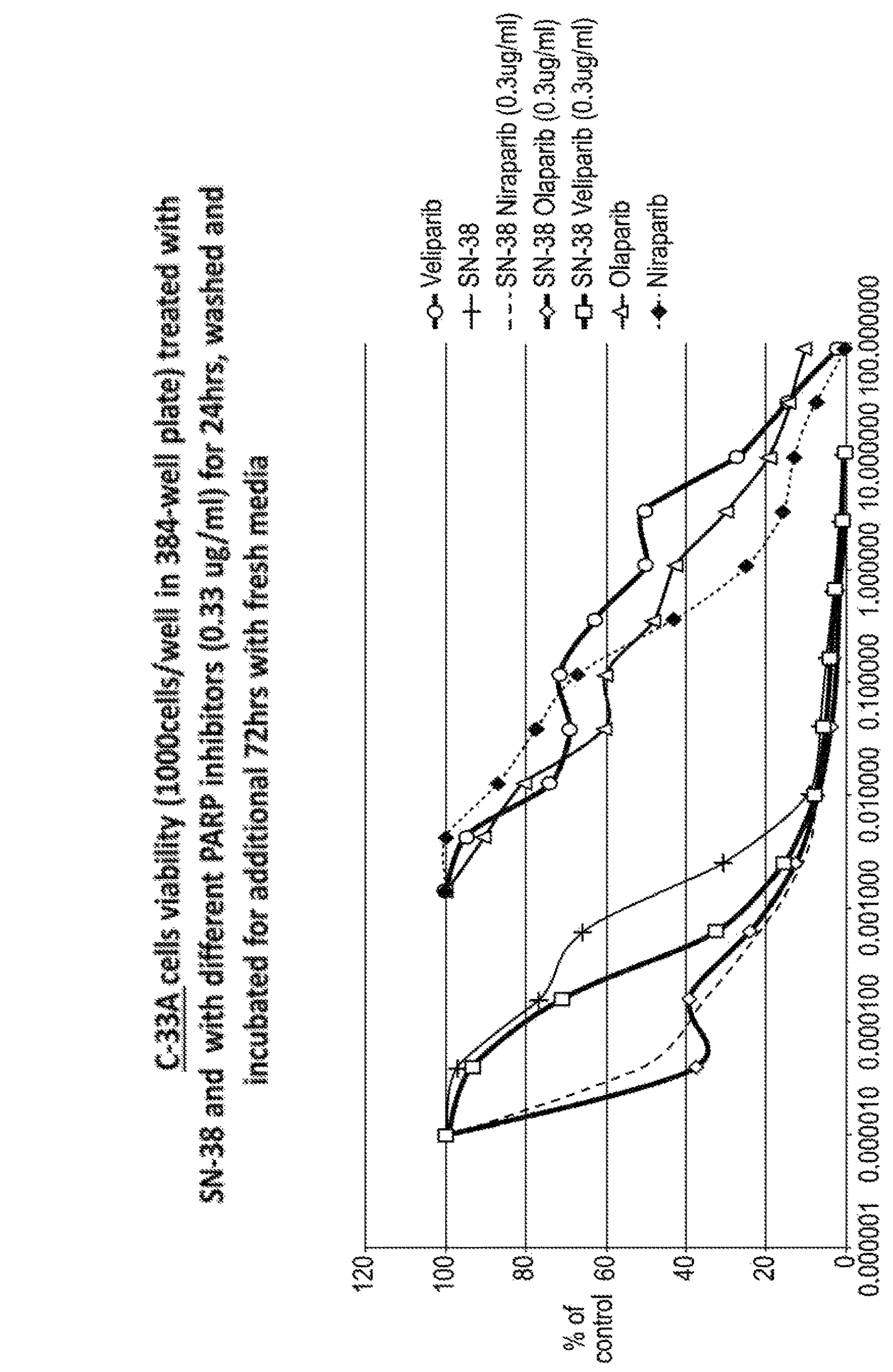
FIG. 1C is a graph showing the results of a cell viability in vitro measurement of C-33A human cervical cancer cells treated with the topoisomerase 1 inhibitor SN-38 and various PARP inhibitors.
Figure 1D:
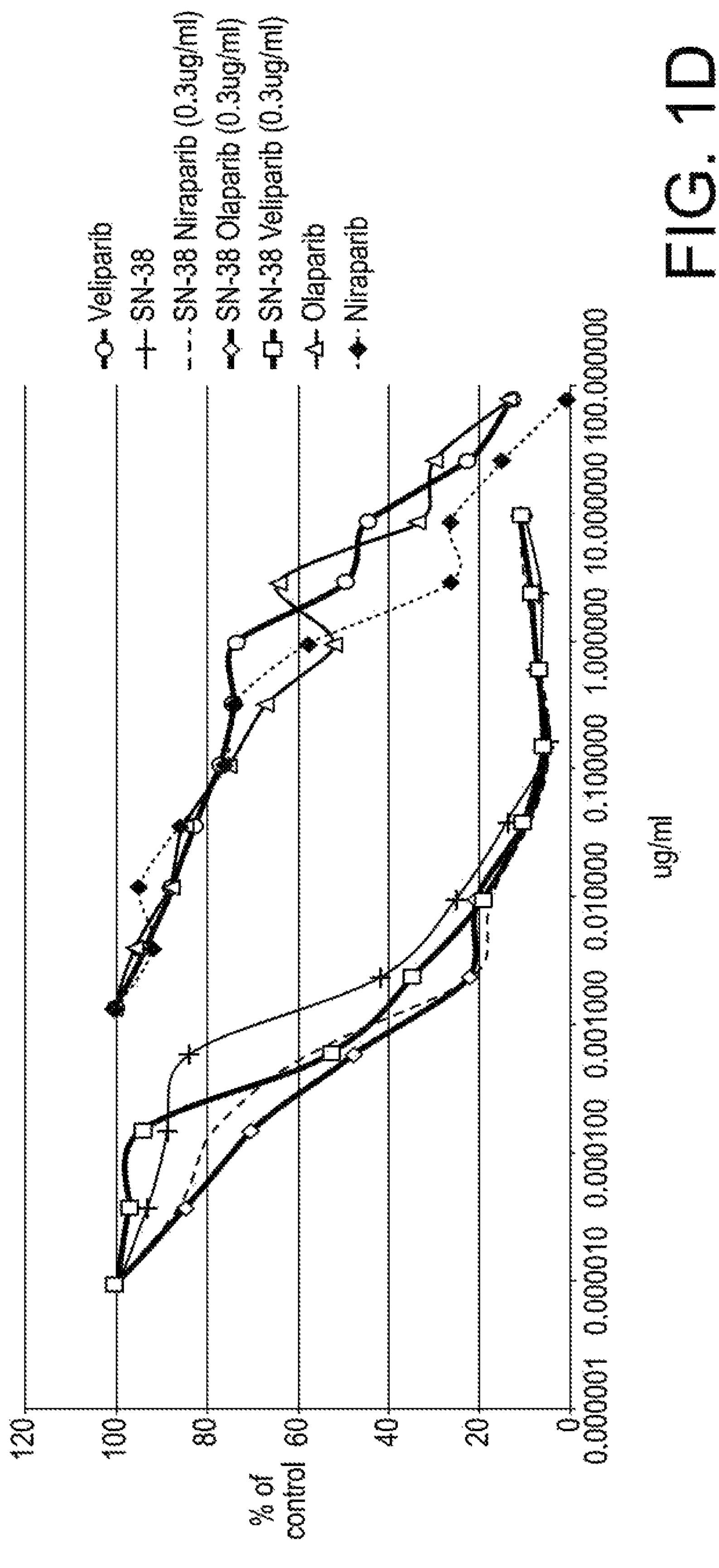
FIG. 1D is a graph showing the results of a cell viability in vitro measurement of SW756 human cervical cancer cells treated with the topoisomerase 1 inhibitor SN-38 and various PARP inhibitors.
Figure 1E:
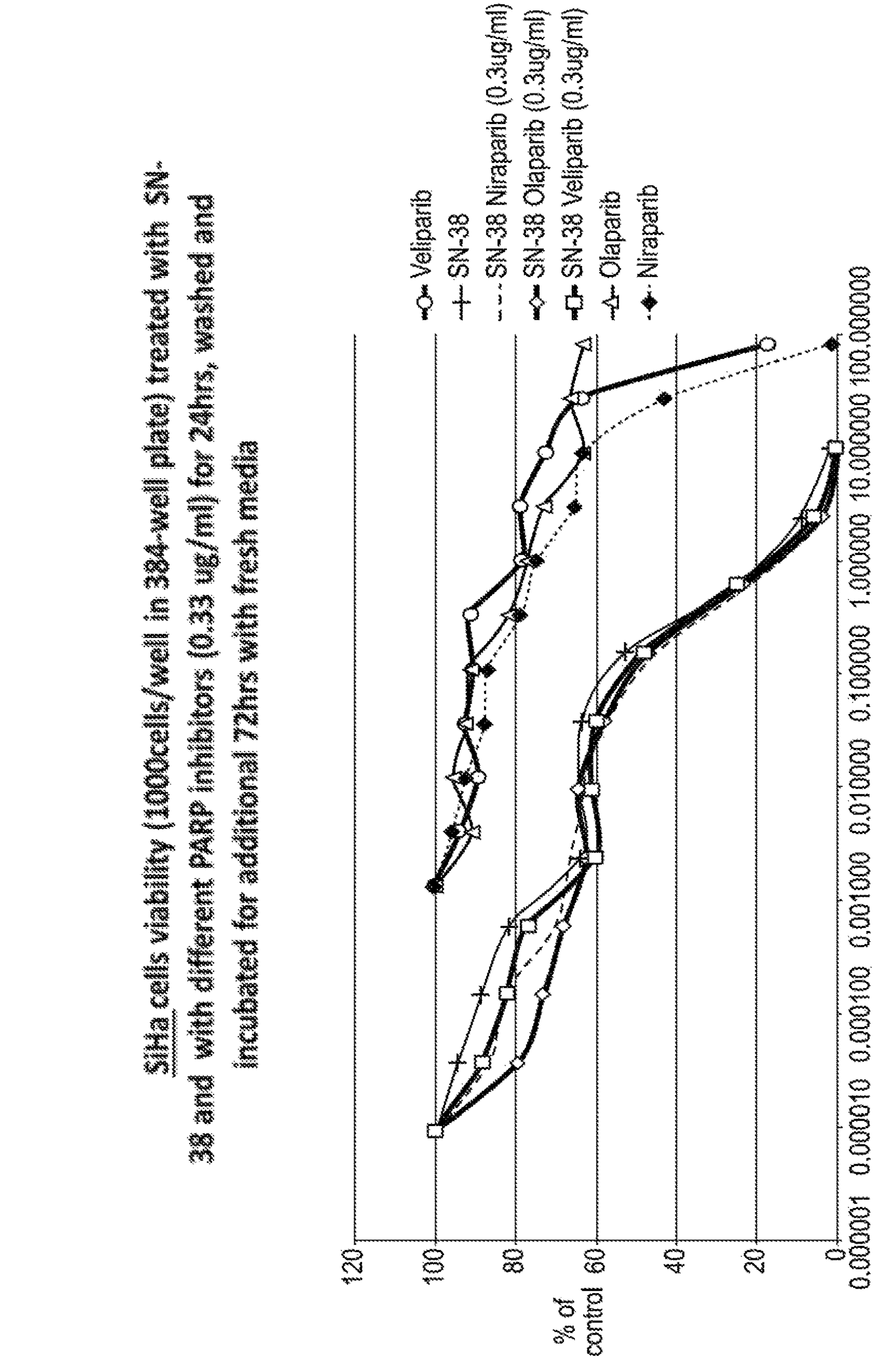
FIG. 1E is a graph showing the results of a cell viability in vitro measurement of SiHa human cervical cancer cells treated with the topoisomerase 1 inhibitor SN-38 and various PARP inhibitors.

The present disclosure provides for methods of administering a combination of a topoisomerase-1 (Top1) inhibitor (e.g., irinotecan and/or its metabolite SN-38) and a PARP inhibitor to a tumor with reduced peripheral toxicity. The Top1 inhibitor can be administered in a liposome formulation resulting in the prolonged accumulation of the Top1 inhibitor in a solid tumor compared to peripheral plasma and/or healthy organs. Subsequently, a PARP inhibitor can be administered after a period of time permitting a reduction in the amount of the Top1 inhibitor outside the tumor relative to the amount of Top1 inhibitor within the tumor. Preferably, the Top1 inhibitor is administered as a liposomal irinotecan that provides SN-38 to a solid tumor.

Methods of treating a cancer are provided, as well as therapeutic uses of PARP inhibitor compounds in combination with liposomal irinotecan formulations for the treatment of cancer, particularly cancer comprising solid tumors. These uses and methods can provide a treatment regimen comprising: (a) administering to a patient in need thereof an effective amount of an irinotecan liposomal formulation; and (b) after completion of the administration of the Top1 inhibitor, administering to the patient an effective amount of a PARP inhibitor, wherein the PARP inhibitor is administered to the patient following an interval that allows for a reduction in peripheral toxicity as compared to simultaneous administration of the Top1 inhibitor and the PARP inhibitor. The interval can be selected to provide time for sufficient clearance of the Top1 inhibitor (e.g., either or both of irinotecan and SN-38) from the blood plasma to avoid peripheral toxicity due to the synergistic toxic effects of the combination of Top1 inhibitor and PARP inhibitor, while allowing an effective quantity of Top1 inhibitor to remain in one or more tumors within the patient for the subsequent administration of the PARP inhibitor to have a desired synergistic therapeutic effect. This treatment regimen can preferably provide one or more attributes, which may include increased efficacy of the combination as compared to single agent treatment; reduced side effects, dosing the drugs at a higher dose compared with administration of the combination of a PARP inhibitor and a non-liposomal Top1 inhibitor.

The uses and methods disclosed herein are based in part on experiments evaluating the combination of a topoisomerase 1 inhibitor (e.g., liposomal irinotecan or SN-38) and a PARP inhibitor in both pre-clinical and human clinical studies. The topoisomerase 1 inhibitor was administered in certain in vitro animal models using a formulation delivering a more prolonged exposure of the topoisomerase 1 inhibitor (e.g., irinotecan and/or the irinotecan active metabolite designated SN-38) within solid tumors than in peripheral tissue and plasma outside the tumor. Combinations of the topopisomerase 1 inhibitor SN38 and/or irinotecan and PARP inhibitor compounds were rested in various in vitro experiments. As detailed in Example 1, the in vitro testing of multiple combinations of a topoisomerase 1 inhibitor (SN38) and various PARP inhibitors in more than 20 different cancer cell lines (including cervical, breast, ovarian, colorectal, pancreatic, and small cell lung cancer cell lines) all demonstrated decreased cancer cell line viability (FIGS. 1A, 1B, 1C, 1D, 1E, 2A, 2B, 2C, 2D, 2E, and 13A). The liposomal irinotecan (MM398) demonstrated greater tumor volume reduction than non-liposomal (free) irinotecan (CPT11) in mouse xenograft studies across multiple types of cancer cell lines (including breast, ovarian, colorectal and pancreatic cancer cell lines).

As detailed in Example 2, the tolerability of a topoisomerase 1 inhibitor (liposomal irinotecan) administered in combination with various PARP inhibitors was evaluated by measuring the change in animal (mouse) body weight in multiple murine models by comparing various dosing schedules. In some experiments, both liposomal irinotecan and a PARP inhibitor were administered together on the same day (day 1). In other experiments, the PARP inhibitor was first administered daily starting 2, 3 or 4 days after each administration of the liposomal irinotecan. The PARP inhibitor was administered for multiple consecutive days (e.g., 3 consecutive days), and not administered on the same day as the topoisomerase 1 inhibitor. As detailed in multiple experiments herein, administration oi the PARP inhibitor at least one day after the liposomal irinotecan resulted in improved tolerability of comparable combined doses of the PARP inhibitor and liposomal irinotecan (MM-398) as measured by change in percent bodyweight in the animal (e.g., FIGS. 6A, 6B, 6C, 6D, 8A, and 8B). Delaying the administration of the PARP inhibitor 2, 3 or 4 days after administration of the liposomal irinotecan led to greater overall tolerability of a combined administration of the liposomal irinotecan and the PARP inhibitor, compared to the administration of the liposomal irinotecan and the PARP inhibitor on the same day. For example, administration of veliparib on days 2, 3 and 4 after administration of liposomal irinotecan on day 1 resulted in successively increased tolerability (measured as higher percent mouse bodyweight) of the combination of these two drugs (observed at 15 mg/kg liposomal irinotecan dose an day 1 followed by veliparib dosing on days 2, 3 and 4 (FIG. 5A); at 28 mg/kg liposomal irinotecan dosage on day 1 followed by veliparib dosing on days 3, 4, and 5 (FIGS. 5B and 8B), or followed by veliparib dosing on days 2, 3 and 4 (FIG. 8B); and at 50 mg/kg liposomal irinotecan dose on day 1 followed by veliparib dosing on days 4, 5 and 6 (FIG. 5C), or followed by veliparib dosing on days 2, 3 and 4 or followed by veliparib dosing on days 3, 4, and 5 (FIG. 8A)). Similarly, administering olaparib starting on days 2 or 3 after MM398 resulted in comparable or improved tolerability compared to administration of both agents on day 1. For example, administering a 200 mg/kg dose of olaparib to mice on days 2, 3, 4 and 5 after administration of 10 mg/kg MM398 liposomal irinotecan on day 1 resulted in a lower reduction in bodyweight than administering the same doses of both MM398 and olaparib on days 1, 2, 3 and 4.

Combinations of a topoisomerase 1 inhibitor (SN38 and/or irinotecan) and PARP inhibitor compounds were tested in various preclinical in vivo experiments to evaluate the effectiveness of the administration of various PARP inhibitors starting 3 or 4 days after administration of the liposomal topoisomerase 1 inhibitor MM398. As detailed in Example 3, the administration of liposomal irinotecan (MM398) on day 1 followed by the PARP inhibitor veliparib on either days 3, 4 and 5 or days 4, 5, and 6, resulted in decreased tumor volume and extended percent survival in mouse xenograft models of cervical cancer using two different cell lines (MS751 and C33A) (FIGS. 7A, 7B, 9A, 9B, 10 and 11).

Based in part on these experiments, methods of treating human cancer include the administration of a PARP inhibitor one or more days (preferably 2, 3, 4, 5 or 6 days) after the administration of liposomal topoisomerase inhibitor such as liposomal irinotecan. Preferably, the PARP inhibitor and the liposomal irinotecan are not administered on the same day. Example 3 provides preferred embodiments for the use of liposomal irinotecan and one or more PARP inhibitors for the treatment of human cancer, such as cervical cancer, while other embodiments (e.g., Table 3) are also provided.

Topoisomerase Inhibitors, Including Liposomal Irinotecan and Camptothecin Conjugates The topoisomerase inhibitor can be administered in any form that provides for the prolonged retention of a topoisomerase-1 inhibitor activity within a tumor compared to outside the tumor, after administration of the topoisomerase inhibitor. For example, the topoisomerase inhibitor can be a formulation that delivers SN-38 to a tumor cell in vivo, administered in an amount and manner providing a higher concentration of the SN-38 within the tumor than outside the tumor for a period of time after administration of the topoisomerase inhibitor. Suitable formulations of topoisomerase inhibitors include conjugate molecules of a topoisomerase inhibitor (e.g., camptothecin conjugated to a polymer or antibody), liposomes containing a topoisomerase inhibitor or other targeted release formulation technologies. The Top1 inhibitor is preferably formulated to provide prolonged accumulation in a tumor site, compared to accumulation in healthy (non-cancer) tissue outside the tumor site (e.g., in the plasma and/or healthy organs such as colon, duodenum, kidney, liver, lung and spleen). Various Top1 inhibitor liposomal formulations are described in U.S. Pat. No. 8,147,867 and U.S. Patent Application Publication No. 2015/0005354, both of which are incorporated herein by reference.

In one embodiment, the topoisomerase inhibitor is SN-38, camptothecin or a compound that is converted to SN-38 within the body, such as irinotecan. Irinotecan and SN-38 are examples of Top1 inhibitors. Irinotecan is converted by esterase enzymes into the more active metabolite, SN-38. The chemical name of irinotecan is (S)-4,11-diethyl -3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate. Irinotecan hydrochloride trihydrate is also referred to by the name CPT-11 and by the trade name CAMPTOSAR®.

The topoisomerase inhibitor can be camptothecin conjugated to a biocompatible polymer such as a cyclodextrin or cyclodextrin analog (e.g., sulfonated cyclodextrins). For example, the topoisomerase inhibitor can be a cyclodextrin-containing polymer chemically bound to a camptothecin, irinotecan, SN-38 or other topoisomerase 1 inhibitor compound. A cyclodextrin-camptothecin conjugated topoisomerase 1 inhibitor can be administered at a pharmaceutically acceptable dose including 6, 12, or 18 mg/m2 weekly administration, or 12, 15 or 18 mg/m2 biweekly administration. Examples of camptothecin-cyclodextrin conjugate topoisomerase 1 inhibitors (e.g., the cyclodextrin-containing polymer conjugate with camptothecin designated "CRLX101"), and related intermediates for preparing the same, are disclosed, for example, in Greenwald et al., Bioorg. Med. Chem., 1998, 6, 551-562, as well as United States Patent Application 2010/0247668, United States Patent Application 2011/0160159 and United States Patent Application 2011/0189092.

The topoisomerase inhibitor can also be a liposomal formulation of a topoisomerase inhibitor such as irinotecan, camptothecin or topotecan. Liposomal irinotecan (e.g., MM-398, also called "nal-IRI") is a highly stabilized liposomal formulation of irinotecan that provides for sustained exposure of irinotecan, and the active metabolite SN-38 in the tumor to a higher proportion of cells during the more sensitive S-phase of the cell cycle. MM-398 is a liposomal irinotecan that has shown promising preclinical and clinical activity in a range of cancer types, and was recently approved in the United States in combination with 5-FU/LV for patients with metastatic adenocarcinoma of the pancreas after disease progression following gemcitabine-based therapy. Compared with free irinotecan, nal-IRI has an extended PK profile with prolonged local tumor exposure of MM-398 and SN-38. Since SN-38 is cleared more quickly from normal tissues than from tumor, it is hypothesized that delayed dosing of veliparib relative to MM-398 will allow for the expected window of maximum irinotecan-induced toxicity to pass in the absence of concurrent veliparib toxicity. However, the tumor levels of SN-38 are predicted to be sustained upon subsequent veliparib dosing, therefore maintaining the ability of both drugs to act on tumor tissue simultaneously and maintain synergy.

One suitable liposomal Top1 inhibitor formulation is liposomal irinotecan available under the brand name ONIVYDE® (irinotecan liposome injection) (Merrimack Pharmaceuticals, Inc. Cambridge, Mass.), previously designated "MM-398" prior to FDA approval, and liposomal irinotecan products that are bioequivalent to ONIVYDE. The ONIVYDE/MM-398 (irinotecan liposome injection) includes irinotecan as an irinotecan sucrosofate salt encapsulated in liposomes for intravenous use. The drug product liposome is a small unilamellar lipid bilayer vesicle, approximately 110 nm in diameter, which encapsulates an aqueous space which contains irinotecan in a gelated or precipitated state, as the sucrosofate salt. The liposome carriers are composed of 1,2-distearoyl-sn-glycero-3-phosphocholine (DSPC), 6.81 mg/mL; cholesterol, 2.22 mg/mL; and methoxy-terminated polyethylene glycol (MW 2000)-distearoylphosphatidylethanolamine (MPEG-2000-DSPE), 0.12 mg/mL. Each mL also contains 2-[4-(2-hydroxyethyl) piperazin-1-yl]ethanesulfonic acid (HEPES) as a buffer, 4.05 mg/mL; sodium chloride as isotonicity reagent, 8.42 mg/mL, ONIVYDE/MM-398 is believed to include about 80,000 molecules of irinotecan in a gelated or precipitated state as a sucrosofate salt, encapsulated in a liposome of about 100 nm in diameter.

As used herein, unless otherwise indicated, the dose of irinotecan in ONIVYDE/MM-398 refers to the dose of irinotecan based on the molecular weight of irinotecan hydrochloride trihydrate (i.e., "(salt)" dose), unless clearly indicated otherwise. Alternatively, the irinotecan dose in ONIVYDE/MM-393 may also be expressed as the irinotecan free base (i.e., "(base)" dose). Converting a dose based on irinotecan (salt) dose to an irinotecan (base) dose based on irinotecan free base is accomplished by multiplying the dose based on irinotecan hydrochloride trihydrate with the ratio of the molecular weight of irinotecan free base (586.68 g/mol) and the molecular weight of irinotecan hydrochloride trihydrate (677.19 g/mol). This ratio is 0.87 which can be used as a conversion factor. For example, the 80 mg/m$^2$ irinotecan (salt) dose of ONIVYDE/MM-398 refers to the amount of irinotecan based on irinotecan hydrochloride trihydrate, and is equivalent to a 69.60 mg/m$^2$ irinotecan (base) dose of ONIVYDE/MM-398 based on irinotecan free base (80×0.87). In the clinic this is rounded to 70 mg/m$^2$ to minimize any potential dosing errors. Similarly, a clinical dose of 120 mg/m$^2$ (salt) dose of ONIVYDE/MM-398 (based on the corresponding amount of irinotecan hydrochloride trihydrate providing the same amount of irinotecan free base) is equivalent to 100 mg/m$^2$ (base) dose of ONIVYDE/MM-398 (based on the actual amount of irinotecan free base administered in the liposomal irinotecan).

ONIVYDE/MM-398 has been shown to improve the pharmacokinetic and safety profile of the free irinotecan, through high retention of the irinotecan molecules within the liposome, by extending the half-life of irinotecan in the plasma, and increased exposure of tumor cells to irinotecan compared with other organs. Table 1 below provides a summary of median (% IQR)*total irinotecan and SN-38 pharmacokinetic parameters observed in patients with solid tumors after administration of ONIVYDE/MM-398 at a dose of 80 mg/m$^2$ irinotecan (salt) dose administered once every 2 weeks.

TABLE 1

| | Total Irinotecan | | | | | SN-38 | | |
|---|---|---|---|---|---|---|---|---|
| Dose (mg/m$^2$) | $C_{max}$ [μg/ml] | $t_{1/2}$ [h]† | $AUC_{0-\infty}$ [h · μg/ml]† | $V_d$ [L/m$^2$]† | CL [L h/m$^2$]† | $C_{max}$ [ng/ml] | $t_{1/2}$ [h]† | $AUC_{0-\infty}$ [h · ng/ml]† |
| 80 (n = 25) | 38.0 (36%) | 26.8 (110%) | 1030 (169%) | 2.2 (55%) | 0.077 (143%) | 4.7 (89%) | 49.3 (103%) | 587 (69%) |

$$* \% \text{ IQR: } \% \text{ Interquartile Ratio} = \frac{\text{Interquartile} - \text{range}}{\text{Median}} \cdot 100\%$$

†$t_{1/2}$, $AUC_{0-\infty}$ and $V_d$ were only calculated for a subset of patients with sufficient number of samples in the terminal phase: n = 23 for total irinotecan; n = 13 for SN-38.

$C_{max}$: Maximum plasma concentration $t_{1/2}$: Terminal elimination half-life $AUC_{0-\infty}$: Area under the plasma concentration curve extrapolated to time infinity $V_d$: Volume of distribution For ONIVYDE/MM-398, over the dose range of 60 to 180 $mg/m^2$, the maximum concentrations of body total irinotecan and SN-38 increase linearly with dose. The AUCs of total irinotecan increase linearly with dose; the AUCs of SN-38 increase less than proportionally with dose. The half-lives of both total irinotecan and SN-38 do not change with dose. In a pooled analysis from 353 patients, higher plasma SN-38 $C_{max}$ was associated with increased likelihood of experiencing neutropenia, and higher plasma total irinotecan $C_{max}$ was associated with increased likelihood of experiencing diarrhea. Direct measurement of liposomal irinotecan shows that 95% of irinotecan remains liposome-encapsulated during circulation. The volume of distribution of MM-398 80 $mg/m^2$ is 2.2 $L/m^2$. The volume of distribution of Irinotecan HCl is between 110 $L/m^2$ (dose=125 $mg/m^2$) and 234 $L/m^2$ (dose=340 $mg/m^2$). The plasma protein binding of MM-398 is <0.44% of the total irinotecan in MM-398. The plasma protein binding of irinotecan HCl is 30% to 68% and approximately 95% of SN-38 is bound to human plasma proteins. The plasma clearance of total irinotecan from MM-398 $mg/m^2$ is 0.077 $L/h/m^2$ with a terminal half live of 26.8 h. Following administration of irinotecan HCl 125 $mg/m^2$, the plasma clearance of irinotecan is 13.3 $L/h/m^2$ with a terminal half live of 10.4 h.

Examples of an effective amount of liposomal irinotecan provided as MM-398 include doses (salt) from about 60 $mg/m^2$ to about 120 $mg/m^2$, including doses of 70, 80, 90, 100, 110 or 120 $mg/m^2$ (based on the weight of irinotecan hydrochloride trihydrate salt) and doses of 50, 60, 70, 80, 95, and 100 $mg/m^2$ (based on the weight of irinotecan free base), each given once every two (2) weeks (e.g., on days 1 and 15 of a 28 day antineoplastic treatment cycle). In some embodiments, the effective amount of MM-398 is about 80 $mg/m^2$ (salt), optionally administered in combination with 400 $mg/m^2$ of leucovorin over 30 minutes, followed by intravenous administration of 2400 $mg/m^2$ of 5-fluorouracil as an infusion over 46 hours. In some embodiments, the effective amount of MM-398 is about 90 $mg/m^2$ (free base).

Figure 16A:
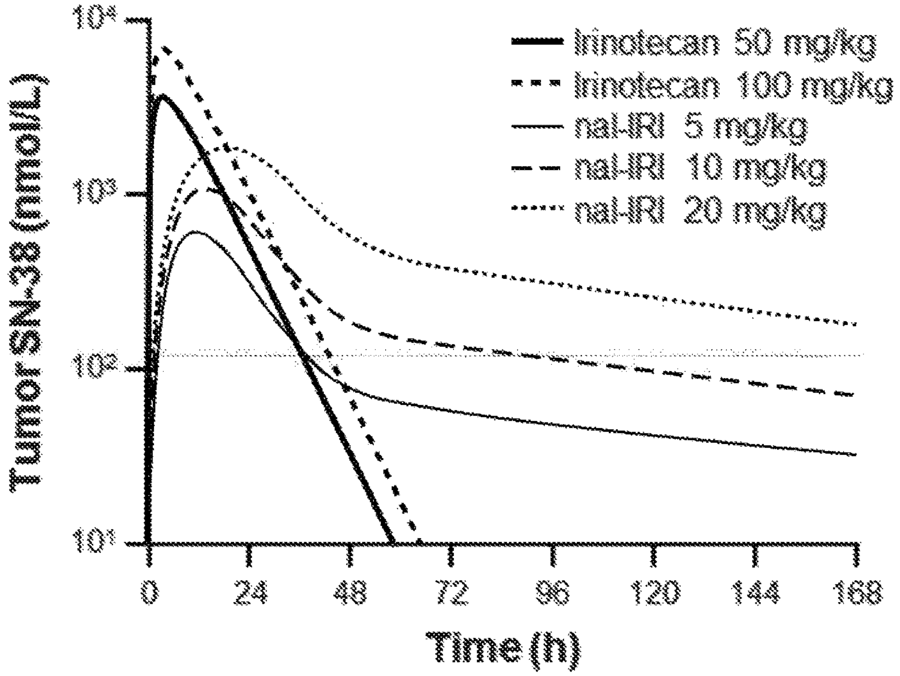
FIG. 16A is a graph showing the tumor SN-38 (nmol/L) measured in tumors after administration of free (non-liposomal) irinotecan (CPT-11) at 50 mg/kg or 100 mg/kg, compared to the administration of MM-398 (5 mg/kg, 10 mg/kg or 20 mg/kg).
Figure 16B:
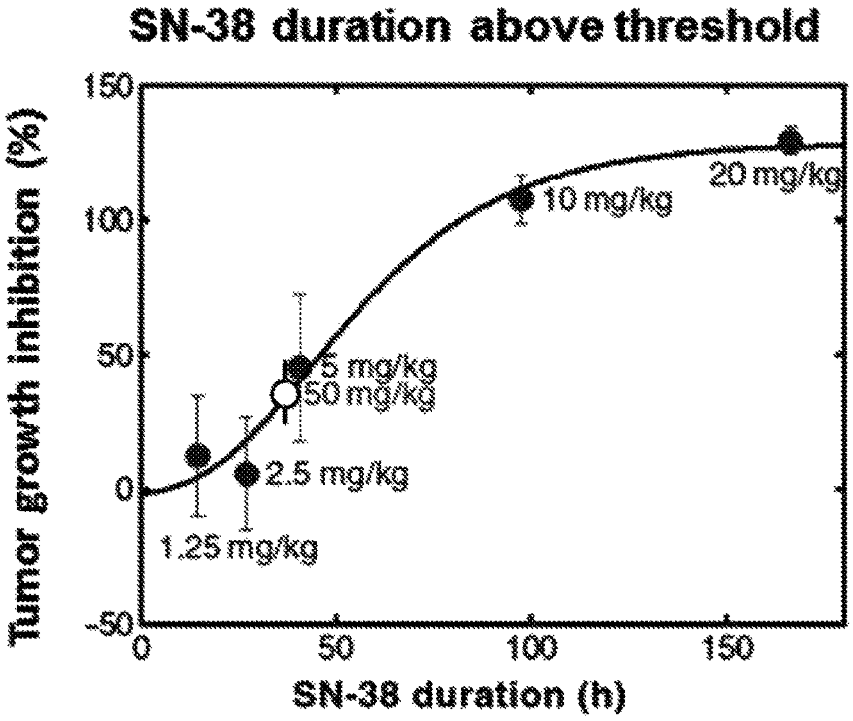
FIG. 16B is a graph showing levels of tumor growth inhibition as a function of time of SN-38 concentration required to yield tumor response.

Liposomal irinotecan MM-398 extends the tumor exposure of the topoisomerase 1 inhibitor SN-38. MM-398 liposomal irinotecan was found to be more active than irinotecan in multiple murine xenograph models. The duration of tumor exposure to the topoisomerase 1 inhibitor SN-38 above a threshold minimum concentration (e.g., 120 nM) correlated with anti-tumor activity of the liposomal irinotecan. In addition, MM-398 liposomal irinotecan can provide prolonged SN-38 tumor durations that exceed those provided by non-liposomal irinotecan. For example, FIG. 13B depicts tumor content of SN-38 in multiple murine cervical cancer models. Nude mice bearing cervical tumors were injected with a single dose of MM-398 at 10 mg/kg and tumor content of CPT-11 and SN-38 were measured by LC-MS. FIG. 16A is a graph showing the tumor SN-38 (nmol/L) measured in tumors after administration of free (non-liposomal) irinotecan (CPT-11) at 50 mg/kg or 100 mg/kg, compared to the administration of MM-398 (5 mg/kg, 10 mg/kg or 20 mg/kg). The graph depicts the prolonged accumulation of SN-38 (concentration) measured in a tumor after liposomal irinotecan (MM-398) administration compared to other organs, obtained using a using HT-29 colorectal cancer (CRC) tumor xenograft-bearing mice. FIG. 16B is a graph showing levels of tumor growth inhibition as a function of time of SN-38 concentration required to yield tumor response. Levels of SN-38 of 120 nM were identified as the SN-38 tumor concentration required to yield tumor response. The in vitro IC50 for SN-38 effect on cell line can be used as an in vivo threshold (GI50 for HT-29 was observed to be about 60 nM). MM-398 liposomal irinotecan was observed to prolong the duration of SN-38 exposure at doses of 10 mg/kg and 20 mg/kg.

PARP Inhibitors

PARPs are a family of enzymes involved in DNA repair that act via two mechanisms: catalytic inhibition and trapping of PARP-DNA complexes, and inhibition of this repair pathway can result in cell death following DNA damage. In preferred embodiments, combining PARP inhibitors with Top1 inhibitors results in increased efficacy in the clinic compared to either agent alone. While it has been demonstrated that synergism between PARP inhibitors and Top1 inhibitors is due to PARP catalytic inhibition, and does not involve PARP trapping, this promising preclinical activity has given rise to unacceptable toxicity in the clinic for these combinations.

The PARP inhibitor can be selected from compounds that inhibit Poly(ADP-ribose) polymerase (PARP), a family of enzymes involved in DNA repair. Preferably, the PARP inhibitor is a compound that acts via two mechanisms: catalytic inhibition and trapping of PARP-DNA complexes. The PARP inhibitor can be one or more clinically available PARP inhibitor compounds (e.g. talazoparib, niraparib, olaparib, and veliparib, among others), including compounds that can act via both mechanisms, although to different degrees. For example, niraparib is much more potent at PARP trapping than veliparib, whereas they both exhibit similar PARP catalytic activity. The PARP inhibitor can be selected from one or more compounds selected from the group consisting of talazoparib, niraparib, olaparib, veliparib, iniparib, rucaparib, CEP 9722 or BGB-290. In a further embodiment, the PARP inhibitor is veliparib, olaparib, rucaparib or niraparib. In another embodiment, the PARP inhibitor is veliparib, or olaparib. The PARP inhibitor can be veliparib administered after liposomal irinotecan. The PARP inhibitor can be olaparib administered after liposomal irinotecan Olaparib is indicated as monotherapy in patients with deleterious or suspected deleterious germline BRCA mutated (as detected by an FDA-approved test) advanced ovarian cancer who have been treated with three or more prior lines of chemotherapy. The recommended dose of olaparib for this indication is 400 mg (eight 50 mg capsules) taken twice daily, for a total daily close of 800 mg. Patients taking olaparib are instructed to avoid concomitant use of strong and moderate CYP3A inhibitors and consider alternative agents with less CYP3A inhibition. If the inhibitor cannot be avoided, reduce the Lynparza dose to 150 mg (three 50 mg capsules) taken twice daily for a strong CYP3A inhibitor or 200 mg (four 50 mg capsules) taken twice daily for a moderate CYP3A inhibitor.

The PARP inhibitor can inhibit PARP 1 and/or PARP 2. For example, the PARP inhibitor can be a PARP ½ inhibitor with IC50 of 5 nM/1 nM in cell-free assays and 300-times less effective against tankyrase-1 (e.g., olaparib). The PARP inhibitor can be an inhibitor of PARP 1 and PARP2 with Ki of 5.2 nM and 2.9 nM respectively in cell-free assays, and inactive to SIRT2 (e.g., veliparib). The PARP inhibitor can be an inhibitor of PARP 1 with a Ki of 1.4 nM in a cell-free assay, and can also show binding affinity for other PARP domains (e.g., rucaparib). The PARP inhibitor can be effective against triple negative breast cancer (TNBC) alone or in combination with other agents. The PARP inhibitor can be a PARP1 inhibitor with an IC50 of 0.58 nM in a cell free assay that does not inhibit PARG and is sensitive to a PTEN mutation (e.g., talazoparib). The PARP inhibitor can be a potent and selective tankyrase inhibitor with an IC50 of 46 nM and 25 nM for TNKS 1/2, respectively (e.g., G007-LK). The PARP inhibitor can be a potent inhibitor of PARP 1 with a Ki of less than about 5 nM in a cell free assay (e.g., AG-14361). The PARP inhibitor can be a selective inhibitor of PARP 2 with an IC50 of 0.3 micromolar, and can be about 27-fold selective against PARP 1 (e.g., UPF-1069). The PARP inhibitor can be a potent and selective inhibitor with an IC50 for PARP 3 of about 0.89 micromolar, and about 7-fold selectivity over PARP 1 (e.g., ME0328). The PARP inhibitor can be an inhibitor of PARP 1 and PARP2 with Ki values of 1 nM and 1.5 nM, respectively.

Preferred examples of PARP inhibitors are provided in the table 2 A below, as well as pharmaceutically acceptable prodrugs, salts (e.g., tosylates) and esters thereof.

TABLE 2A

| Examples of PARP inhibitors | |
|---|---|
| Olaparib (AZD-2281) | 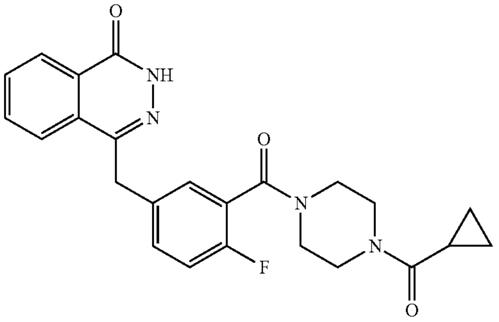 [SMILES: O=C(c1cc(Cc2n[nH]c(=O)c3ccccc23)ccc1F)N1CCN(C(=O)C2CC2)CC1] |
| Veliparib (ABT-888) | 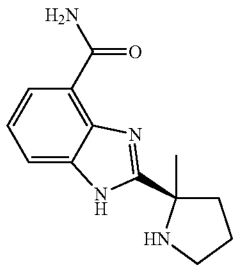 [SMILES: C[C@]1(c2nc3c(C(N)=O)cccc3[nH]2)CCCN1] |
| Niraparib (MK04827) | 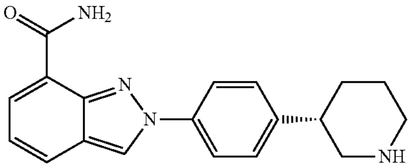 [SMILES: NC(=O)c1cccc2cn(-c3ccc([C@@H]4CCCNC4)cc3)nc12] |
| Rucaparib (AG 014699) | 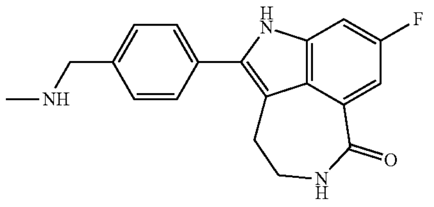 [SMILES: CNCc1ccc(-c2[nH]c3cc(F)cc4c3c2CCNC4=O)cc1] |
| Talazoparib (BMN-673) | 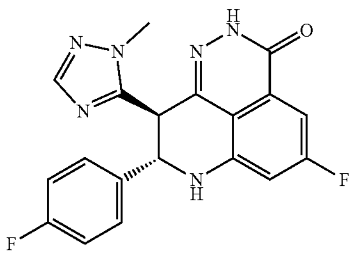 [SMILES: Cn1ncnc1[C@H]1c2n[nH]c(=O)c3cc(F)cc(c23)N[C@@H]1c1ccc(F)cc1] |

TABLE 2A-continued

| Examples of PARP inhibitors | |
|---|---|
| Iniparib (BSI-201 | 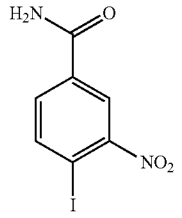 [SMILES: NC(=O)c1ccc(I)c([N+](=O)[O-])c1] |

The dose of the PARP inhibitor and the frequency of dosing can be selected based on various characteristics of the PARP inhibitor, including the pharmacokinetic properties of the compound (e.g., half-life), prior dosing regimens and patient characteristics. Parameters that can be used in selecting the PARP inhibitor dose include those listed in Table 2B below.

In addition, patients can be selected to receive treatment combining a topoisomerase inhibitor and a PARP inhibitor. For example, patients can be selected based on their status in BRCA (e.g. BRCA1, BRCA2), Homologous Recombination Deficiency (HRD), BROCA-HR or other genetic risk panel analysis of a patient.

TABLE 2B

Characteristics of Some PARP inhibitors

| Characteristic | Veliparib | Olaparib | Rucaparib | Niraparib | Talazoparib |
|---|---|---|---|---|---|
| Molecular Weight | 244.3 | 434.5 | 323.4 | 320.4 | 380.4 |
| PARP1 IC50 | 4.73-5.2 | 1.94-5 | 1.4-1.98 | 2.1-3.8 | 0.57-1.2 |
| PAR EC50 | 5.9 | 3.6 | 4.7 | | 2.5 |
| Monotherapy dosing | 200-400 mg BID | 300 mg BID | 240-600 mg BID | 300 mg QD | 1 mg QD |
| CDx | BRCA | BRCA, HRD | HRD | BRCA, HR | HRD, HR |

In the methods of this disclosure, the PARP inhibitor is administered at a therapeutically effective dose (e.g., a dose selected for the PARP inhibitor monotherapy, such as from about 200 mg/day to about 800 mg/day for veliparib). In a further embodiment, the PARP inhibitor is administered twice daily at a dose of from about 100 to about 400 mg for veliparib, rucaparib or olaparib. In some embodiments, 200 mg BID dose of veliparib is administered to patients after (e.g., 3-5 days after) each administration of liposomal irinotecan.

Uses in the Treatment of Cancer

In the methods of this disclosure, the PARP inhibitor is preferably administered after an "effective irinotecan plasma clearing interval," as defined above. The effective plasma clearing interval in the methods of this disclosure is from about 24 to about 168 hours, including 48 hours to about 168 hours. In a further embodiment, the effective plasma clearing interval is from about 48 to about 96 hours. In a further embodiment, the effective plasma clearing interval is 24 hours or 2, 3, 4 or 5 days.

In certain embodiments, the MM-398 and the PARP inhibitor are administered in at least one cycle. A cycle comprises the administration of a first agent (e.g., a first prophylactic or therapeutic agents) for a period of time, followed by the administration of a second agent (e.g., a second prophylactic or therapeutic agents) for a period of time, optionally followed by the administration of a third agent (e.g., a third prophylactic or therapeutic agents) for a period of time and so forth, and repeating this sequential administration, i.e., the cycle. In one embodiment, the combination of MM-398 and a PARP inhibitor is administered for at least one cycle. In one embodiment the cycle is a 2 week cycle. In another embodiment, the cycle is a 3 week cycle. In another embodiment, the cycle is a 4 week cycle. In one embodiment MM-398 is administered at the beginning of the cycle and administration of a PARP inhibitor (e.g., veliparib) is delayed until at least about 24, 48, 72, 96, or 120 hours, after the administration of MM-398. In one embodiment, MM-398 is administered as part of a 28 day cycle on days 1 and 15 and the PARP inhibitor is administered on days 3-12 and on days 17-25. In another embodiment, MM-398 is administered as part of a 28 day cycle on days 1 and 15 and the PARP inhibitor is administered on days 5-12 and days 19-25.

In some examples, including the protocols in Table 3, the PARP inhibitor is not administered within 3 days of the administration of liposomal topoisomerase 1 inhibitor such as MM-398 liposomal irinotecan (i.e., the PARP inhibitor is only administered on days that are both at least 2, 3, 4 or 5 days after the administration of the liposomal topoisomerase 1 inhibitor, and 2, 3, 4 or 5 days prior to the next administration of the liposomal topoisomerase 1 inhibitor). Table 3 shows dose timing protocols for administering a therapeutically effective amount of a PARP inhibitor and liposomal irinotecan on certain days of a 28-day antineoplastic treatment cycle.

TABLE 3

Examples of 28-day Treatment Cycles

| Protocol | PARP inhibitor given on days | Liposomal Irinotecan given on days |
|---|---|---|
| 1 | 3-12; 17-25 | 1, 15 |
| 2 | 4-12; 17-25 | 1, 15 |

TABLE 3-continued

| Examples of 28-day Treatment Cycles | | |
|---|---|---|
| Protocol | PARP inhibitor given on days | Liposomal Irinotecan given on days |
| 3 | 5-12; 17-25 | 1, 15 |
| 4 | 6-12; 17-25 | 1, 15 |
| 5 | 3-12; 18-25 | 1, 15 |
| 6 | 4-12; 18-25 | 1, 15 |
| 7 | 5-12; 18-25 | 1, 15 |
| 8 | 6-12; 18-25 | 1, 15 |
| 9 | 3-12; 19-25 | 1, 15 |
| 10 | 4-12; 19-25 | 1, 15 |
| 11 | 5-12; 19-25 | 1, 15 |
| 12 | 6-12; 19-25 | 1, 15 |

In some examples, the PARP inhibitor is administered on one or more of days of a 28-day antineoplastic treatment cycle. For example, the PARP inhibitor can be administered on one or more of days 3, 4, 5, 6, 8, 9, 10, 11 and 12 and 19, 20, 21, 22, 23, 24 and 25 of the 28-day antineoplastic treatment cycle when the liposomal irinotecan (e.g., MM-398) is administered once every two weeks, or on days 1 and 15 of the 28-day antineoplastic treatment cycle.

Methods of treatment and therapeutic uses of PARP inhibitors and topoisomerase inhibitors (e.g., liposomal irinotecan) disclosed herein are useful in the treatment of various forms of cancer Preferably, the cancer includes a diagnosed solid tumor. In some examples, the cancer (e.g., solid tumor) is of a tumor type with one or more DNA repair pathway deficiencies, such as breast and ovarian tumors with BRCA1 or BRCA2 mutations.

In the methods of this disclosure, the cancer is cervical cancer, ovarian cancer, breast cancers including triple negative breast cancer (TNBC), non-small cell lung cancer (NSCLC), small cell lung cancer (SCLC), gastric cancer, pancreatic cancer, colorectal cancer, or a neuroendocrine tumor.

The methods of this disclosure can further comprise administering to the patient one or more additional agents including, but not limited, to anti-emetics such as a 5-HT3 antagonist; agents for treating of diarrhea, such as loperamide; dexamethasone; or other chemotherapeutic agents.

In one embodiment, the methods of the present disclosure result in a pathologic complete response (pCR), complete response (CR), partial response (PR) or stable disease (SD). In another embodiment the combination therapy with MM-398 and a PARP inhibitor, e.g., veliparib, results in therapeutic synergy.

Further aspects include providing an existing standard of care therapy to the patients, which may or may not include treatment with appropriate single agents. In some instances, the standard of care may include administration of a PARP inhibitor compound.

Thus, in one aspect, the present disclosure provides a method of treating a patient with cancer and having a tumor, the method comprising:

i. parenterally (e.g., intravenously) administering to the patient an effective amount of an irinotecan liposomal formulation; and ii. administering to the patient an effective amount of a PARP inhibitor wherein the PARP inhibitor is administered after an effective irinotecan plasma clearing interval.

The present disclosure provides a method of treating a patient with cancer and having a tumor, the method comprising a treatment regimen that may be repeated at weekly or longer intervals (e.g., Q2W, Q3W, or Q4W), each instance of the treatment comprising:

i. intravenously administering to the patient an effective amount of an irinotecan liposomal formulation of a Top1 inhibitor such as irinotecan, topotecan, lurtotecan, indotecan, and indimitecan; and ii. administering to the patient and effective amount of a PARP inhibitor wherein the PARP inhibitor is administered after an interval following completion of the administration of the Top1 inhibitor, e.g., an effective irinotecan plasma clearing interval.

In a further embodiment, the method comprises:

i. intravenously administering to the patient an effective amount of an irinotecan liposomal formulation having a terminal elimination half-life of about 26.8 hours and a maximal irinotecan plasma concentration of about 38.0 micrograms/ml; and ii. administering to the patient and effective amount of a PARP inhibitor wherein the PARP inhibitor is administered after an interval of 24 hours or up to three days following completion of the administration of the irinotecan.

EXAMPLES

The following non-limiting examples illustrate the methods of the present disclosure.

Example 1

In Vitro Studies

In vitro studies were performed testing combinations of various PARP inhibitors and topoisomerase inhibitors liposomal irinotecan and SN-38.

FIGS. 1A-1D show line graphs that depict cervical cancer cell viability following treatment with SN-38 and/or various PARP inhibitors. Unless otherwise indicated, the data in each of these figures was obtained by measuring cell viability of 5 different cervical cancer cells (MB-180 in FIG. 1A, MS-751 in FIG. 1B, C-33A in FIG. 1C, SW756 in FIG. 1D and SiHa in FIG. 1E) with 1000 cells/well in a 384 well plate treated with SN-38 (topoisomerase 1 inhibitor) and/or one of 3 different PARP inhibitors (veliparib, niraparib, or olaparib) at 0.33 micrograms/mL) for 24 hours, followed by washing and incubation for an additional 72 hours with fresh media.

The combination of the topoisomerase 1 inhibitor SN-38 and various PARP inhibitors (veliparib, olaparib and rucaparib) were tested in vitro with various small cell lung cancer (SCLC), pancreatic cancer and breast cancer cell lines. At 2 nM SN-38 concentration, an additive/synergistic growth inhibition of the cancer cells was observed in combination with olaparib, veliparib and rucaparib (with veliparib observed to be slightly less potent in the combination with SN-38 than olaparib and rucaparib). At all concentrations tested, the static growth of the cancer cell population was achieved. FIGS. 2A-2E are graphs showing the results of in vitro experiments evaluating combinations of the topoisomerase 1 inhibitor SN38 with various PARP inhibitors, formatted according to the tables 4-5 below (plates of 5,000 cells/well, 100 microliters per well; drugs added with 20× at 10 microliters per drug, top up to 100 microliters total with DMEM; then initiate scan every 4 hours up to 68 hours).

TABLE 4

| | Small Cell Lung Cancer | | Pancreatic Cancer | | TNBC MDA- |
|---|---|---|---|---|---|
| Treatment | DMS-114 | NCI-H1048 | CFPAC-1 | BxPC-3 | MB-231 |
| SN-38 & Olaparib | Plate 1 | Plate 2 | Plate 3 | Plate 4 | Plate 5 |
| SN-38 & Rucaparib | Plate 1 | Plate 2 | Plate 3 | Plate 4 | Plate 5 |
| SN-38 & Veliparib | Plate 1 | Plate 2 | Plate 3 | Plate 4 | Plate 5 |

TABLE 5

| Target Concentrations | | | | |
|---|---|---|---|---|
| Drug | Active Range based on XTC008 | Estimated tumor range (nM) | Dose Level | Conc' (nM) |
| SN-38 | 1-50 nM | 3-163 nM (398): IRI < 200 nM | S1 | 2 |
| | | | S2 | 5 |
| | | | S3 | 10 |
| | | | S4 | 20 |
| | | | S5 | 50 |
| Olapano | 100)-10000 nM | 8000 nM | O1 | 2000 |
| | | | O2 | 4000 |
| | | | O3 | 8000 |
| Veliparib | 1000-10000 nM | >2000 nM | V1 | 2000 |
| | | | V2 | 4000 |
| | | | V3 | 8000 |
| Rucaparib | 1-100 nM (Panc) | <6000 nM | R1 | 2000 |
| | | | R2 | 4000 |
| | | | R3 | 8000 |

Figure 2A:
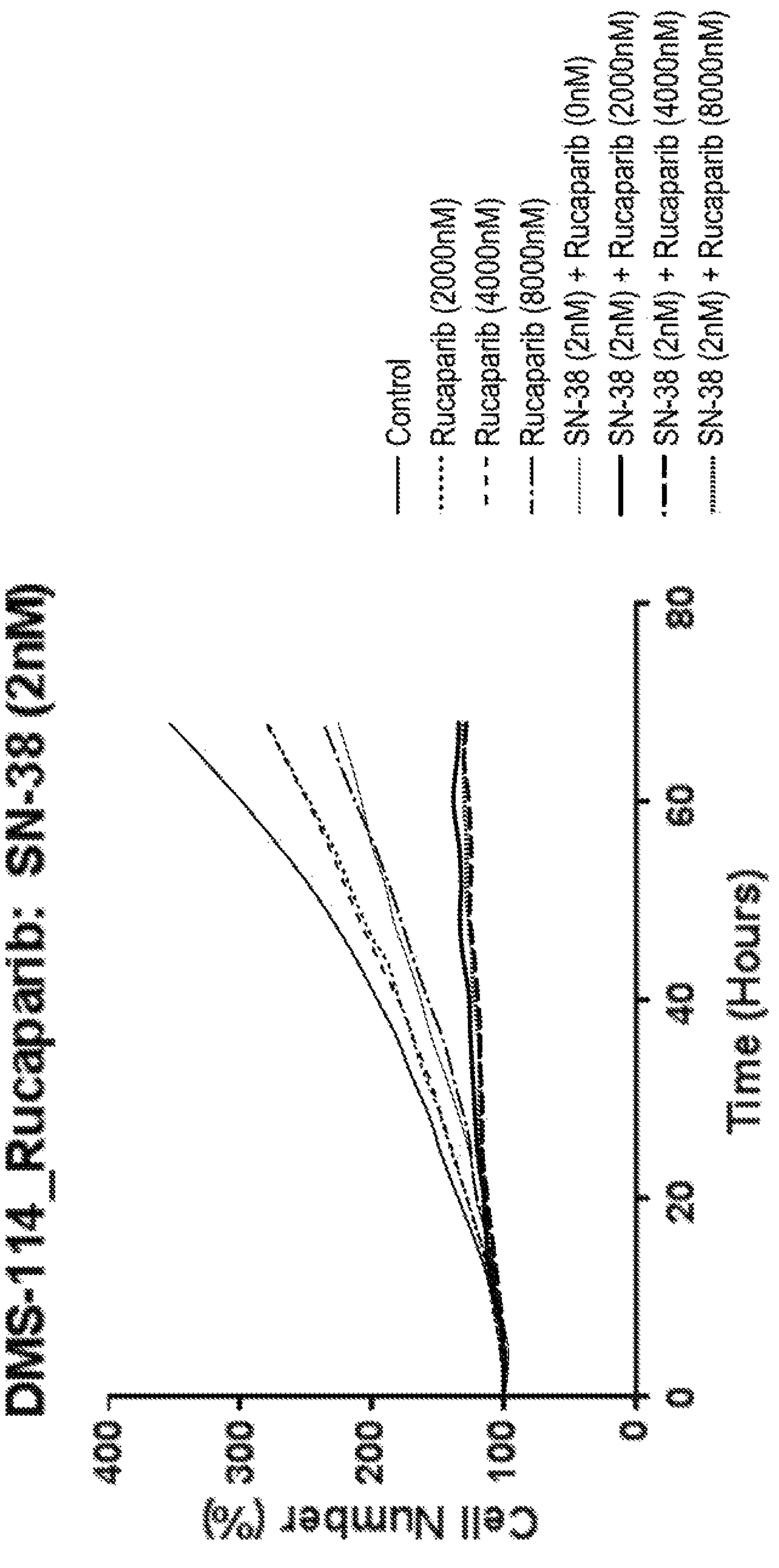
FIG. 2A is a graph showing the results of in vitro measurement of % cell number over time for DMS-114 small cell lung cancer cells treated with the topoisomerase inhibitor SN-38 and the PARP inhibitor rucaparib.

Additive/synergistic effects were observed between SN-38 at 2 nM combined with the tested PARP inhibitors olaparib, veliparib and rucaparib with DMS-114 SCLC cells. FIG. 2A is a graph showing the results of in vitro measurement of % cell number over time for DMS-114 small cell lung cancer cells treated with the topoisomerase inhibitor SN-38 and the PARP inhibitor rucaparib.

Figure 2B:
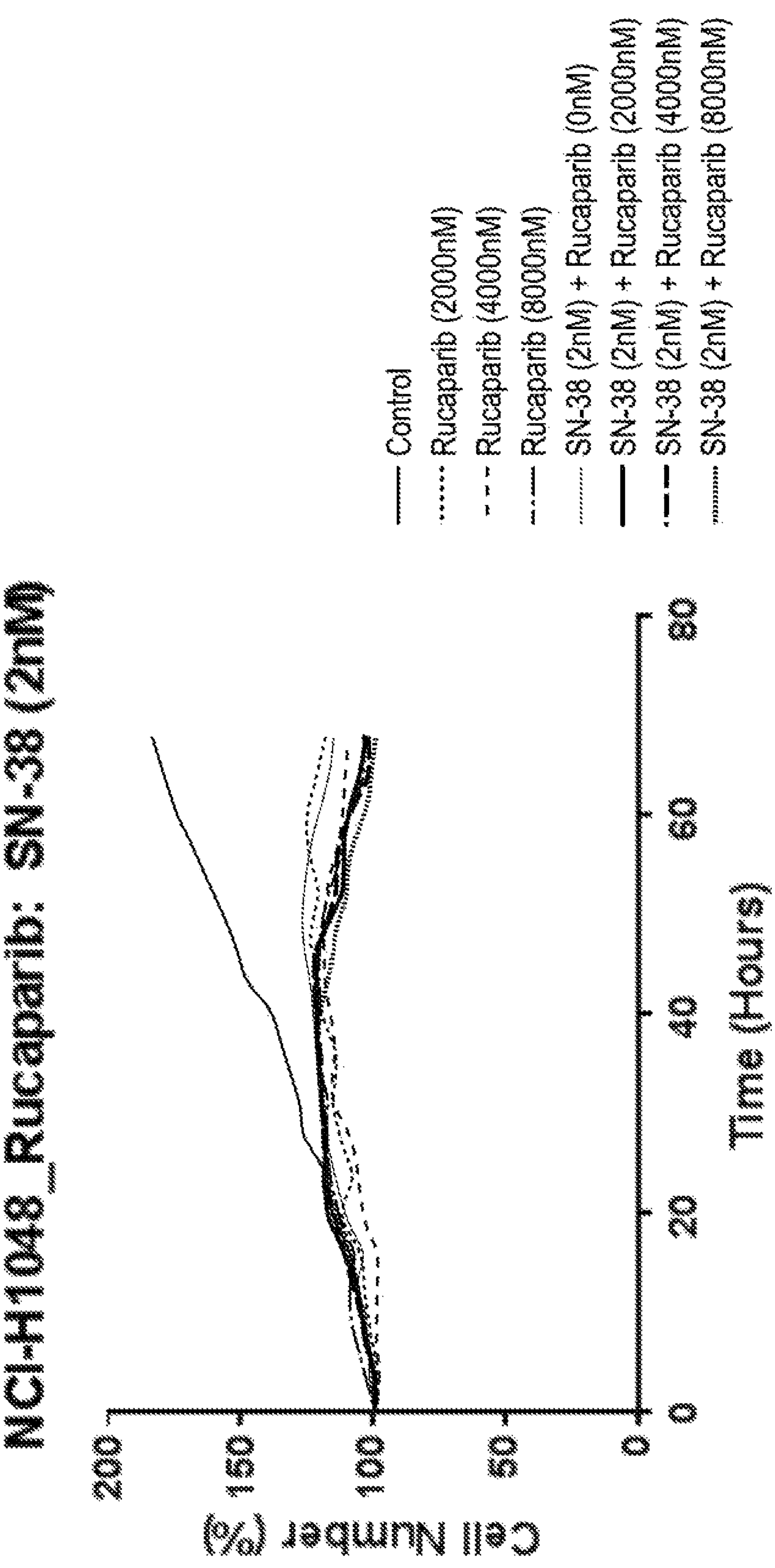
FIG. 2B is a graph showing the results of in vitro measurement of % cell number over time for NCI-H1048 small cell lung cancer cells treated with the topoisomerase inhibitor SN-38 and the PARP inhibitor rucaparib.

The NCI-H1048 SCLC cells were slow-growing and very sensitive to combinations of olaparib and rucaparib with SN-38 at 2 nM. FIG. 2B is a graph showing the results of in vitro measurement of % cell number over time for NCI-H1048 small cell lung cancer cells treated with the topoisomerase inhibitor SN-38 and the PARP inhibitor rucaparib.

Figure 2C:
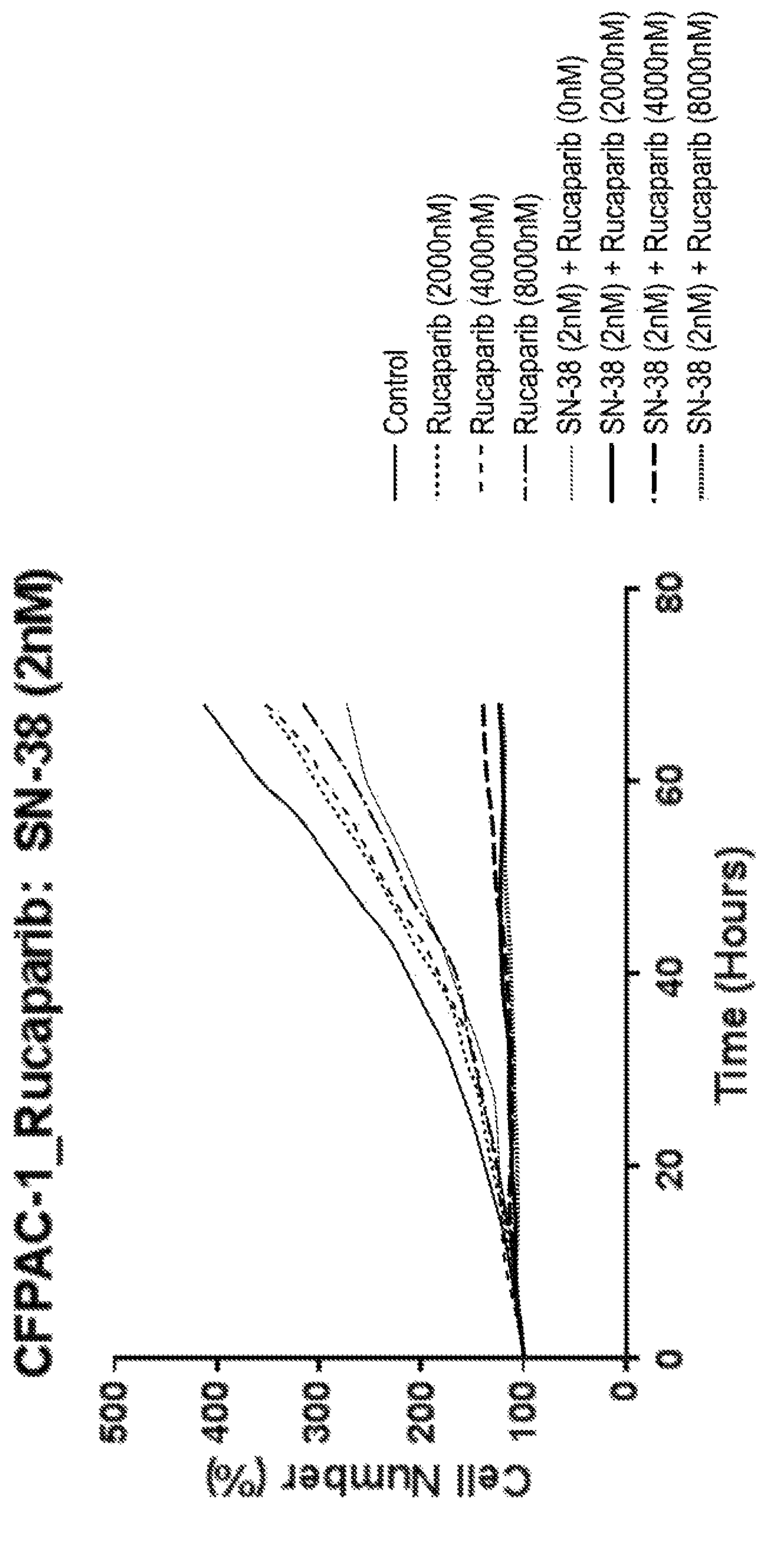
FIG. 2C is a graph showing the results of in vitro measurement of % cell number over time for CFPAC-1 pancreatic cancer cells treated with the topoisomerase inhibitor SN-38 and the PARP inhibitor rucaparib.

Additive/synergistic effects were observed between SN-38 at 2 nM combined with the tested PARP inhibitors olaparib, veliparib and rucaparib with CFPAC-1 pancreatic cancer cells. FIG. 2C is a graph showing the results of in vitro measurement of % cell number over time for CFPAC-1 pancreatic cancer cells treated with the topoisomerase inhibitor SN-38 and the PARP inhibitor rucaparib.

Figure 2D:
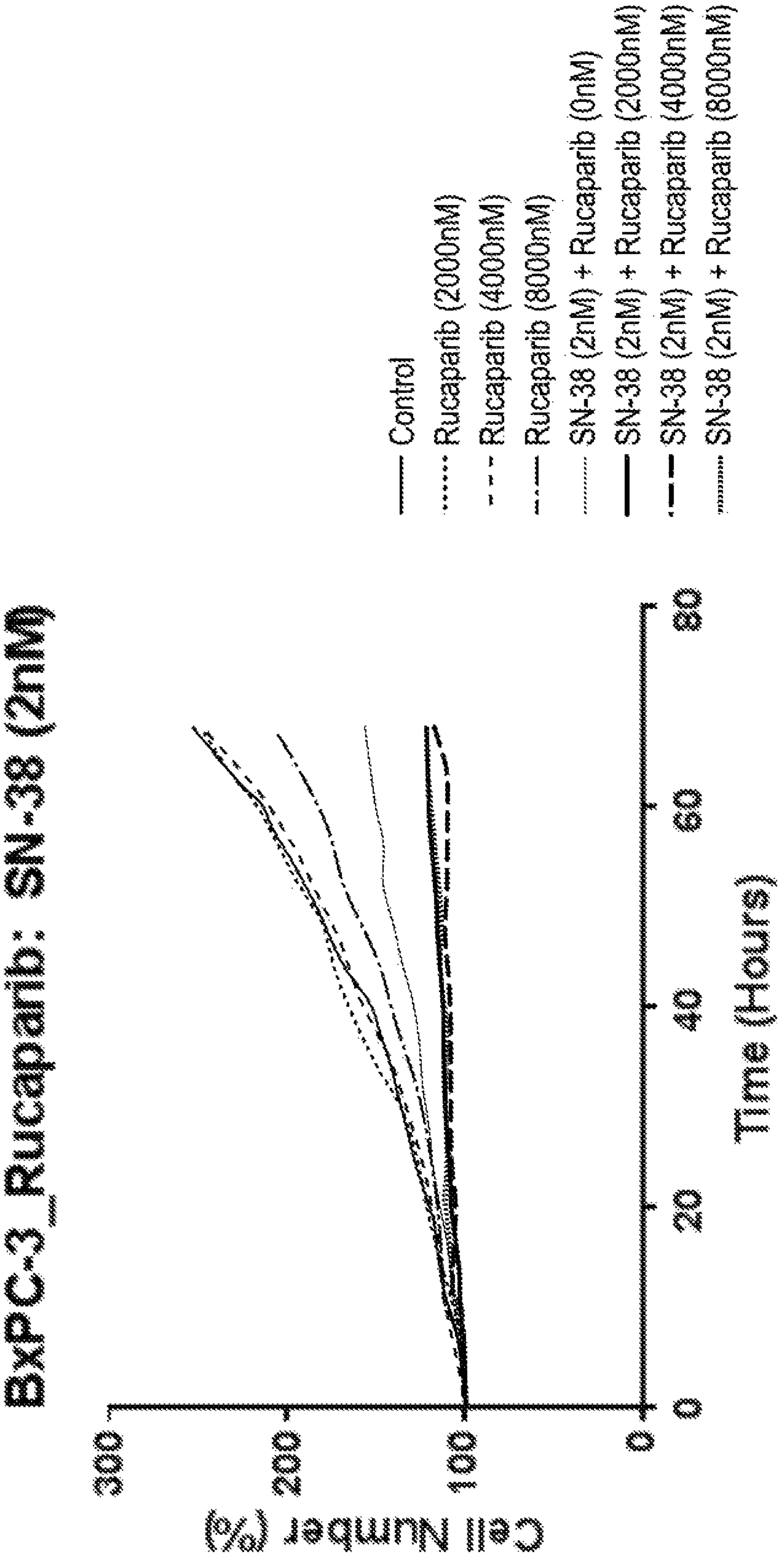
FIG. 2D is a graph showing the results of in vitro measurement of % cell number over time for BxPC-3 pancreatic cancer cells treated with the topoisomerase inhibitor SN-38 and the PARP inhibitor rucaparib.
Figure 2E:
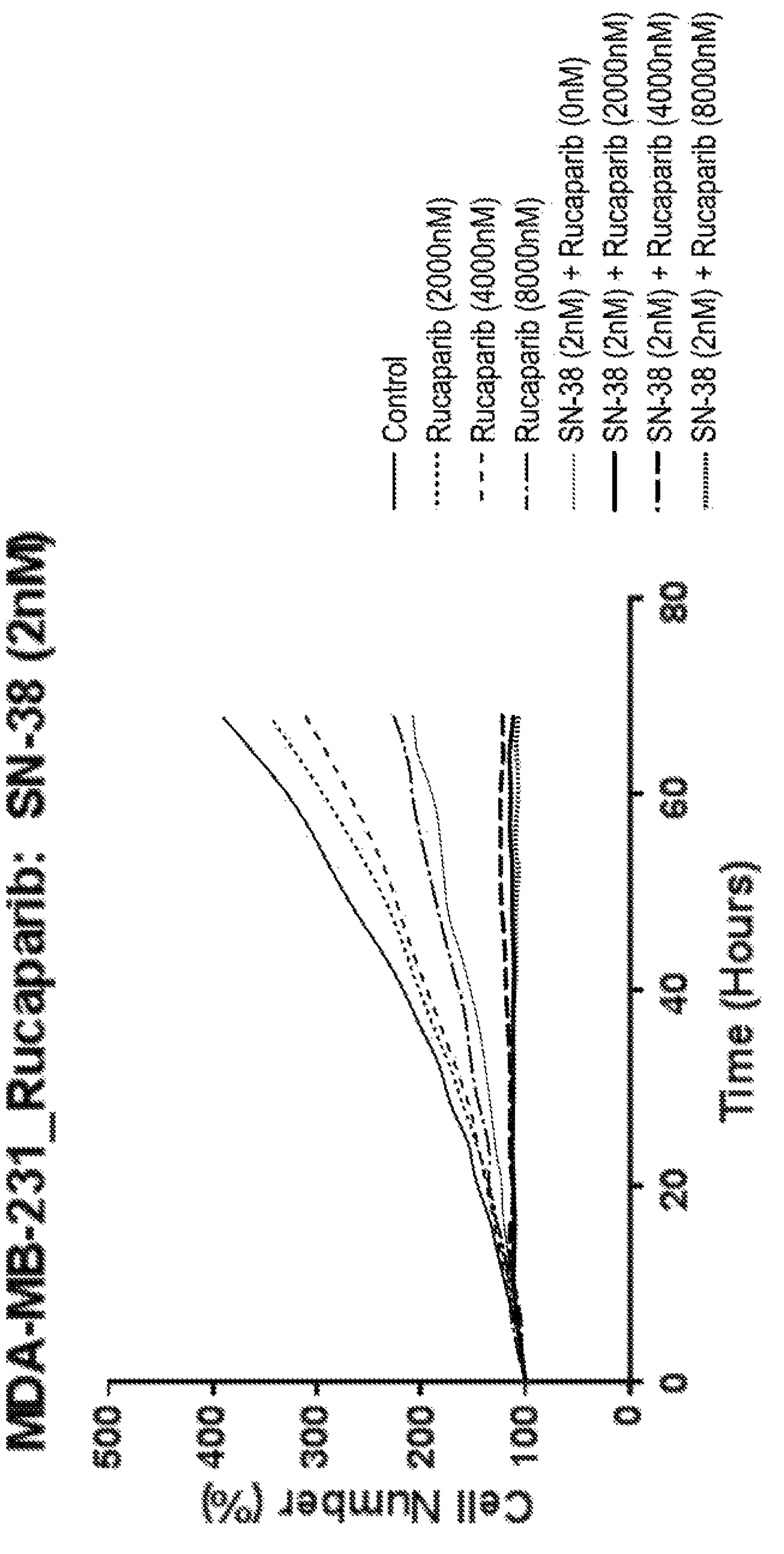
FIG. 2E is a graph showing the results of in vitro measurement of % cell number over time for MDA-MB-231 triple negative breast cancer (TNBC) cancer cells treated with the topoisomerase inhibitor SN-38 and the PARP inhibitor rucaparib.

FIG. 2D is a graph showing the results of in vitro measurement of % cell number over time for BxPC-3 pancreatic cancer cells treated with the topoisomerase inhibitor SN-38 and the PARP inhibitor rucaparib. FIG. 2E is a graph showing the results of in vitro measurement of % cell number over time for MDA-MB-231 triple negative breast cancer (TNBC) cancer cells treated with the topoisomerase inhibitor SN-38 and the PARP inhibitor rucaparib.

Figure 13A:
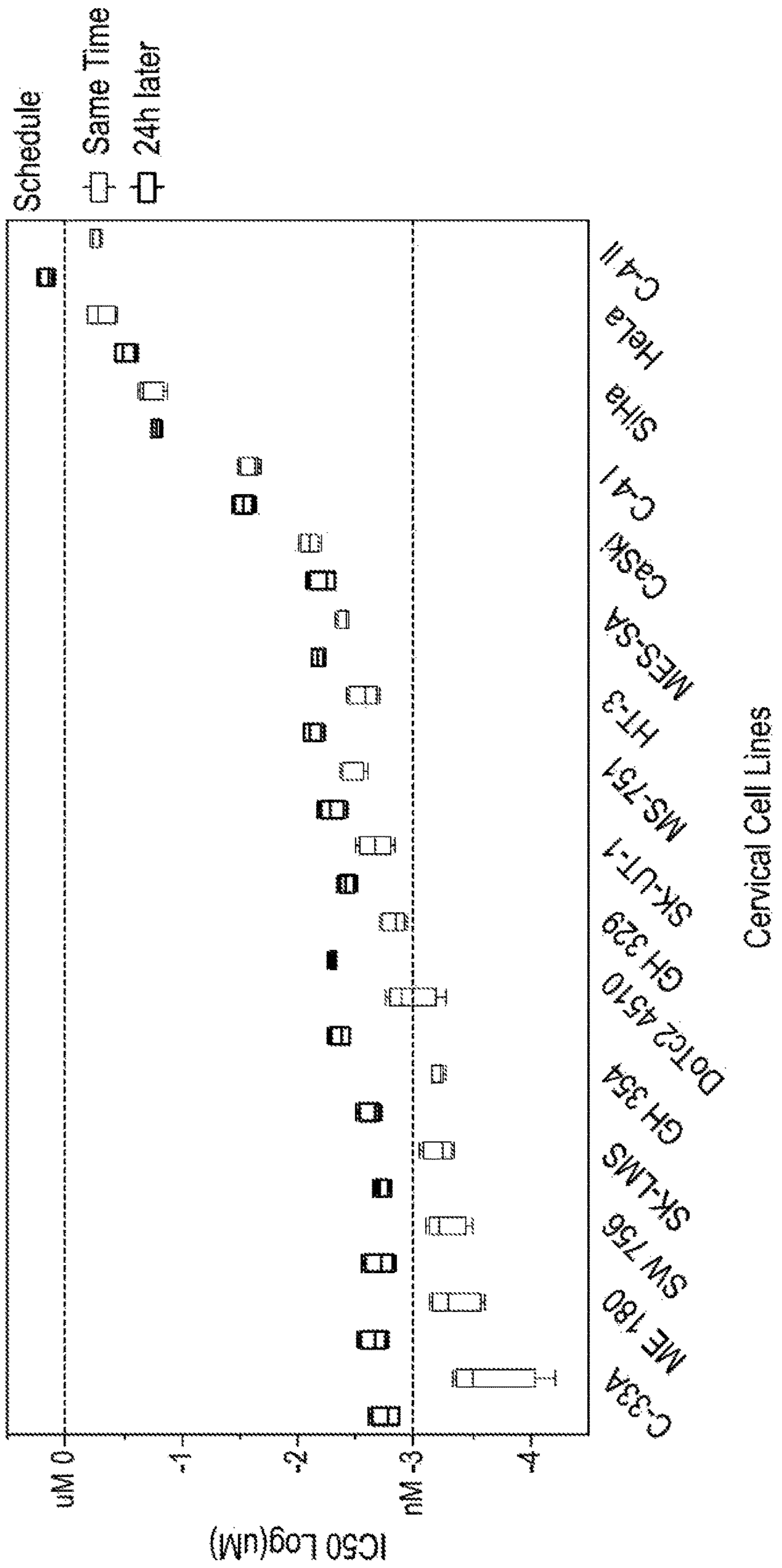
FIG. 13A is a graph showing the in vitro activity (IC50) for multiple cervical cancer cell lines treated with veliparib and SN38, added together or with the veliparib added 24 hours after the SN38.
Figure 13B:
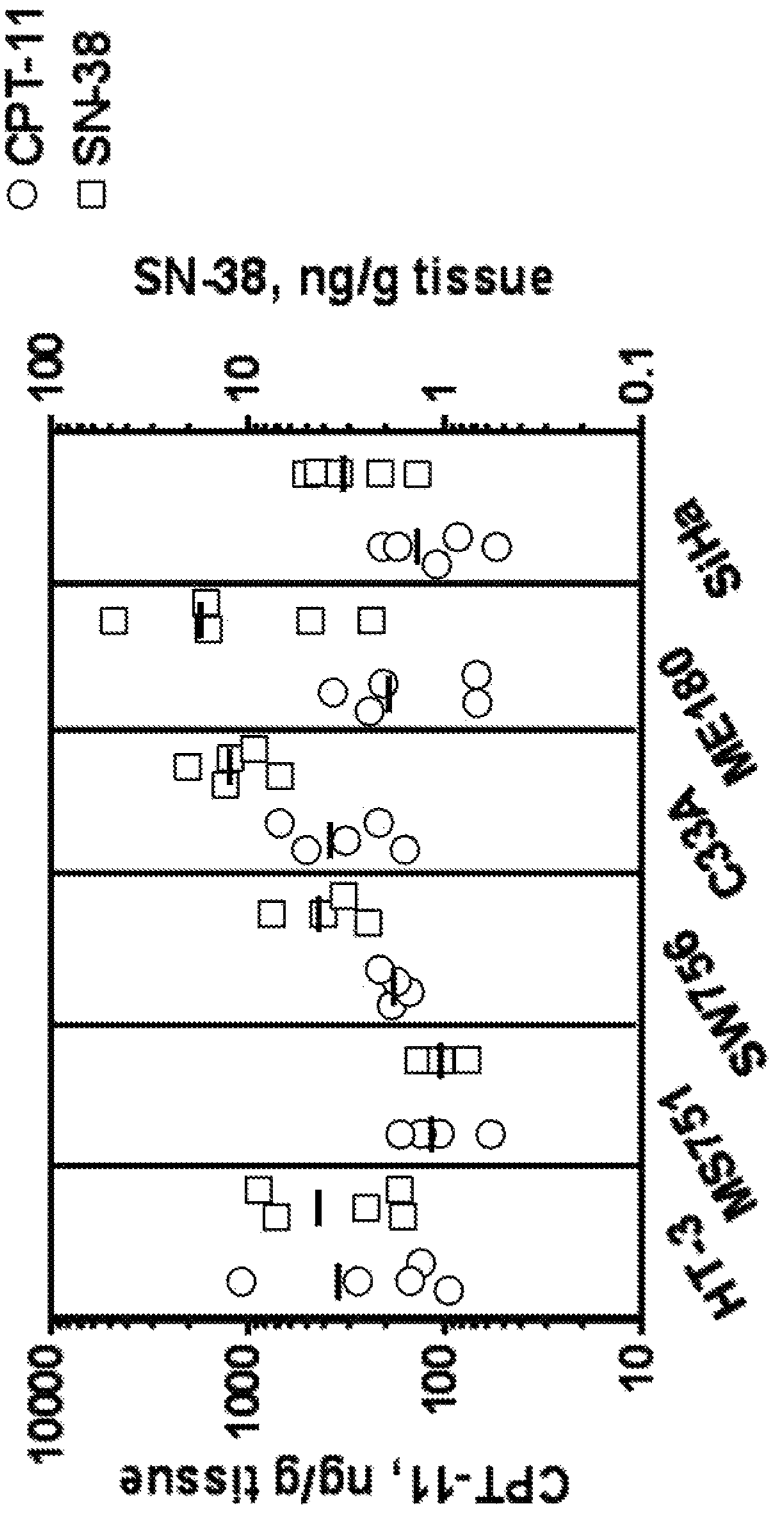
FIG. 13B is a graph showing the cell viability (CTG assay) in nude mice with cervical cancer tumors, injected with a single dose of MM-398 (10 mg/kg) followed by measurement of irinotecan and SN38 content in the tumor measured by LC-MS.

FIG. 13A depicts the in vitro activity of SN-38 in cervical models. Cervical cells lines were treated with veliparib and SN-38 at either the same time or with scheduling with Veliparib being added 24 h after SN-38, and cell viability was measured using CTG assay.

Example 2

Pre-Clinical Dose Tolerability Studies

Various pre-clinical in vivo experiments were conducted to evaluate delayed dosing of veliparib relative to liposomal irinotecan can alleviate systemic toxicity, including a pre-clinical dose tolerability study. The combination of veliparib and irinotecan has been plagued by dose-limiting toxicities that have prevented this combination from being dosed at high (effective) doses of each drug, thereby limiting its clinical utility. To address this problem, pre-clinical studies evaluated administering a liposomal preparation of a topoisomerase 1 inhibitor, followed by the administration of a PARP inhibitor at least 1 day (preferably 2-3 days) after the day on which the liposomal topoisomerase 1 inhibitor was administered.

The advantage of dosing with MM-398 compared to free irinotecan is the extended PK profile and prolonged local tumor exposure of MM-398. Since SN-38 is cleared more quickly from normal tissues than from tumor, delayed dosing of veliparib (e.g. starting veliparib dosing a few days after MM-398 administration) allows for the window of maximum irinotecan-induced toxicity to pass in the absence of concurrent veliparib toxicity. However, the tumor levels of SN-38 are sustained longer than in healthy tissue, such that upon PARP inhibitor dosing subsequent to liposomal Top1 inhibitor (e.g., MM-398) administration, both drugs will act on tumor tissue simultaneously.

Figures 5A, 5B, 5C:
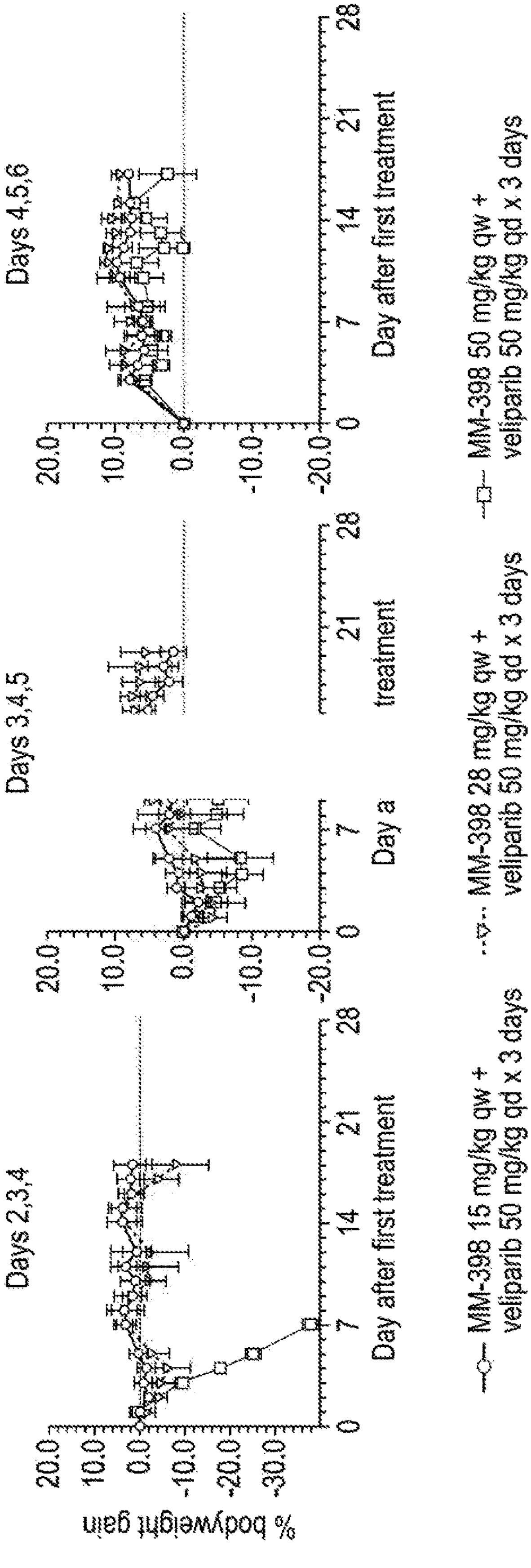
FIG. 5A is a graph showing the results of a murine tolerability study of a combination of MM-398 and veliparib, measuring % change in bodyweight after administration of 15 mg/kg of MM-398 on day 1, and 50 mg/kg of veliparib on days 2, 3, and 4.
FIG. 5B is a graph showing the results of a murine tolerability study of a combination of MM-398 and veliparib, measuring % change in bodyweight after administration of 28 mg/kg of MM-398 on day 1, and 50 mg/kg of veliparib on days 3, 4, and 5.
FIG. 5C is a graph showing the results of a murine tolerability study of a combination of MM-398 and veliparib, measuring % change in bodyweight after administration of 50 mg/kg of MM-398 on day 1, and 50 mg/kg of veliparib on days 4, 5, and 6.
Figure 6A:
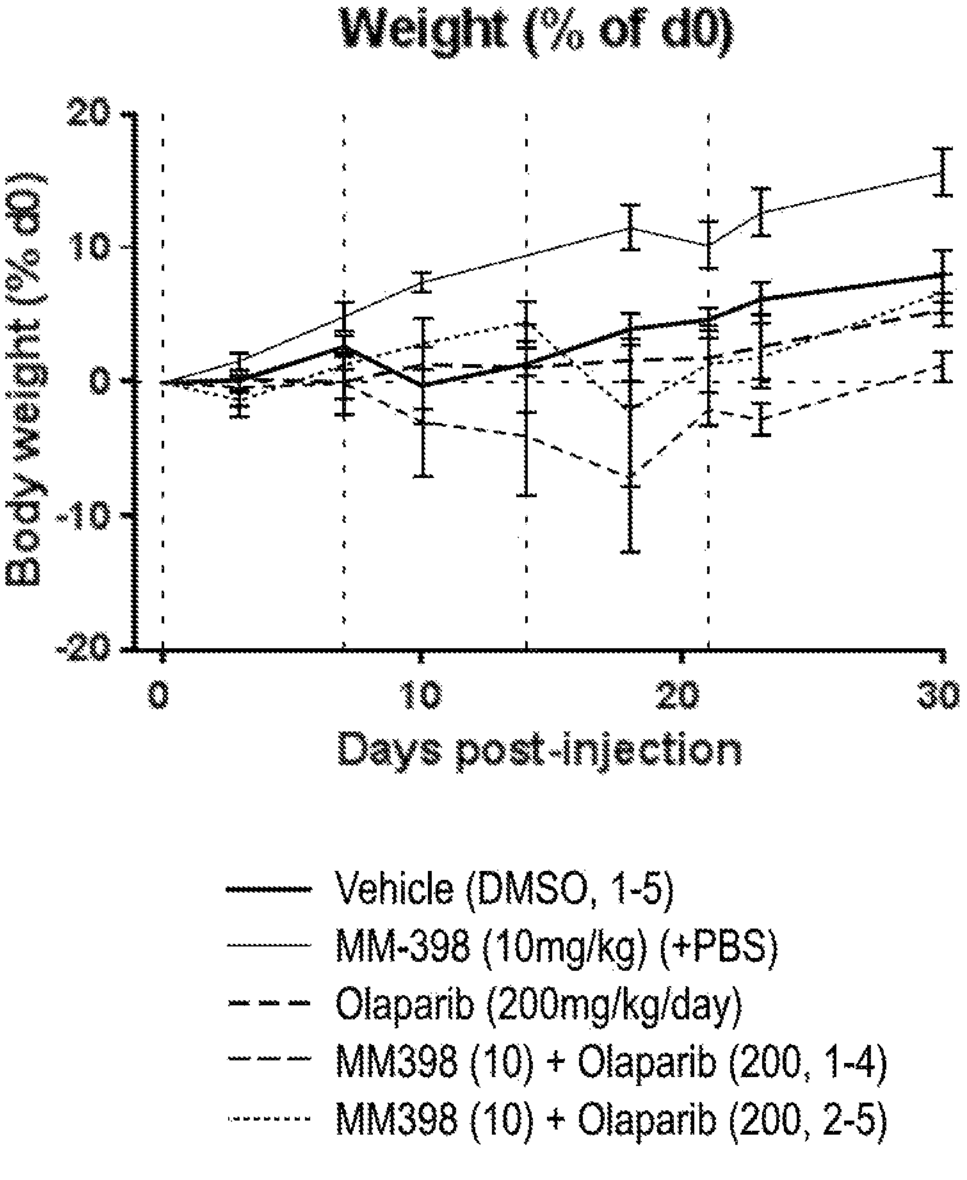
FIG. 6A is a graph comparing the results of a murine tolerability study measuring % change in bodyweight after administration of 10 mg/kg of MM-398 (+PBS); 200 mg/kg/day of Olaparib; 10 mg/kg of MM-398 (+PBS) with 200 mg/kg/day of Olaparib on days 1-4; and 10 mg/kg of MM-398 (+PBS) with 200 mg/kg/day of Olaparib on days 1-5.
Figure 6B:
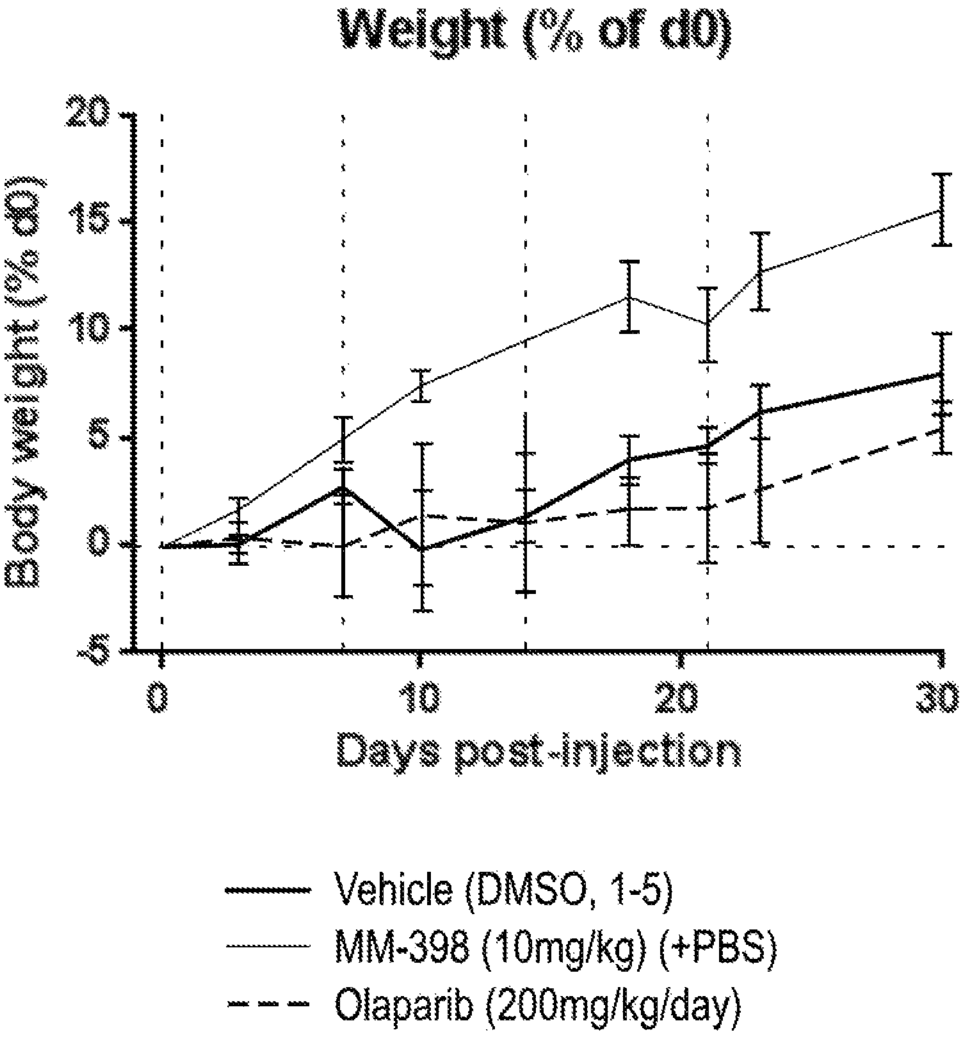
FIG. 6B is a graph comparing the results of a murine tolerability study measuring % change in bodyweight after administration of 10 mg/kg of MM-398 (+PBS) and 200 mg/kg/day of Olaparib.
Figure 6C:
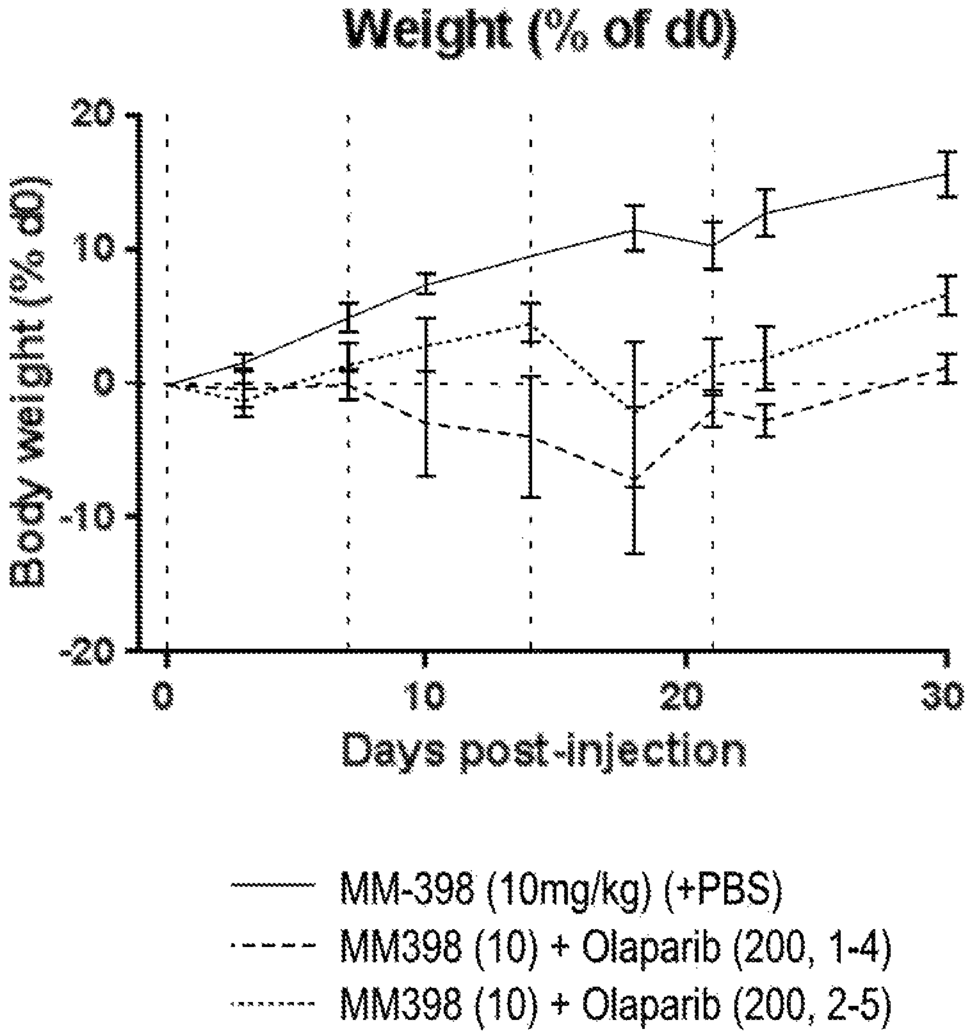
FIG. 6C is a graph comparing the results of a murine tolerability study measuring % change in bodyweight after administration of 10 mg/kg of MM-398 (+PBS); 10 mg/kg of MM-398 (+PBS) with 200 mg/kg/day of Olaparib on days 1-4; and 10 mg/kg of MM-398 (+PBS) with 200 mg/kg/day of Olaparib on days 1-5.
Figure 6D:
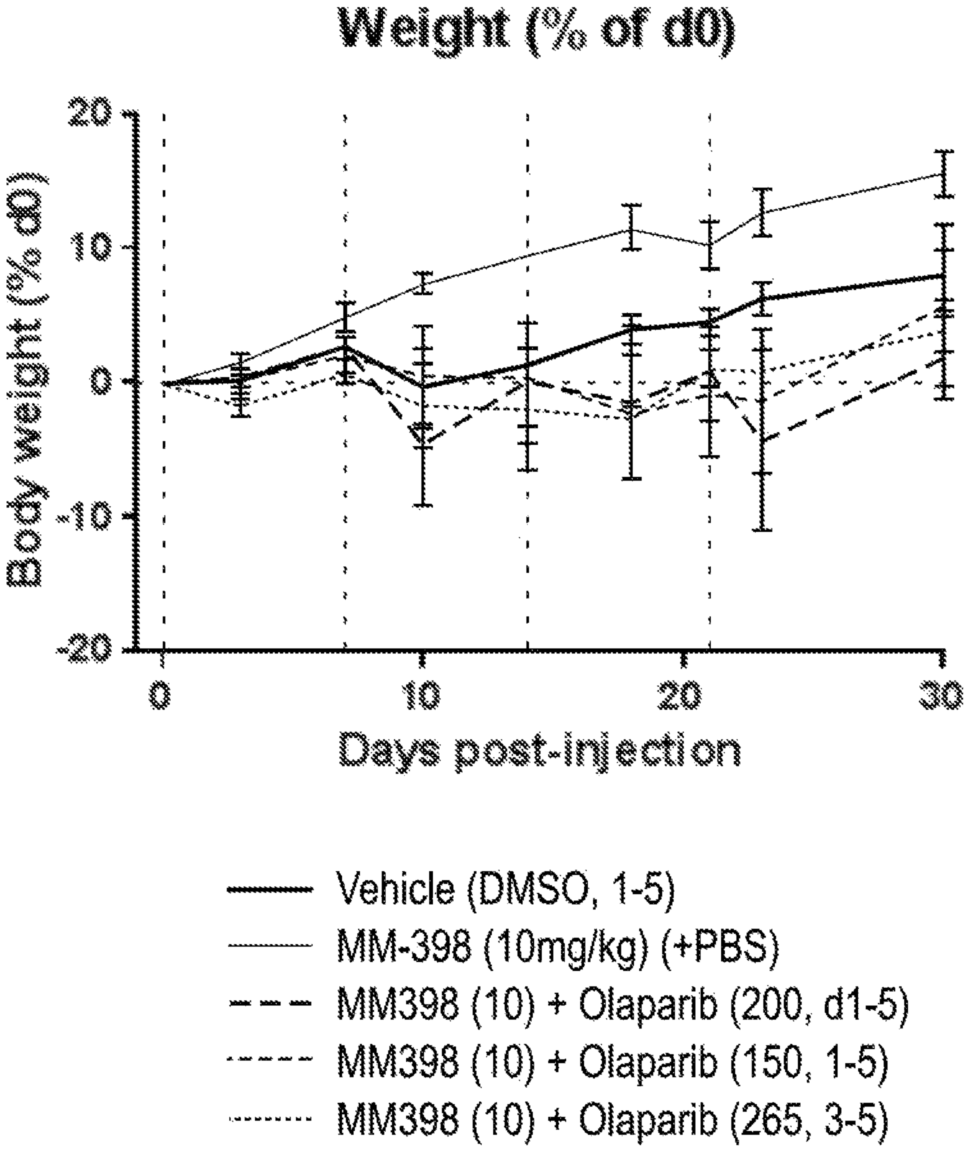
FIG. 6D is a graph comparing the results of a murine tolerability study measuring % change in bodyweight after administration of 10 mg/kg of MM-398 (+PBS); 10 mg/kg of MM-398 (+PBS) with 200 mg/kg/day of Olaparib on days 1-5; 10 mg/kg of MM-398 (+PBS) with 150 mg/kg/day of Olaparib on days 1-5; and 10 mg/kg of MM-398 (+PBS) with 265 mg/kg/day of Olaparib on days 3-5.

To demonstrate that delayed dosing of veliparib relative to nal-IRI can alleviate systemic toxicity, a pre-clinical dose tolerability study was performed. Mice were dosed chronically with nal-IRI once weekly at various doses on Day 1, while veliparib was dosed once daily at a fixed dose for 3 consecutive days each week (either on Days 2-4, Days 3-5, or Days 4-6), and body weight was followed as a gross measure of toxicity. All mice were dosed chronically once weekly on day 1, with veliparib subsequently dosed for 3 consecutive days either on days 2-4, days 3-5, or days 4-6. Mice were weighed daily and bodyweight gain is indicated on the Y-axis. Weight loss is indicative of intolerability of the combination. Notably, the highest (50 mg/kg) dose of MM-398 liposomal irinotecan was best tolerated (i.e., lowest measured reduction in % bodyweight observed over the experiment) when the veliparib was administered on days 4, 5 and 6 (FIG. 5C). Similarly, the combination of veliparib and MM-398 was best tolerated at lower MM-398 liposomal irinotecan doses when the veliparib was only administered on days 4, 5, and 6 after MM-398 administration. Toxicity of the combination was seen at the highest doses of MM-398 when given in close proximity to the veliparib doses (FIG. 5A). However, this toxicity could be alleviated either by dose reducing MM-398 or delaying the start of veliparib dosing, whereby the highest dose of MM-398 could be successfully dosed with veliparib if given on Days 4-6 following Day 1 dosing of MM-398. The Day 4-6 veliparib dosing schedule (following day 1 dosing of MM398) was followed in subsequent efficacy studies which demonstrated synergy of the combination in two cervical cancer tumor xenograft models, in which veliparib alone was not efficacious (FIG. 7A) and a second model in which neither MM-398 or veliparib were efficacious as single agents (FIG. 7B), however the combination demonstrated tumor growth inhibition (FIG. 7B).

Figure 4:
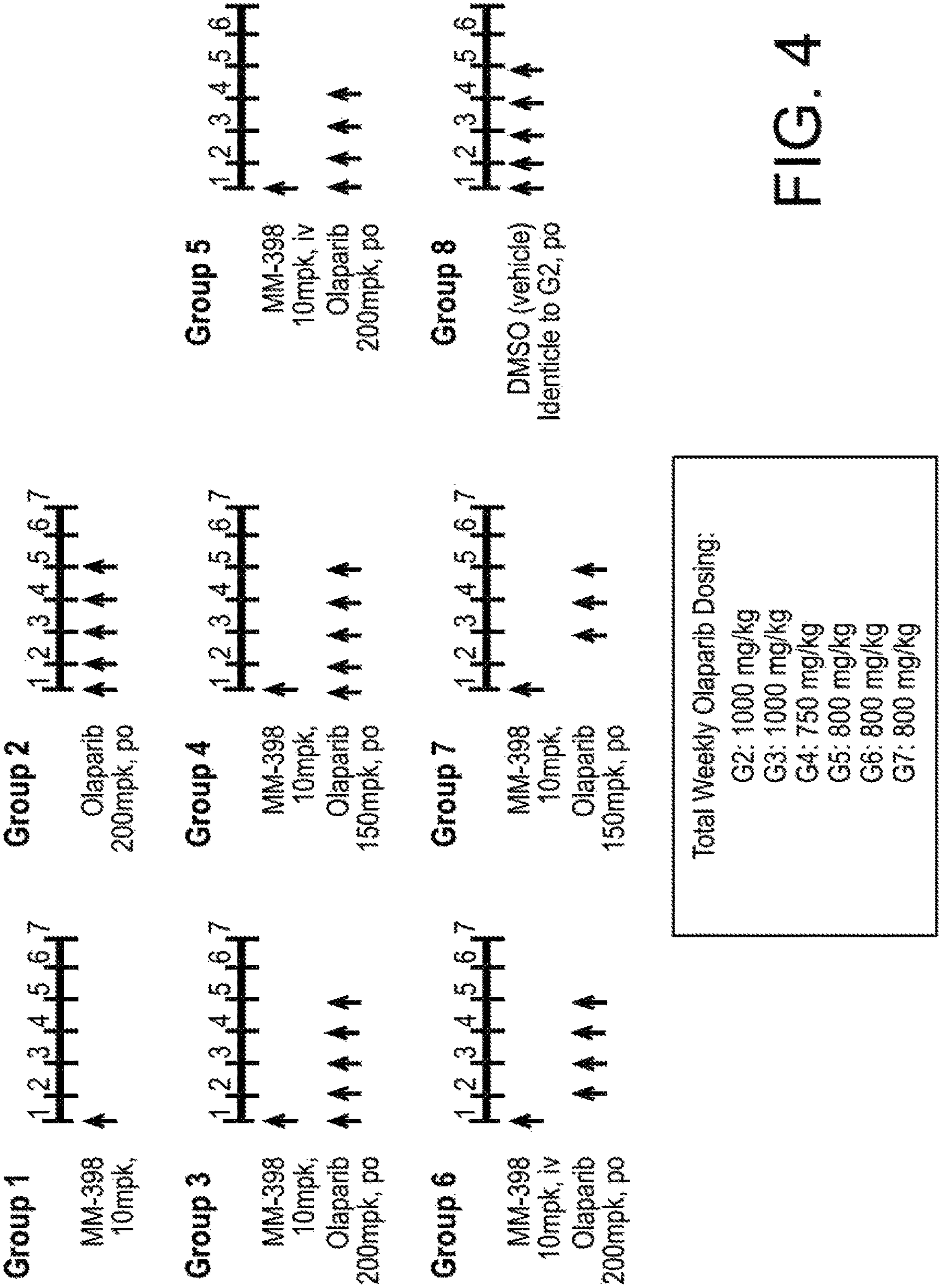
FIG. 4 depicts a graphical representation of a murine tolerability study design comparing MM-398 and olaparib as a monotherapy or in combination using a fixed dose of MM-398 and varying doses of olaparib, with various dosing schedules for different groups.

To exemplify an embodiment demonstrating that delayed dosing of olaparib relative to MM-398 can alleviate systemic toxicity, a pre-clinical dose tolerability study was performed. FIG. 4 depicts a graphical representation of a murine tolerability study design comparing MM-398 and olaparib as a monotherapy or in combination using a fixed dose of MM-398 and varying doses of olaparib, with various dosing schedules for different groups: Group 1: MM-398 alone IV (10 mg/kg); Group 2: olaparib alone oral (200 mg/kg); Group 3: MM-398 (d1)+olaparib (200 mg/kg, d1-5); Group 4: MM-398 (d1)+olaparib (150 mg/kg, d1-5; Group 5: MM-398 (d1)+olaparib (200 mg/kg, d1-4); Group 6: MM-398 (d1)+olaparib (200 mg/kg, d2-5); Group 7: MM-398 (d1)+olaparib (265 mg/kg, d3-5); group 8: DMSO alone oral (FIGS. 6A-6D). Mice that received monotherapy of MM-398, olaparib were dosed 5× weekly. Mice that received a combination of a constant concentration of MM-398 (10 mg/kg) and varying concentration of olaparib were dosed in varying schedules: Group 3: MM-398 (d1)+olaparib (200 mg/kg, d1-5); Group 4: MM-398 (d1)+olaparib (150 mg/kg, d1-5; Group 5: MM-398 (d1)+olaparib (200 mg/kg, d1-4); Group 6: MM-398 (d1)+olaparib (200 mg/kg, d2-5); Group 7: MM-398 (d1)+olaparib (200 mg/kg, d3-5). Mice were monitored for treatment dependent toxicities by charting body weight and percent survival. Addition of olaparib seemed to be more toxic as compared to monotherapy, however delaying start of olaparib administration to d3 seemed to decrease olaparib specific toxicity as compared to concurrent therapy. Mice were dosed chronically with MM-398 once weekly at various doses on Day 1, while olaparib was dosed once daily at a weekly fixed dose for 5, 4 or 3 consecutive days each week (either on Days 1-5, Days 1-4, Days 2-5 or Days 3-5), and body weight and percent survival were followed as a gross measure of toxicity. Toxicity of the combination was seen at the highest doses of MM-398 when given in close proximity to the olaparib doses (FIG. 4). However, this toxicity could be alleviated either by delaying the start of olaparib dosing, whereby the highest dose of MM-398 could be successfully dosed with olaparib if given on Days 3-5 following Day 1 dosing of MM-398.

Mice were dosed chronically with MM-398 once weekly at various doses on Day 1, while veliparib was dosed once daily at a fixed dose for 3 consecutive days each week (either on Days 2-4, Days 3-5, or Days 4-6) and body weight was followed as a gross measure of toxicity. Toxicity of the combination was seen at the highest doses of nal-IRI when given in close proximity to the veliparib doses. However, this toxicity could be alleviated either by dose reducing nal-IRI or delaying the start of veliparib dosing. This dosing schedule was followed in subsequent mouse efficacy studies which demonstrated synergy of the combination in two cervical cancer tumor xenograft models, in which veliparib alone was not efficacious, and a second model in which neither nal-IRI or veliparib were efficacious as single agents, however the combination demonstrated tumor growth inhibition.

Figure 8A:
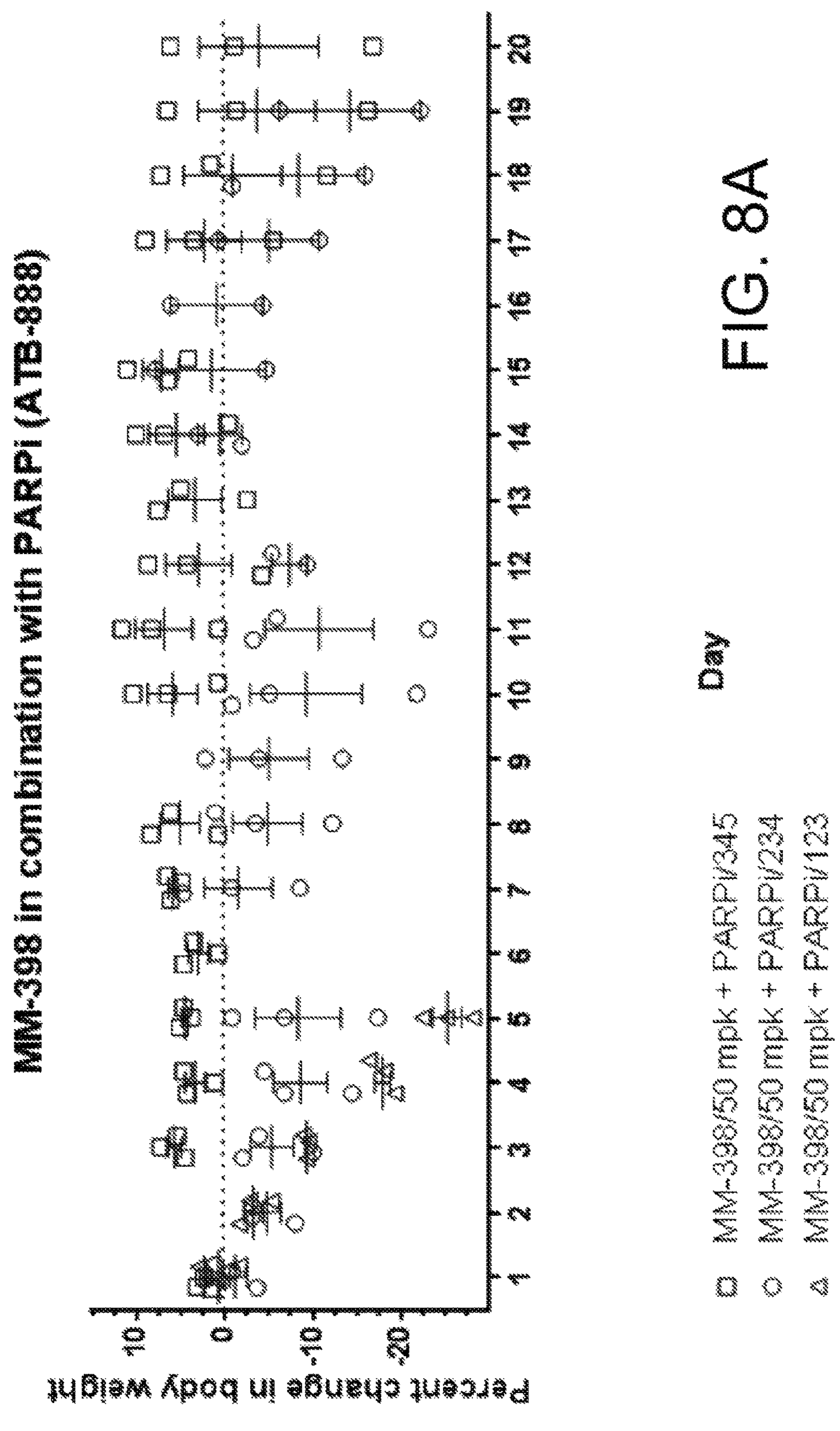
FIG. 8A is a graph that depicts the in vivo tolerability of 50 mg/kg dose of MM-398 in combination with 50 mg/kg veliparib given on days 1, 2, and 3; or 2, 3, and 4; or 3, 4, and 5 after administration of the MM-398.
Figure 8B:
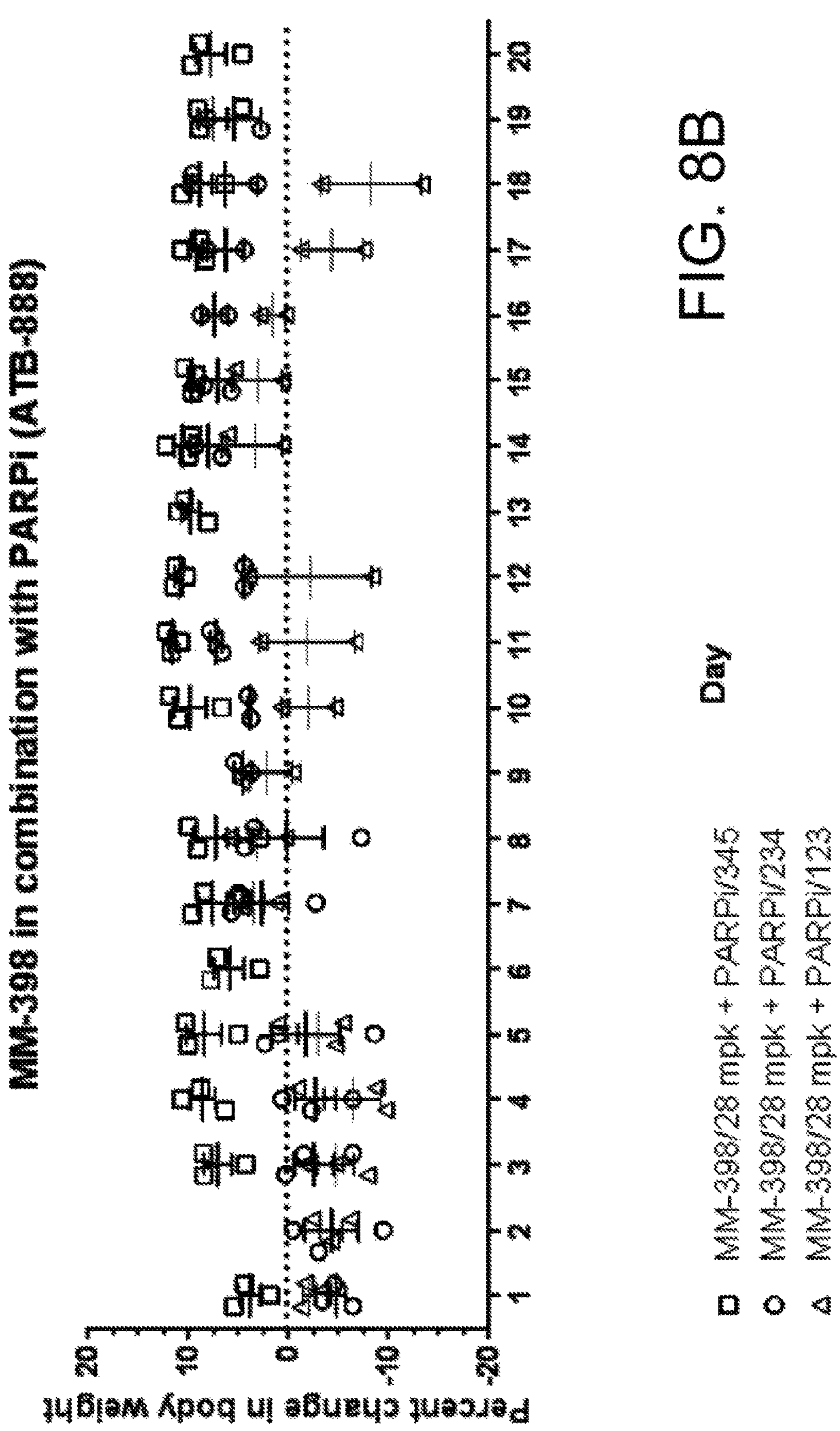
FIG. 8B is a graph that depicts the in vivo tolerability of 28 mg/kg dose of MM-398 in combination with 50 mg/kg veliparib given on days 1, 2, and 3; or 2, 3, and 4; or 3, 4, and 5 after administration of the MM-398.

The tolerability of the combination of MM398 in a mouse model on day 1 was evaluated in combination with the administration of veliparib on days 1-3, days 2-4 and days 3-5. The tolerability of the combined regimen in mice (measured by change in percent bodyweight over 20 days) increased as the first administration of the veliparib occurred on day 2 and day 3, with day 3 initial veliparib dosing providing the most tolerated dosing schedule. FIG. 8A is a graph that further depicts the in vivo tolerability of the 50 milligrams/kilogram (mpk) dose of MM-398 on day 1 in combination with 50 mg/kg veliparib given on days 1, 2, and 3; or days 2, 3, and 4; or days 3, 4, and 5 after administration of the MM-398, as reflected in percent change in body weight with an adjusted lower limit. FIG. 8B is a graph that further depicts the in vivo tolerability of the 28 mpk dose of MM-398 on day 1 in combination with 50 mg/kg veliparib given on days 1, 2, and 3; or days 2, 3, and 4; or days 3, 4, and 5 after administration of the MM-398, as reflected in percent change in body weight with an adjusted lower limit.

Figure 12:
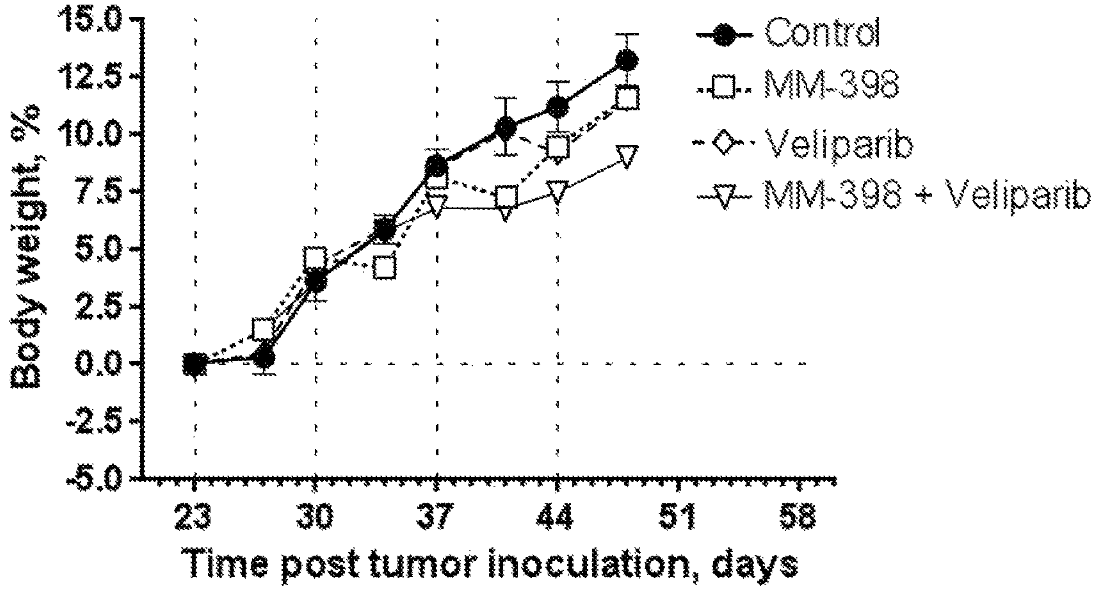
FIG. 12 depicts the effect of MM-398 in combination with veliparib in C33A xenograft model and body weight, where veliparib was dosed 72 h following liposomal irinotecan (5 mg/kg MM398) and/or the PARP inhibitor veliparib (50 mpk) on days 3-5 starting after administration of MM398.

FIG. 12 is a graph showing that treatment of mice with the combination of MM-398 with veliparib in C33A xenograft model described in Example 4 also lead to decreases in body weight as compared to administration of either drug alone.

These studies demonstrated that this toxicity could be alleviated by delaying the start of PARP inhibitor dosing, preferably by 2-3 days after the day on which liposomal irinotecan was administered. A dosing schedule where the PARP inhibitor was only administered on days subsequent to administration of liposomal irinotecan was followed in mouse efficacy studies (Example 3) demonstrating therapeutic synergy of the combination of a PARP inhibitor and liposomal irinotecan in two cervical cancer tumor xenograft models (in which veliparib alone was not efficacious, and a second model in which neither MM-398 or veliparib were efficacious as single agents, however the combination demonstrated tumor growth inhibition).

Example 3

Pre-Clinical Efficacy of Liposomal Irinotecan

In vivo tumor xenograft studies demonstrated that the efficacy of liposomal irinotecan is greater than free irinotecan. In addition, in vivo tumor xenograft studies demonstrated MM-398 is related to high CES activity and/or high tumor levels of CPT-11 following dosing with MM-398. Additionally, MM-398 has demonstrated superior activity compared to equivalent dosing of free irinotecan in several pre-clinical models including breast, colon, ovarian, and pancreatic tumor xenograft models.

Liposomal irinotecan (MM-398) has greater efficacy in various cancer models, compared to non-liposomal irinotecan. Cancer cells were implanted subcutaneously in mice; when tumors were well established and had reached mean volumes of 200 mm3, IV treatment with free irinotecan, MM-398 or control was initiated. The doses of free and nanoliposomal irinotecan used in each study are indicated above, with dose time points indicated by arrows. Tumor permeability as well as tumor tissue carboxylesterase (CES) activity, which is responsible for the enzymatic conversion of CPT-11 to SN-38, are predicted to be critical factors for local tumor exposure of SN-38 following MM-398 dosing. In vivo tumor xenograft studies have demonstrated that efficacy of MM-398 is related to high CES activity and/or high tumor levels of CPT-11 following dosing with MM-398. Additionally, MM-398 has demonstrated superior activity compared to equivalent dosing of free irinotecan in several pre-clinical models including breast, colon, ovarian, and pancreatic tumor xenograft models.

Example 4

Pre-Clinical Activity of Liposomal Irinotecan and PARP Inhibitors

Figure 7A:
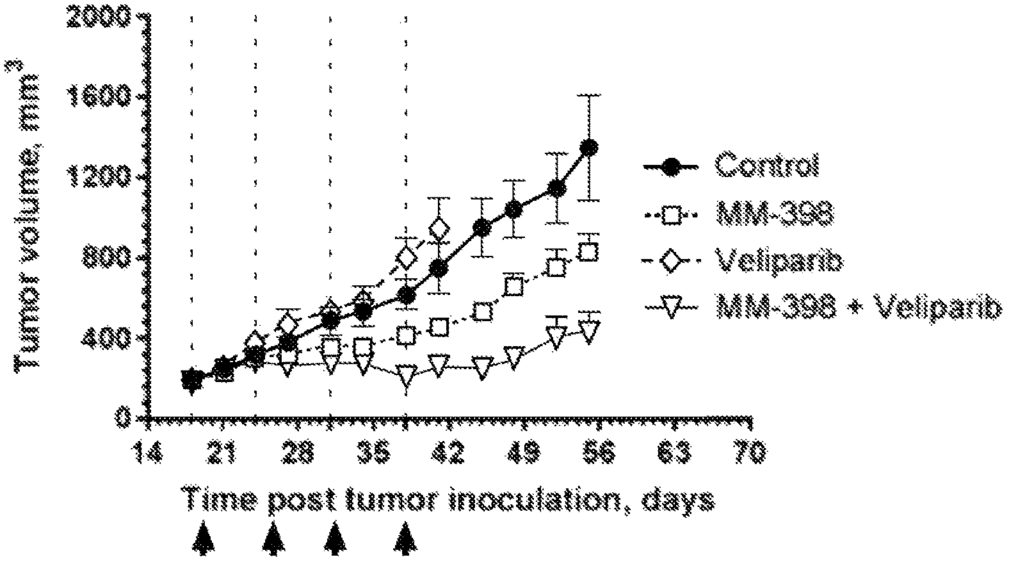
FIG. 7A is a graph showing data from a mouse xenograft study using MS751 cervical cancer cells in a murine model treated with liposomal irinotecan (5 mg/kg MM398) and/or the PARP inhibitor veliparib on days 4-6 after administration of MM398.
Figure 7B:
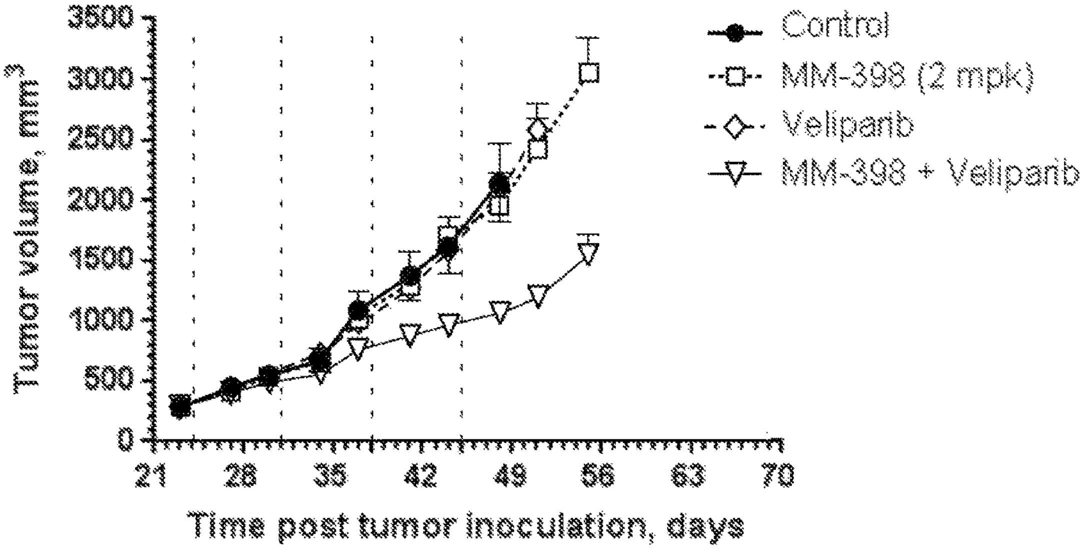
FIG. 7B is a graph showing data from a mouse xenograft study using MS751 cervical cancer cells in a murine model treated with liposomal irinotecan (2 mg/kg MM398) and/or the PARP inhibitor veliparib on days 4-6 after administration of MM398.

Referring to FIG. 7A and FIG. 7B, the antitumor activity of MM-398 was studied in combinations with veliparib (PARPi) in multiple cervical xenograft models. In this study. MS-751 and C33A xenograft models of cervical cancer were employed to probe the effect of administering suboptimal doses of MM-398 in combination with the PARP inhibitor veliparib. Differential tissue levels of MM-398 at 24 and 72 hours indicated that MM-398 and the active metabolite SN-38 cleared faster from the liver, spleen, colon, and plasma, than from tumors. The combination of veliparib and MM-398 gave improvements in key PD biomarkers (cleaved caspase and yH2AX) when compared to veliparib or MM-398 alone. FIGS. 7A and 7B show that the combination of MM-398+veliparib is synergistic. Two different cervical cancer xenograft models were utilized to study the efficacy of MM-398 dosed once weekly on Day 1 (arrows), veliparib dosed at 50 mg/kg orally once daily for 3 consecutive days on Days 4-6 of each week, or the combination dosed on the same schedule as the single agent treatments combined. (A) MS751 cervical cancer xenograft model using MM-398 dosed at 5 mg/kg and (B) C33A cervical cancer xenograft model using MM-398 dosed at 2 mg/kg. In the study, control mice were the same strain, and were harvested prior to tested mice (slightly younger). Data is not presented for mice removed from study for weight loss or for mice removed unintentionally before end date.

Cervical MS-751 Xenograft Model

The MS-751 Xenograft Model details are summarized in Table 6.

TABLE 6

Mouse strain: Nude (Tacoma)
Tumor Cervical MS-751, C33A
Inoculation: 5*10^6 (s.c.) in 30% MG
Drug: MM-39 (iv) + Veliparib (oral)

| Groups: | | Animal per group: | Dose (mpk) | |
|---|---|---|---|---|
| 1 | Saline | 10 | | |
| 2 | MM-398 | 10 | 5 | |
| 3 | veliparib/oral | 10 | 50 | 3/4/5th day |
| 4 | MM-398 + veliparib | 10 | 5 + 50 | 3/4/5th day |

Figure 9A:
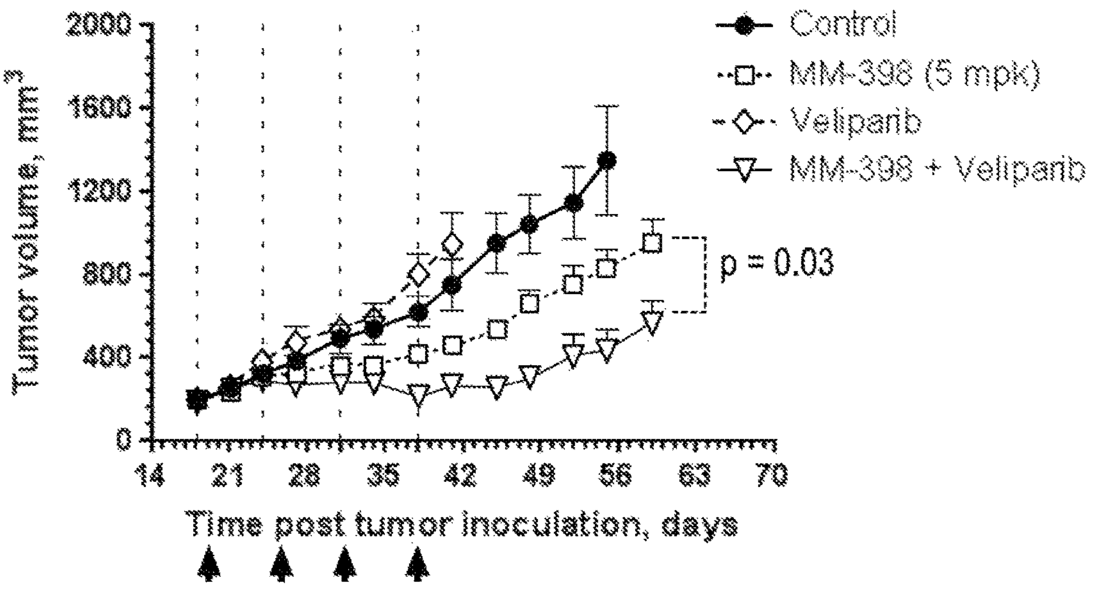
FIG. 9A is a graph showing data from a mouse xenograft study using MS751 cervical cancer cells in a murine model treated with liposomal irinotecan (5 mg/kg MM398) and/or the PARP inhibitor veliparib (50 mpk) on days 3-5 starting after administration of MM398.
Figure 9B:
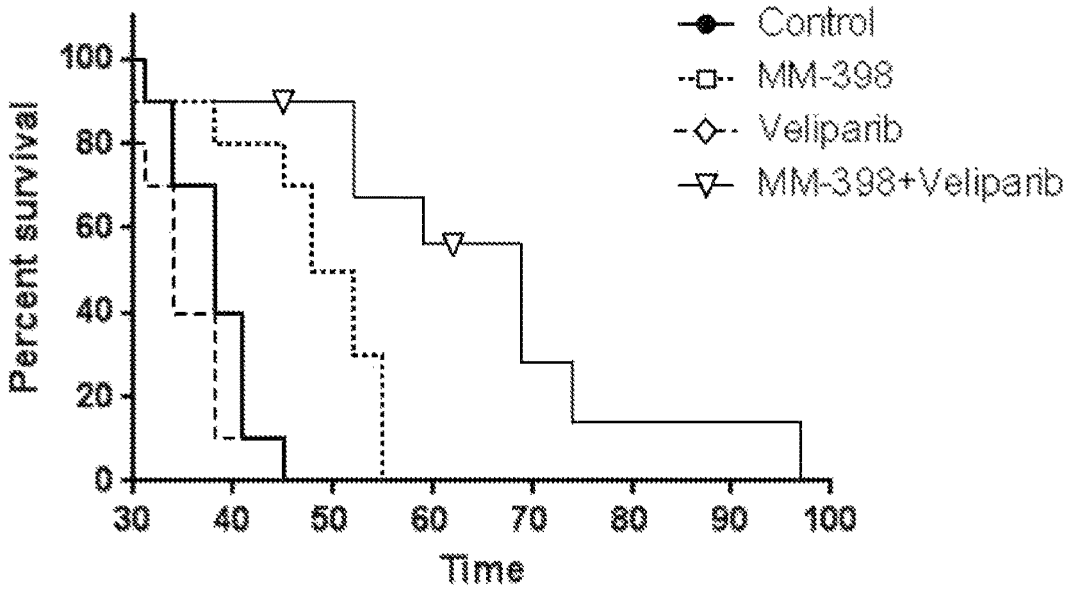
FIG. 9B is a graph showing survival data from a mouse xenograft study using MS751 cervical cancer cells in a murine model treated with liposomal irinotecan (5 mg/kg MM398) and/or the PARP inhibitor veliparib (50 mpk) on days 3-5 starting after administration of MM398.
Figure 9C:
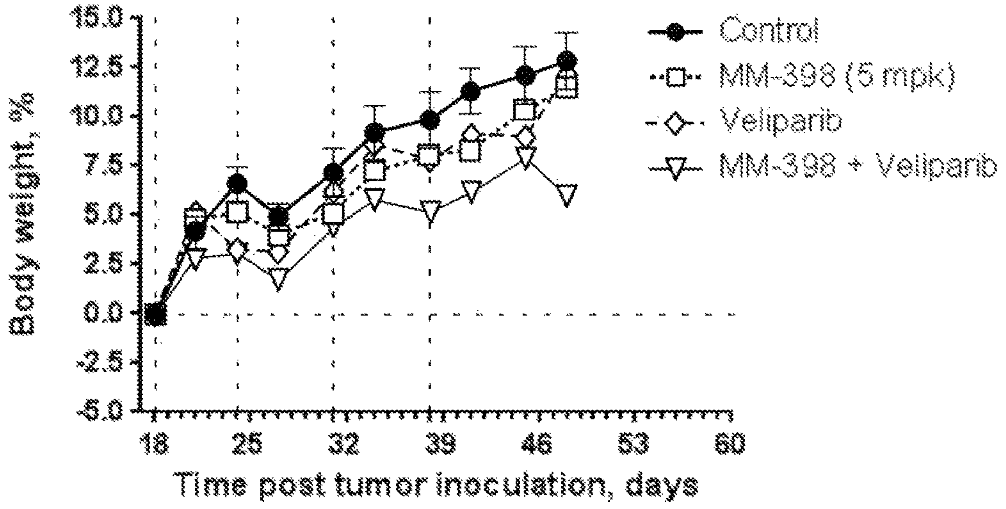
FIG. 9C is a graph that depicts the effect of MM-398 in combinations with veliparib in MS751 xenograft murine model treated with liposomal irinotecan (5 mg/kg MM398) and/or the PARP inhibitor veliparib (50 mpk) on days 3-5 starting after administration of MM398.

FIG. 9A shows that minor volume decreased when MM-398 (5 mpk dose) was administered in combinations with veliparib in the MS751 xenograft model (p=0.03) as compared to administration of either drug alone. FIG. 9B shows that percent survival was better for mice treated with MM-398 (5 mpk dose) in combinations with veliparib in MS751 xenograft model as compared to treatment with either drug alone either drug administered alone. FIG. 9C shows that treatment with the combination of MM-398 with veliparib in MS751 xenograft model lead to decreases in body weight as compared to administration of either drug alone.

C33A Cervical Xenograft Model

The C33A Xenograft Model details are summarized in Table 7.

TABLE 7

Mice: Female, Ncr Nudes (Taconic), 5-6 weeks.
Cell Lines: C33 A
Tumor Inoculation: 5 × $10^6$ in 100 μl Matrigel (30 vol %) sc
15 mice per a cell line

| Groups: | Dose, mpk: |
|---|---|
| MM-398 alone | 2 |
| Veliparib alone | 50 |
| MM-398 + Veliparib (3-4-5 d) | 2 + 60 |

TABLE 7-continued

Mice: Female, Ncr Nudes (Taconic), 5-6 weeks.
Cell Lines: C33 A
Tumor Inoculation: 5 × $10^6$ in 100 μl Matrigel (30 vol %) sc
15 mice per a cell line

| Groups: | Dose, mpk: |
|---|---|
| End-life Collection: 72 h after first injection | |
| Frozen (Tumor, Liver, Spleen, Plasma) | |
| FFPA (Tumor) | |
| Analysis: | |
| gamma H2AX and cleaved caspase/Tunnel in FFPE (Lia) | |
| CPT-11 and SN-38 in all tissues or MM-398 flash frozen only (Roswell) | |

Figure 10:
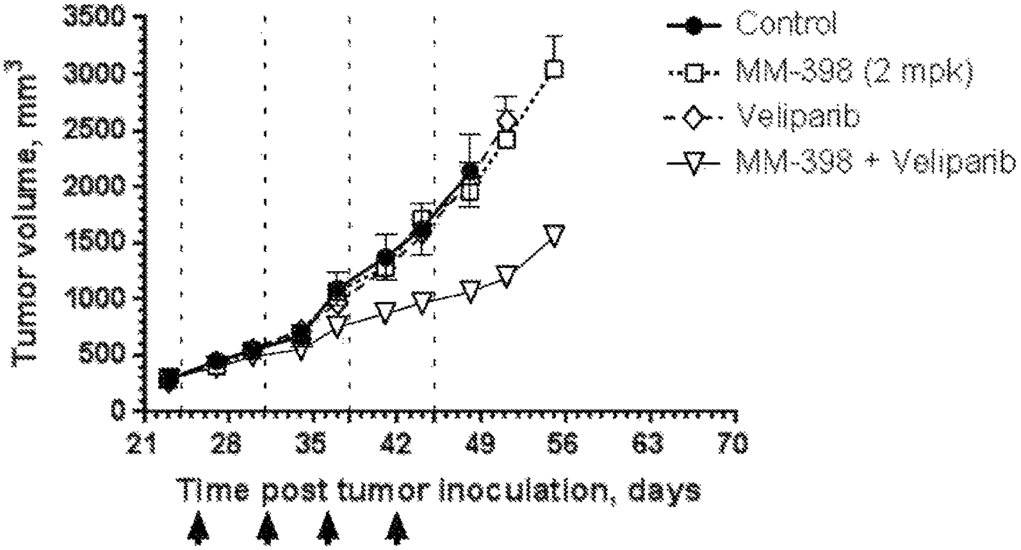
FIG. 10 is a graph showing data from a mouse xenograft study using C33 cervical cancer cells in a murine model treated with liposomal irinotecan (2 mg/kg MM398) and/or the PARP inhibitor veliparib (50 mpk) on days 3-5 starting after administration of MM398.
Figure 11:
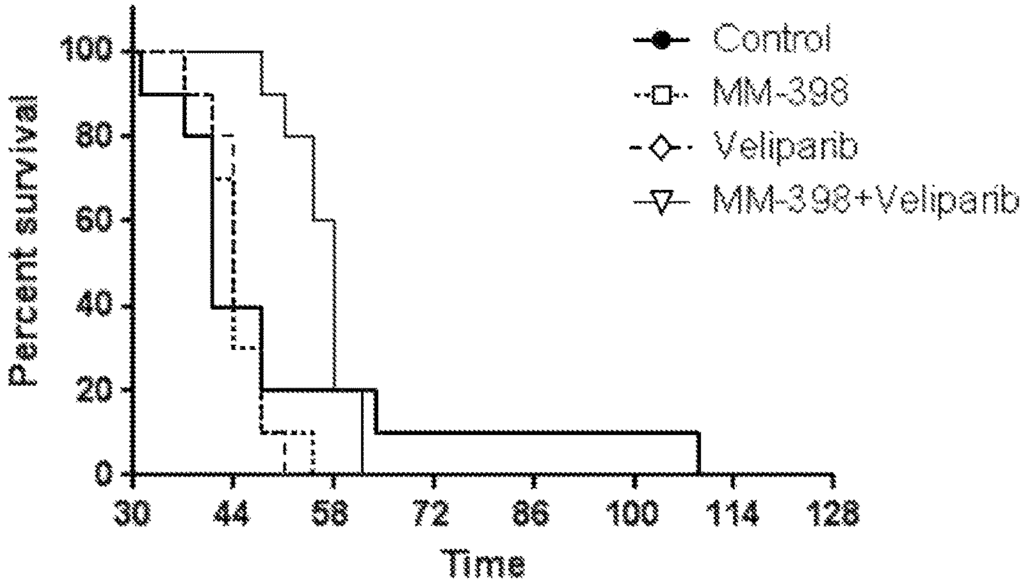
FIG. 11 is a graph showing survival data from a mouse xenograft study using C33 cervical cancer cells in a murine model treated with liposomal irinotecan (5 mg/kg MM398) and/or the PARP inhibitor veliparib (50 mpk) on days 3-5 starting after administration of MM398.

FIG. 10 shows that the combination of MM-398 with veliparib in the C33A xenograft model leads to decreases in tumor volume as compared to either drug alone administered alone. FIG. 11 shows that percent survival was better for mice MM-398 (5 mpk dose) in combinations with veliparib in C33A xenograft model as compared to either drug administered alone.

Example 5

Clinical Use of Liposomal Irinotecan and PARP Inhibitors

Clinical Use of Liposomal Irinotecan and Veliparib

This is a Phase 1 human dose escalation study to characterize the safety, tolerability, MTD and PK of MM-398 in combination with veliparib in order to determine an optimal combination dose and schedule that will be identified as the recommended Phase 2 dose. The following schematic outlines two different schedules of veliparib dosing that will be explored in combination with MM-398 bi-weekly dosing:

MM-398 will be administered by intravenous (IV) infusion over 90 minutes at a dose of 80 mg/$m^2$ every two weeks. MM-398 is administered by intravenous (IV) infusion over 90 minutes at a dose of 80 mg/$m^2$ (salt) irinotecan once every two weeks (days 1 and 15 of each 28-day treatment cycle). Veliparib is co-administered orally twice daily by the patient at home according to the following schedule:

Table 8

| Dose Level[1] | Veliparib Dose (mg BID) | Velliparib Dose Days | MM-398 Dose (salt) (mg/$m^2$ q2w) |
|---|---|---|---|
| 1 | 100 | Day 5-12; 19-25 | 80, Day 1, 15 |
| 2 | 200 | Day 5-12; 19-25 | 80, Day 1, 15 |
| 3 | 200 | Day 5-12; 17-25 | 80, Day 1, 15 |
| 4 | 300 | Day 5-12; 19-25 | 80, Day 1, 15 |
| 5 | 400 | Day 5-12; 19-25 | 80, Day 1, 15 |

[1]Additional dose levels and alternate dosing schedules may be explored upon agreement of Sponsor, Medical Monitor and Investigators.
** After the MTD is reached, and for the first cycle only, we plan to enroll approximately 18 patients obtain tumor biopsies according to the schema outlined in the correlates section below.

The study will enroll 3 patients per dose cohort following a traditional 3+3 dose escalation design. Dose limiting toxicities (DLTs) will be evaluated during the first cycle of treatment (28 days) in order to determine the MTD. If there are no DLTs within the safety evaluation period, then the next cohort can be initiated following agreement between the Investigators and Medical Monitor. If a DLT occurs, then the cohort will be expanded to 6 patients. If 2 or more patients have DLTs within a given dose level, then the dose will not be escalated further; however, lower doses may be explored. Additional dosing schedules may also be explored depending on the safety, tolerability, and PK observed.

Given that these individual therapies have been studied in previous clinical trials, it is important that the safety assessment takes into account the expected safety profile of the standard dose regimens. For all treatment regimens, any toxicity that is related to disease progression will not be considered a DLT. The following events, occurring during cycle 1 of the study combination, will be considered DLTs if deemed drug-related:

- grade 3 or 4 neutropenia complicated by fever≥38.5° C. (i.e. febrile neutropenia) and/or documented infection;
- grade 4 neutropenia that does not resolve within 7 days despite optimal therapy (withholding study drug and GCSF administration);
- grade 4 thrombocytopenia that does not resolve within 7 days or any grade 3-4 thrombocytopenia complicated with hemorrhage;
- grade 4 anemia that does not resolve within 7 days despite optimal therapy (withholding study drug and red blood cell transfusions);
- inability to begin subsequent treatment course within 14 days of the scheduled date, due to study drug toxicity;
- any grade 3-4 non-hematologic toxicity (except fatigue/asthenia<2 weeks in duration; vomiting or diarrhea lasting less than 72 hours whether treated with an optimal anti-emetic or anti-diarrheal regimen or not; or alkaline phosphatase changes).
- ≥grade 2 seizure Patients will be treated until disease progression as determined by RECIST v1.1 criteria evaluated by CT scan every 8 weeks from first dose of study drug. The inclusion and exclusion criteria for the clinical trial are summarized in the table 9 below.

TABLE 9

| Inclusion Criteria | Exclusion Criteria |
|---|---|
| Patients must have histologic or cytologic confirmation of cancer for which there is no known standard therapy capable of extending life expectancy. | Active CNS metastasis |
| ECOG Performance Status 0 or 1 | Clinically significant GI disorders, including history of small bowel obstruction unless the obstruction was a surgically treated remote episode |
| Tumor lesion(s) amenable to multiple pass percutaneous biopsies and patient willing to undergo required pre- and post-treatment biopsies | Prior irinotecan therapy; or topotecan therapy or bevacizumab therapy within 6 months of first dose of study treatment |
| Must have adequate: | Prior chemotherapy or biological therapy within 3 weeks, or within a time interval less than 5 half-lives of the agent, prior to first dose of study treatment |
| Bone marrow function | Prior radiotherapy within 4 weeks of first dose of study treatment |
| ANC > 1,500 cells/μl without the use of hematopoietic growth factors | Patients who have had radiation to the pelvis or other bone marrow-bearing sites will be considered on a case by case basis and may be excluded if the bone marrow reserve is not considered adequate (i.e. radiation to >25% of bone marrow) |
| Platelet count > 100,000 cell/μl | Known hypersensitivity to MM-398 |
| Hemoglobin > 9 g/dL | Active infection |
| Hepatic function | Pregnant or breast feeding |
| Normal serum total bilirubin | |
| AST and ALT ≤2.5 × ULN (≤5 × ULN is acceptable if liver metastases are present) | |
| Renal function | |
| Serum creatinine ≤1.5 × ULN | |
| Normal ECG | |
| ≥18 years of age | |
| Able to understand and sign informed consent | |
| Prior PARP inhibitor therapy is allowed | |
| Willing to undergo pre-treatment ferumoxytol MRI (patients will be excluded from undergoing | |

TABLE 9-continued

| Inclusion Criteria | Exclusion Criteria |
|---|---|
| ferumoxytol MRI if they have evidence of iron overload, a known hypersensitivity to ferumoxytol or any other IV iron product, a documented history of multiple drug allergies, or those for whom MRI is otherwise contraindicated, including claustrophobia or anxiety related to undergoing MRI) | |

The dose escalation portion of the trial may require up to 30 patients if 6 patients are required at each of 5 dose levels. An additional 18 patients may be used to explore the effect of veliparib on the biologic correlates. Thus, the accrual ceiling will be set at 48 patients.

The study is proposed to include all solid tumor types, however, particular indications that are of high interest for this study includes the following: cervical cancer, ovarian cancer, triple negative breast cancer (TNBC), non-small cell lung cancer (NSCLC), small cell lung cancer (SCLC), gastric cancer, pancreatic cancer, and neuroendocrine tumors.

The methods and uses herein can also be applied to other tumor suitable types including those noted for increased frequency of DNA damage response (DDR) pathway deficiencies (or 'BRCAness') found in sporadic tumors, which are predicted to be sensitive to PARP inhibitors. As mentioned previously, BRCA1 or BRCA2 deficiencies, found particularly in triple negative breast cancer and high-grade serous ovarian cancer, sensitize cells to PARP-inhihitors. Likewise, loss of function of other genes and proteins involved in DDR pathways, including the endonuclease XPF-ERCC1, the homologous recombination repair proteins meiotic recombination protein 11 (MRE11) and Fanconi anemia pathway (FANC) proteins, also sensitize cells to PARP inhibitors. Fanconi anemia pathway deficiencies have been demonstrated in lung, cervical, and breast and ovarian cancers. These and other DDR pathway deficiencies may be predictive biomarkers for PARP inhibitor therapy, and will be explored retrospectively in this study. Veliparib, specifically, has also demonstrated clinical activity in a number of indications, including BRCA-positive and BRCA wild-type breast and ovarian cancer, as well as gastric cancer in combination with FOLFIRI. For the proposed study, indications were chosen not only for their high unmet medical need, but for potential sensitivity to irinotecan and/or veliparib based on the aforementioned pre-clinical and/or clinical experience. While the PARP inhibitor olaparib has recently been FDA approved as a monotherapy in BRCA+ ovarian cancer, this study will not limit treatment in the ovarian patient population to BRCA+ patients, as this is a phase I study of a combination therapy and may retrospectively identify patients with other DDR pathway deficiencies in addition to BRCA.

Use of Liposomal Irinotecan and Olaparib

MM-398 is administered by intravenous (IV) infusion over 90 minutes at a dose of 80 $mg/m^2$ (based on the corresponding amount of irinotecan hydrochloride trihydrate, equivalent to 70 $mg/m^2$ irinotecan free base) every two weeks. Olaparib is co-administered orally twice daily by the patient at home according to the following schedule (Table 10).

TABLE 10

| Dose Level[1] | Olaparib Dose (mg BID) | Oaparib Dose Days | MM-398 Dose ($mg/m^2$ q2w)* |
|---|---|---|---|
| 1 | 100 | Day 5-12; 19-25 | 80, Day 1, 15 |
| 2 | 200 | Day 5-12; 19-25 | 80, Day 1, 15 |
| 3 | 200 | Day 5-12; 17-25 | 80, Day 1, 15 |
| 4 | 300 | Day 5-12; 19-25 | 80, Day 1, 15 |
| 5 | 400 | Day 5-12; 19-25 | 80, Day 1, 15 |

*= The 80 $mg/m^2$ MM-398 dose is based on the corresponding amount of irinotecan hydrochloride trihydrate (equivalent to 70 $mg/m^2$ based on irinotecan free base).

Example 6

Measuring Phosphorylated H2AX in Tumor Biopsies

Figure 14:
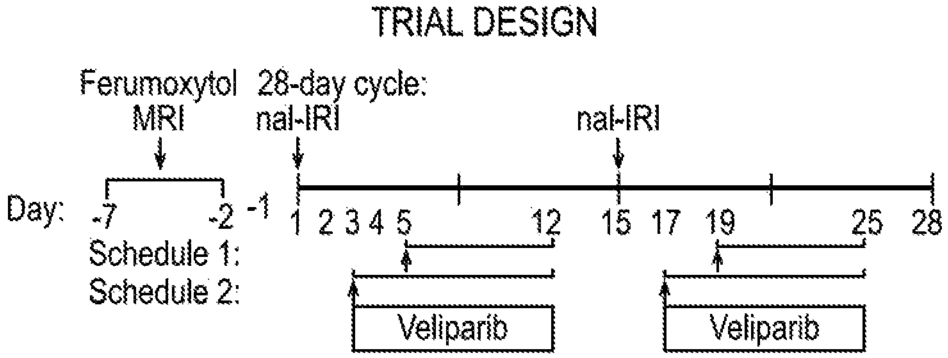
FIG. 14 is a graphical representation of a phase I study design employing the combinations of MM-398 (nal-IRI) and veliparib.

Phosphorylated H2AX (γ-H2AX) plays an important role in the recruitment and/or retention of DNA repair and checkpoint proteins such as BRCA1, MRE11/RAD50/NBS1 complex, MDC1 and 53BP1. DNA damage has been shown to increase H2AX phosphorylation in cancer cells following exposure to camptothecins. If the PARP inhibitor compound(s) is/are able to increase the degree of DNA damage due to irinotecan from MM-398, it may be detectable by measurement of H2AX phosphorylation. An immunofluorescence assay was used in previous clinical studies. Patient peripheral blood mononuclear cells (PBMCs), hair follicles, and/or tumor biopsy samples will be collected if there is readily accessible disease. The association between the pharmacodynamic response measured by γ-H2AX level can be assessed by Fisher's test or the Wilcoxon rank sum test, as appropriate; this evaluation will be done at the MTD+/−a maximum of 2 dose levels (FIG. 14).

TABLE 11

| Schedule for biopsies and surrogate samples | | | | | |
|---|---|---|---|---|---|
| Dose Level | | PARPi Dose (mg BID) | PARPi Dose Days | MM-398 Dose ($mg/m^2$ q2w) | Biopsy in am for PD marker |
| 1 | | 100 | Day 5-12; 19-25 | 80, Day 1, 15 | — |
| 2 | | 200 | Day 5-12; 19-25 | 80, Day 1, 15 | — |
| 3 | | 200 | Day 3-12; 17-25 | 80, Day 1, 15 | Days 1, 5, 19 |
| 4 | | 300 | Day 3-12; 17-25 | 80, Day 1, 15 | Days 1, 5, 19 |
| 5 | | 400 | Day 3-12; 17-25 | 80, Day 1, 15 | Days 1, 5, 19 |
| Confirm | A | MTD | Day 3-12; 19-25 | 80, Day 1, 15 | Days 1, 5, 19 |
| | B | MTD | Day 5-12; 17-25 | 80, Day 1, 15 | Days 1, 5, 19 |

Example 7

Figure 15A:
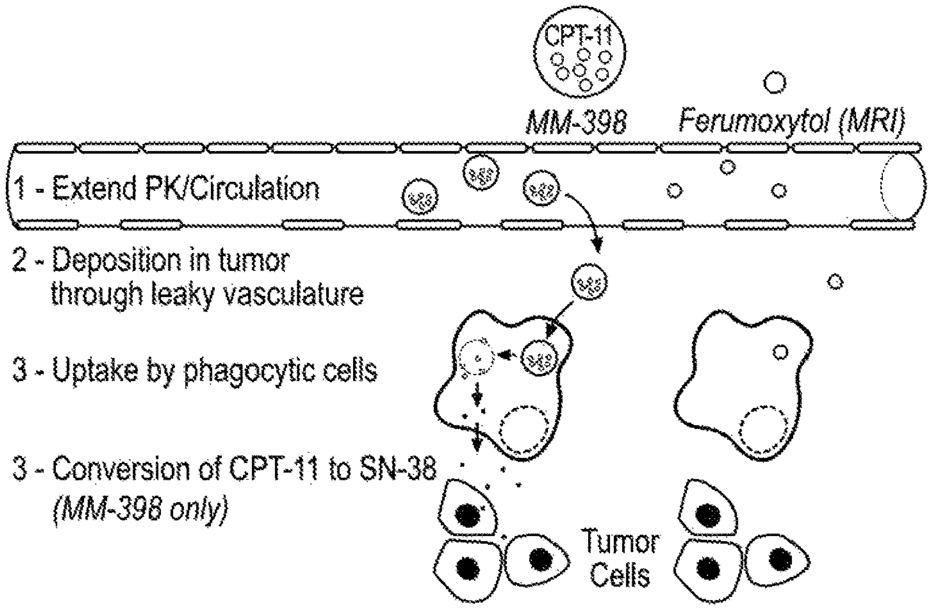
FIG. 15A is a schematic showing a use of ferumoxytol (FMX) as a predictive biomarker for cancer treatment with liposomal irinotecan (e.g., MM-398).
Figure 15B:
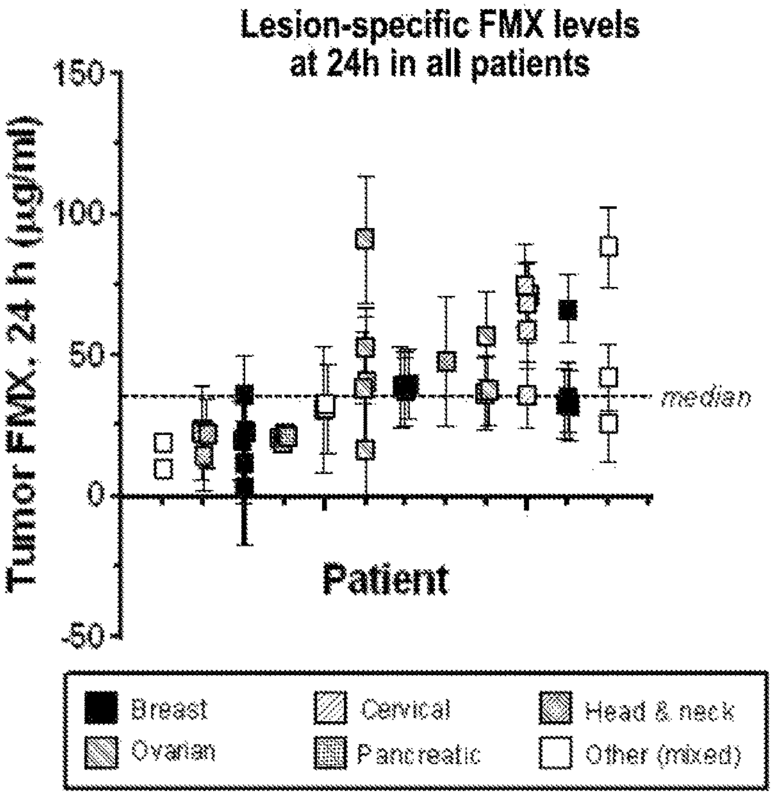
FIG. 15B is a graph showing FMX concentration of individual patient lesions was calculated using a standard curve from MR images obtained 24 h post-FMX injection.
Figure 15C:
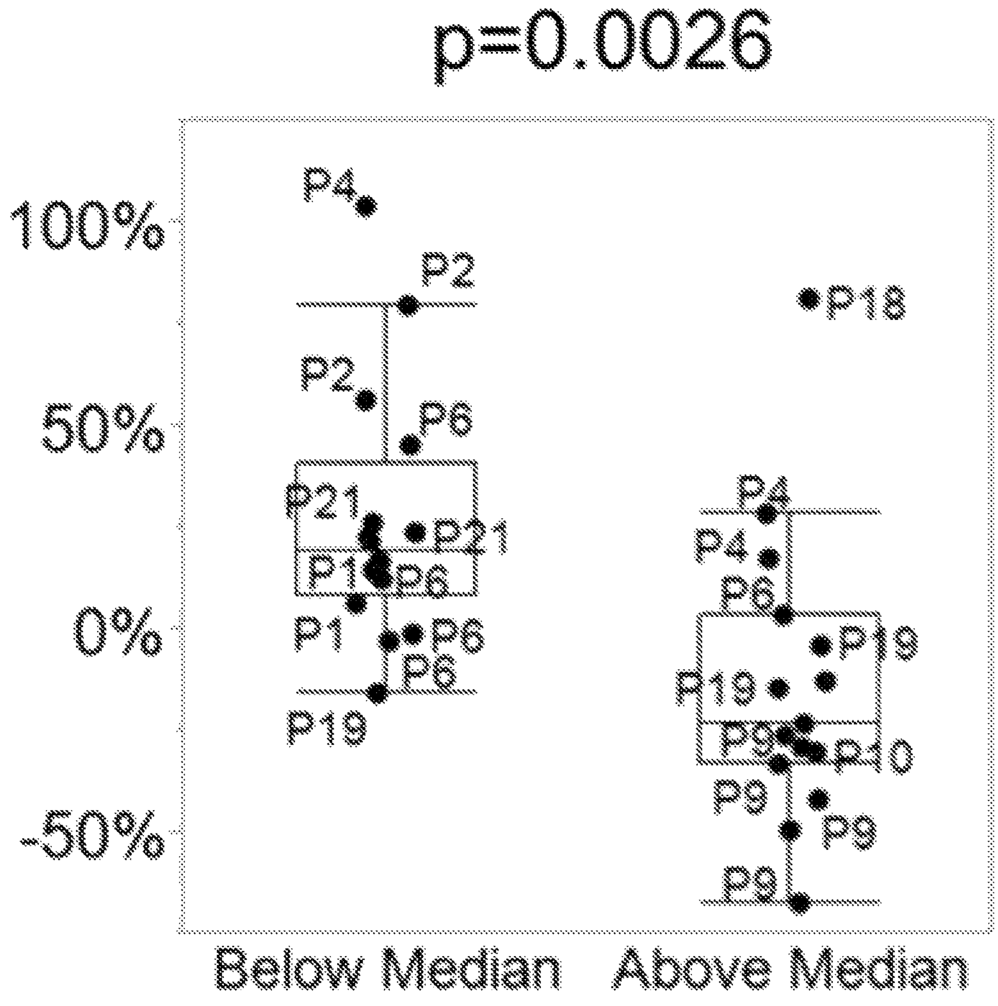
FIG. 15C is a graph showing FMX signal from lesions at 24 h are grouped relative to the median value observed in the FMX MRI evaluable lesions and compared to the best change in lesion size based on CT scans (data available from 9 patients; total of 31 lesions).

Administering and Detecting Ferumoxytol to Predict Deposition of Topoisomerase Inhibitor from Liposomal Irinotecan FIGS. 15A-15C show that FMX MRI may be a predictive tool for tumor response to MM-398. FIG. 15A is a schematic showing that MM-398 and FMX have similar properties, including 1) extended PK, 2) the ability to deposit in tumor tissues through the EPR effect (i.e. leaky vasculature), and 3) uptake by macrophages. Therefore, visualization of FMX on MRI may be able to predict MM-398 deposition. (B) FMX concentration of individual patient lesions was calculated using a standard curve from MR images obtained 24 h post-FMX injection. (C) FMX signal from lesions at 24 h are grouped relative to the median value observed in the FMX MRI evaluable lesions and compared to the best change in lesion size based on CT scans (data available from 9 patients; total of 31 lesions).

The phase 1 study of MM-398 also examined the feasibility of magnetic resonance (MR) imaging to predict tumor-associated macrophage (TAM) content and MM-398 deposition. TAMs appear to play a key role in the deposition, retention and activation of MM-398 within the tumor microenvironment. In this clinical study, ferumoxytol (FMX) a microparticulate preparation of a superparamagnetic iron oxide coated with polyglucose sorbitol carboxymethylether) was used as an imaging contrast agent and MR images were obtained at 1 h, 24 h, and 72 h following FMX injection. FMX is an approved therapy that is indicated for the treatment of iron deficiency anemia in adult patients with chronic kidney disease; however a growing number of cancer patients without iron deficiency are being administered FMX as an imaging agent to visualize macrophage content and vasculature. Like MM-398, FMX is also a nanoparticle with a diameter of approximately 17-31 nm. As tumor permeability was predicted to be an important factor in MM-398 efficacy, FMX was also investigated for use as a surrogate for liposome deposition (FIG. 15A). A benefit of FMX is that this agent helps to identity patients that are less likely to respond to MM-398 because of poor drug uptake. Ferumoxytol as a diagnostic test enables the detection of a patient population that would significantly benefit from MM-398 that would otherwise be uncategorized.

The MRI results from a human clinical trial study demonstrated that the amount of FMX depositing in tumor lesions was able to be quantified (FIG. 15B), and it was subsequently shown that a correlation existed between tumor lesion ferumoxytol uptake by MRI and response to MM-398 (FIG. 15C). This correlation is now being studied further in an expansion of the Phase 1 study, and is included as a correlative imaging study for a trial of MM-398+veliparib.

FMX is an iron replacement product indicated for the treatment of iron deficiency anemia in adult patients with chronic kidney disease. Although not approved as an indication, ferumoxytol has also been used as an imaging agent in cancer patients and will be utilized as such in this study. At least 2 days prior to Cycle 1 Day 1 (maximum of 8 days prior) a single dose of 5 mg/kg FMX will be administered by intravenous injection. The total single dose will not exceed 510 mg. the maximum approved single dose of FMX. This dosing schedule is less intense than the approved label, which recommends two doses of 510 mg 3 to 8 days apart; however since FMX is being used as imaging agent in this study as opposed to a replacement product for iron deficiency, a lower dose is more appropriate. Three MRIs will be performed for each patient over 2 days. All patients will have a baseline image acquired prior to the FMX infusion, and a second image acquired 1-4 h after the end of FMX administration. All patients will return the following day for a 24 h FMX-MRI using the same protocol and sequences as previously. Each patient will be required to complete their FMX-MRIs on the same scanner to reduce inter-scan variability. The body area to be scanned will be determined by the location of the patient's disease. Each MRI study will be evaluated for image quality and signal characteristics of tumors and reference tissue on T1-, T2- and T2*-weighted sequences. Once a completed set of images from each patient has been received, a qualitative review will be performed and sent to a quantitative lab for analysis. The data will be analyzed in a similar fashion as described above.

TABLE 12

| Imaging Correlates | | |
|---|---|---|
| Correlative Objective | Imaging Technique | Organ(s) Scanned and Timing of Scans |
| Ferumoxytol (FMX) uptake | MRI | Sites of disease; 3 scans completed approximately 2-6 days prior to Cycle 1 Day 1. Scan time points: baseline (immediately prior to FMX infusion) 1 h (post-FMX infusion) 24 h (post-FMX infusion) |
| Histone gamma-H2AX (Pommier, DTB-CCR; Doroshow, Leidos) | Immunofluorescence microscopy ELISA (in development) | Tumor biopsy before treatment, and during treatment. Hair follicles during treatment. PBMC before treatment and during treatment |

Imaging Correlate Study

Patients will be eligible to participate in the FMX imaging study if they do not meet any of the following criteria:

- Evidence of iron overload as determined by:
  - Fasting transferrin saturation of >45% and/or
  - Serum ferritin levels >1000 ng/ml
- A history of allergic reactions to any of the following:
  - compounds similar to ferumoxytol or any of its components as described in full prescribing information for ferumoxytol injection
  - any IV iron replacement product (e.g. parenteral iron, dextran, iron-dextran, or parenteral iron polysaccharide preparations)
  - multiple drugs
- Unable to undergo MRI or for whom MRI is otherwise contraindicated (e.g. presence of errant metal, cardiac pacemakers, pain pumps or other MRI incompatible devices; or history claustrophobia or anxiety related to undergoing MRI)

If a patient consents to FMX-MRI, the patient will receive ferumoxytol infusion and undergo the required FMX-MRI scans approximately 2-6 days prior to beginning MM-398 treatment (the FMX period). FMX will be administered at a dose of 5 mg/kg up to a maximum of 510 mg. All other aspects of administration will be consistent with the latest ferumoxytol prescribing information. A detailed FMX-MRI protocol will be included in the study imaging manual. Briefly, each patient will be required to complete their FMX-MRIs on the same scanner to reduce inter-scan variability. Each MRI study will be evaluated for image quality and signal characteristics of tumors and reference tissue on T1-, T2- and T2*-weighted sequences. Once a completed set of images from each patient has been received, the images will be loaded onto the viewing workstation for qualitative review and then sent to a quantitative lab (handled by central imaging CRO) for analysis.

Multiple MR images will be collected on Day 1-Day 2 of the FMX period at various time points: a baseline image acquired prior to the FMX infusion, a second image occurring 1-4 h after the end of FMX administration, and a third image at approximately 24 h post-FMX, using the same protocol and sequences as on Day 1. The body areas to be scanned will be determined by the location of the patient's disease; detailed instructions will be described in the study imaging manual.

Example 8

Clinical Use of Liposomal Irinotecan in Combination with 5-fluorouracil and Leucovorin Clinical efficacy of MM-398 has also been demonstrated in gemcitabine-refractory metastatic pancreatic cancer patients: in a randomized, Phase 3, international study (NAPOLI-1), MM-398 was given in combination with 5-fluorouracil/leucovorin (5-FU/LV) and significantly prolonged overall survival (OS) compared to 5-FU/LV treatment alone. The median OS for the MM-398-containing arm was 6.1 months compared to 4.2 months for the control arm (HR=0.67, p=0.0122). Because the active pharmaceutical ingredient in MM-398 is irinotecan, the safety profile was as anticipated, qualitatively similar to irinotecan, where the most common adverse events (≥30%) are nausea, vomiting, abdominal pain, diarrhea, constipation, anorexia, neutropenia, leukopenia (including lymphocytopenia), anemia, asthenia, fever, body weight decreasing, and alopecia (irinotecan package insert). Table 14 provides a summary of Grade 3 or higher safety data of patients treated with MM-398 plus 5-FU/LV from the NAPOLI-1 study. Table 13 provides toxicities observed in the Phase I monotherapy study, for comparison.

TABLE 13

Summary of the most common (>10%) grade 3 or greater adverse events from the 13 patients treated with MM-398 monotherapy at a dose of 80 $mg/m^2$ every 2 weeks during the phase I study.

Adverse Events ≥ Grade 3 in Study MM-398-01-01-02

| | n (%) |
|---|---|
| Diarrhea | 4 (30.8) |
| Hypokalemia | 3 (23.1) |
| Abdominal pain | 2 (15.4) |
| Anemia | 2 (15.4) |
| Nausea | 2 (15.4) |
| Neutropenia | 2 (15.4) |

TABLE 14

Summary of Grade 3 or higher AEs from the NAPOLI-1 phase III study.

| | MM-398 + 5-FU/LV[1] (N = 117) % | 5-FU/LV[2] (N = 134) % |
|---|---|---|
| GRADE ≥3 NON-HEMATOLOGIC AEs IN >5% PATIENTS, %[3] | | |
| Fatigue | 14 | 4 |
| Diarrhea | 13 | 3 |
| Vomiting | 11 | 3 |
| Nausea | 8 | 3 |
| Asthenia | 8 | 7 |
| Abdominal pain | 7 | 6 |
| Decreased appetite | 4 | 2 |
| Hypokalemia | 3 | 2 |
| Hypernatremia | 3 | 2 |

TABLE 14-continued

Summary of Grade 3 or higher AEs from the NAPOLI-1 phase III study.

| | MM-398 + 5-FU/LV[1] (N = 117) % | 5-FU/LV[2] (N = 134) % |
|---|---|---|
| GRADE ≥3 HEMATOLOGIC AES BASED ON LABORATORY VALUES, %[3, 4] | | |
| Neutrophil count decreased | 20 | 2 |
| Hemoglobin decreased | 6 | 5 |
| Platelet Count decreased | 2 | 0 |

[1]Dose: 80 mg/$m^2$ MM-398 + 2400 mg/$m^2$ over 46 h/400 mg/$m^2$ 5-FU/LV q2w
[2]Dose: 2000 mg/$m^2$ over 24 h/200 mg/$m^2$ 5-FU/LV weekly ×4, q6w
[3]Per CTCAE Version 4
[4]Includes only patients who had at least one post-baseline assessment

Example 9

Cell Survival for Various TNBC Cell Lines Following SN-38 and PARP Inhibitor Combination Treatment Tables 15a, 15b, 16a, and 16b provide the results of in vitro measurements of cell survival for various triple negative breast cancer (TNBC) cancer cell lines to determine the cell viability following treatment with SN-38 and/or a PARP inhibitor. Tables 15a and 15b provide IC50 data, and Tables 16a and 16b provide Maximum Kill data.

TABLE 15a

IC50 log10 (μM)

| | | Cell Line | | |
|---|---|---|---|---|
| Exp. 1 | Treatment | BT20 | SUM159PT | HCC38 |
| | SN38 | −0.18 | −2.35 | −2.80 |
| | Niraparib | 2.14 | 0.35 | 1.23 |
| | SN38 & Niraparib (3 ug/ml) | −0.67 | −3.99 | −0.12 |
| | SN38 & Niraparib (1 ug/ml) | −0.70 | −3.42 | −4.09 |
| | SN38 & Niraparib (0.3 ug/ml) | −0.71 | −2.85 | −4.23 |
| | SN38 & Niraparib (0.1 ug/ml) | −0.61 | −2.87 | −4.05 |
| Exp. 2 | Treatment | BT20 | SUM149PT | SUM159PT |
| | SN38 | −0.69 | 0.24 | −2.39 |
| | Olaparib | 1.24 | 2.40 | 0.18 |
| | SN38 & Olaparib (3 ug/ml) | −1.48 | −0.19 | −3.70 |
| | SN38 & Olaparib (1 ug/ml) | −1.49 | −0.34 | −3.31 |
| | SN38 & Olaparib (0.3 ug/ml) | −1.44 | −0.18 | −2.92 |
| | SN38 & Olaparib (0.1 ug/ml) | −1.29 | −0.11 | −2.92 |
| Exp. 3 | Treatment | BT20 | SUM149PT | SUM159PT |
| | SN38 | −0.37 | 0.27 | −2.66 |
| | Rucaparib | 1.27 | 1.68 | −0.07 |
| | SN38 & Rucaparib (3 ug/ml) | −1.33 | −0.16 | −3.64 |
| | SN38 & Rucaparib (1 ug/ml) | −1.47 | −0.23 | −3.28 |
| | SN38 & Racaparib (0.3 ug/ml) | −1.48 | −0.49 | −3.23 |
| | SN38 & Racaparib (0.1 ug/ml) | −1.24 | −0.10 | −3.11 |

TABLE 15a-continued

IC50 log10 (μM)

| | | Cell Line | | |
|---|---|---|---|---|
| Exp. 4 | Treatment | BT20 | SUM159PT | HCC38 |
| | SN38 | −0.24 | −2.33 | −2.75 |
| | Talazoparib | 1.45 | −1.03 | −1.23 |
| | SN38 & Talazoparib (3 ug/ml) | −1.88 | −4.01 | −3.41 |
| | SN38 & Talazoparib (1 ug/ml) | −1.70 | −4.01 | −4.01 |
| | SN38 & Talazoparib (0.3 ug/ml) | −1.10 | −4.01 | −5.46 |
| | SN38 & Talazoparib (0.1 ug/ml) | −1.36 | −4.01 | −2.87 |

TABLE 15b

IC50 log10 (μM)

| | | Cell Line | | |
|---|---|---|---|---|
| Exp. 1 | Treatment | HCC1187 | HCC1806 | BT549 |
| | SN38 | −0.68 | −2.08 | −0.10 |
| | Niraparib | 2.11 | 1.27 | 2.03 |
| | SN38 & Niraparib (3 ug/ml) | −1.58 | −2.80 | −0.39 |
| | SN38 & Niraparib (1 ug/ml) | −1.45 | −2.62 | −0.64 |
| | SN38 & Niraparib (0.3 ug/ml) | −1.61 | −2.55 | −0.74 |
| | SN38 & Niraparib (0.1 ug/ml) | −1.41 | −2.52 | −0.55 |
| Exp. 2 | Treatment | HCC70 | HCC1187 | BT549 |
| | SN38 | −0.07 | −0.64 | −0.04 |
| | Olaparib | $-4.2 \times 10^7$ | 2.41 | 2.04 |
| | SN38 & Olaparib (3 ug/ml) | −0.58 | −1.77 | −0.55 |
| | SN38 & Olaparib (1 ug/ml) | −0.49 | −1.67 | −0.48 |
| | SN38 & Olaparib (0.3 ug/ml) | −0.50 | −1.35 | −0.35 |
| | SN38 & Olaparib (0.1 ug/ml) | −0.48 | −1.56 | −0.04 |
| Exp. 3 | Treatment | HCC38 | HCC1954 | BT549 |
| | SN38 | −2.89 | −0.97 | −0.05 |
| | Rucaparib | −0.07 | 1.60 | 1.75 |
| | SN38 & Rucaparib (3 ug/ml) | 4.93 | −1.22 | −0.48 |
| | SN38 & Rucaparib (1 ug/ml) | −3.88 | −1.33 | −0.57 |
| | SN38 & Rucaparib (0.3 ug/ml) | −4.01 | −1.51 | −0.49 |
| | SN38 & Rucaparib (0.1 ug/ml) | −3.29 | −1.57 | −0.52 |
| Exp. 4 | Treatment | HCC1187 | HCC1954 | SKBR3 |
| | SN38 | −0.98 | −0.65 | −1.38 |
| | Talazoparib | 2.28 | 3.64 | $-2.8 \times 10^4$ |
| | SN38 & Talazoparib (3 ug/ml) | −1.79 | −1.64 | −2.05 |
| | SN38 & Talazoparib (1 ug/ml) | −1.79 | −1.51 | −2.65 |
| | SN38 & Talazoparib (0.3 ug/ml) | −1.94 | −1.45 | −2.23 |
| | SN38 & Talazoparib (0.1 ug/ml) | −1.92 | −1.29 | −2.41 |

TABLE 16a

Maximum Kill Percent

| Exp. 1 | Treatment | BT20 | SUM159PT | HCC38 |
|---|---|---|---|---|
| | | Cell Line | | |
| | SN38 | 100 | 97 | 96 |
| | Niraparib | 100 | 97 | 100 |
| | SN38 & Niraptib (3 ug/ml) | 100 | 100 | |
| | SN38 & Niraparib (1 ug/ml) | 100 | 100 | 93 |
| | SN38 & Niraparib (0.3 ug/ml) | 100 | 99 | 100 |
| | SN38 & Niraparib (0.1 ug/ml) | 100 | 100 | 100 |

| Exp. 2 | Treatment | BT20 | SUM149PT | SUM159PT |
|---|---|---|---|---|
| | | Cell Line | | |
| | SN38 | 100 | 96 | 97 |
| | Olaparib | 98 | 100 | 94 |
| | SN38 & Olaparib (3 ug/ml) | 98 | 97 | 100 |
| | SN38 & Olaparib (1 ug/ml) | 99 | 96 | 97 |
| | SN38 & Olaparib (0.3 ug/ml) | 100 | 98 | 99 |
| | SN38 & Olaparib (0.1 ug/ml) | 100 | 96 | 99 |

| Exp. 3 | Treatment | BT20 | SUM149PT | SUM159PT |
|---|---|---|---|---|
| | | Cell Line | | |
| | SN38 | 100 | 95 | 99 |
| | Rucaparib | 100 | 99 | 97 |
| | SN38 & Rucaparib (3 ug/ml) | 92 | 97 | 99 |
| | SN38 & Rucaparib (1 ug/ml) | 100 | 97 | 99 |
| | SN38 & Rucaparib (0.3 ug/ml) | 94 | 95 | 100 |
| | SN38 & Rucaparib (0.1 ug/ml) | 96 | 100 | 97 |

| Exp. 4 | Treatment | BT20 | SUM159PT | HCC38 |
|---|---|---|---|---|
| | | Cell Line | | |
| | SN38 | 100 | 96 | 92 |
| | Talazoparib | 100 | 94 | 92 |
| | SN38 & Talazoparib (3 ug/ml) | 100 | | |
| | SN38 & Talazoparib (1 ug/ml) | 90 | | |
| | SN38 & Talazoparib (0.3 ug/ml) | 93 | | |
| | SN38 & Talazoparib (0.1 ug/ml) | 93 | | |

TABLE 16b

Maximum Kill Percent

| Exp. 1 | Treatment | HCC1187 | HCC1806 | BT549 |
|---|---|---|---|---|
| | | Cell Line | | |
| | SN38 | 90 | 93 | 95 |
| | Niraparib | 98 | 100 | 100 |
| | SN38 & Niraparib (3 ug/ml) | 89 | 91 | 94 |
| | SN38 & Niraparib (1 ug/ml) | 93 | 92 | 92 |
| | SN38 & Niraparib (0.3 ug/ml) | 89 | 92 | 92 |
| | SN38 & Niraparib (0.1 ug/ml) | 89 | 93 | 94 |

| Exp. 2 | Treatment | HCC70 | HCC1187 | BT549 |
|---|---|---|---|---|
| | | Cell Line | | |
| | SN38 | 97 | 100 | 93 |
| | Olaparib | 50 | 87 | 100 |
| | SN38 & Olaparib (3 ug/ml) | 98 | 100 | |
| | SN38 & Olaparib (1 ug/ml) | 100 | 91 | 96 |
| | SN38 & Olaparib (0.3 ug/ml) | 100 | 99 | 94 |
| | SN38 & Olaparib (0.1 ug/ml) | 100 | 99 | 96 |

TABLE 16b-continued

Maximum Kill Percent

| Exp. 3 | Treatment | HCC38 | HCC1954 | BT549 |
|---|---|---|---|---|
| | | Cell Line | | |
| | SN38 | 92 | 94 | 94 |
| | Rucaparib | 87 | 100 | 100 |
| | SN38 & Rucaparib (3 ug/ml) | | 96 | 93 |
| | SN38 & Rucaparib (1 ug/ml) | 98 | 94 | 92 |
| | SN38 & Rucaparib (0.3 ug/ml) | 98 | 95 | 93 |
| | SN38 & Rucaparib (0.1 ug/ml) | 97 | 93 | 94 |

| Exp. 4 | Treatment | HCC1187 | HCC1954 | SKBR3 |
|---|---|---|---|---|
| | | Cell Line | | |
| | SN38 | 88 | 100 | 88 |
| | Talazoparib | | 100 | |
| | SN38 & Talazoparib (3 ug/ml) | 89 | 93 | 90 |
| | SN38 & Talazoparib (1 ug/ml) | 89 | 94 | 89 |
| | SN38 & Talazoparib (0.3 ug/ml) | 89 | 94 | 100 |
| | SN38 & Talazoparib (0.1 ug/ml) | 100 | 96 | 87 |

Figure 3A:
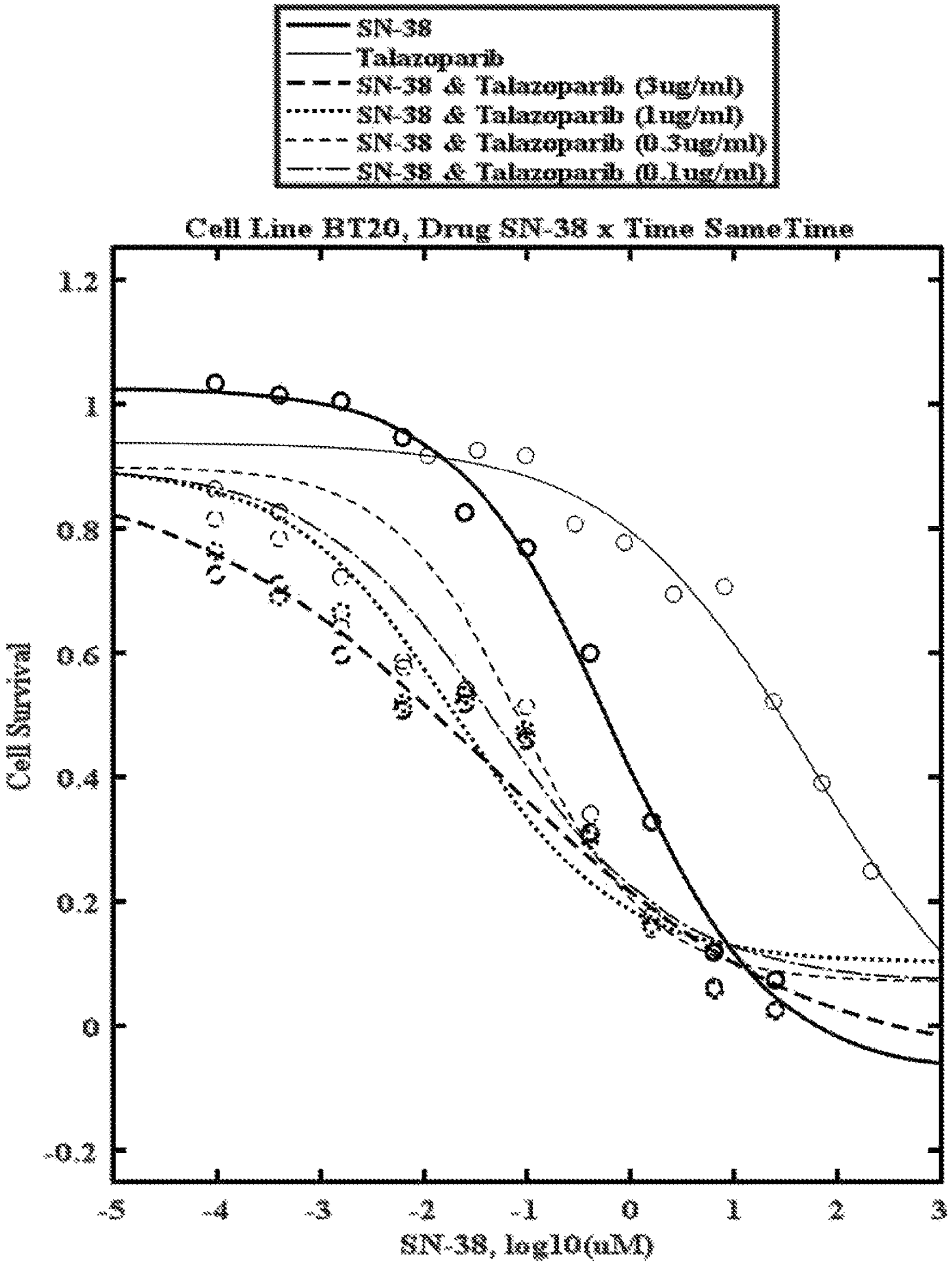
FIG. 3A is a graph showing the results of in vitro measurement of cell survival for BT-20 triple negative breast cancer (TNBC) cancer cells treated with the topoisomerase inhibitor SN-38 and the PARP inhibitor talazoparib.
Figure 3B:
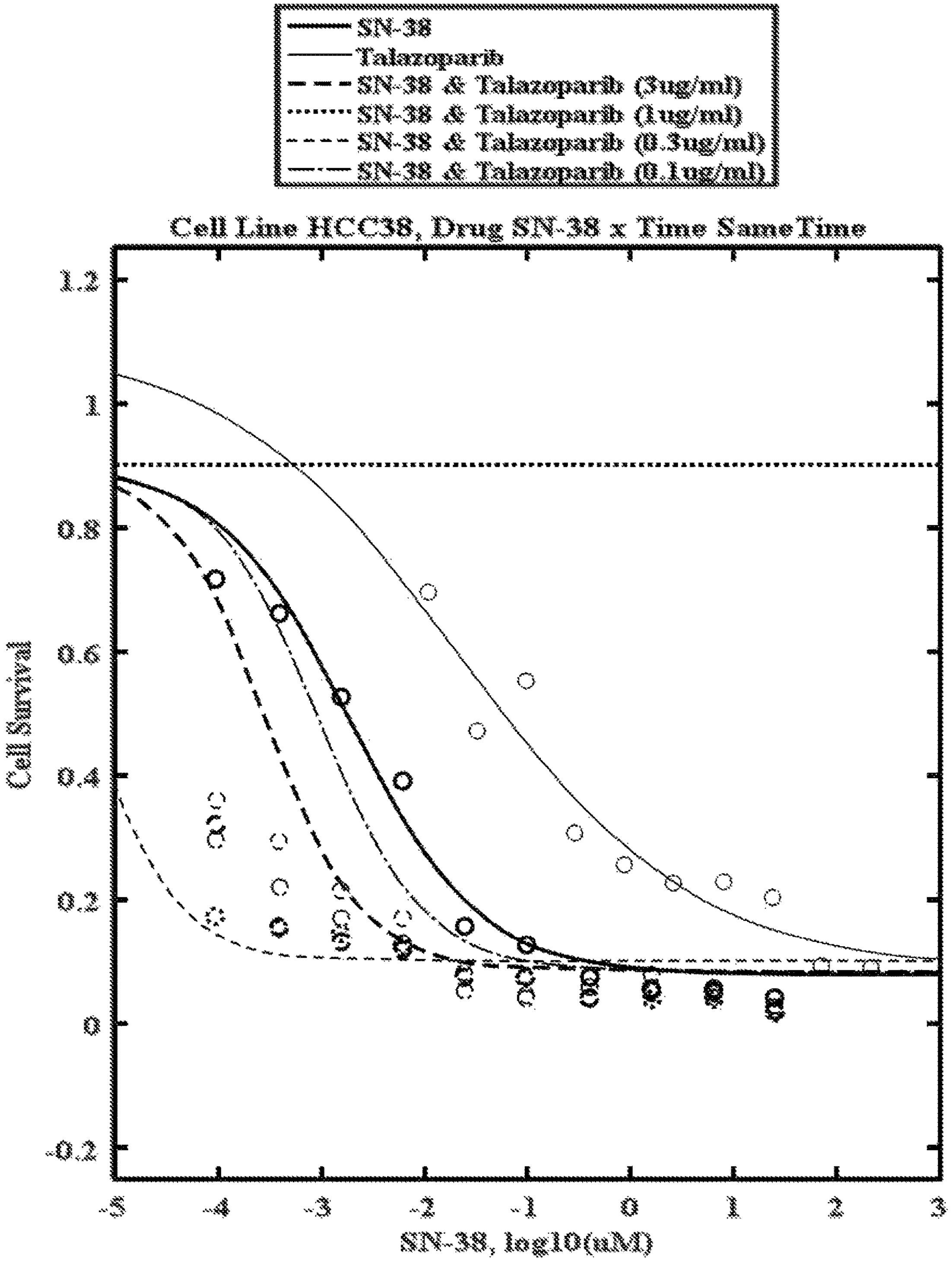
FIG. 3B is a graph showing the results of in vitro measurement of cell survival for HCC38 triple negative breast cancer (TNBC) cancer cells treated with the topoisomerase inhibitor SN-38 and the PARP inhibitor talazoparib.

The experiments that generated these data were performed in 384 well format. Cells were plated at 1000 cells/well and then incubated for 24 hours. Then SN-38 and/or one of four different PARP inhibitors (talazoparib niraparib, olaparib or rucaparib) was added and intubated for an additional 24 hours then the wells were washed with PBS to remove the drug and fresh media was added back into the wells. The plates were then allowed to incubate for 72 hours period. After the 72 hour incubation period the media was removed and cell viability was determined using the Cell-Titer-Glo® cell viability assay (Promega, Madison Wis.) according to the product instructions. FIGS. 3A and 3B are line graphs that depict cell viability in BT20 and HCC38 breast cancer cell lines, respectively, following treatment with SN-38 and/or talazoparib.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein. The disclosure of each and every U.S., international or other patent or patent application or publication referred to herein is hereby incorporated herein by reference in its entirety.

The invention claimed is:

1. A method of treating a patient having a solid tumor, the method comprising i) administering to the patient liposomal irinotecan once every two weeks; and ii) administering a Poly(ADP-ribose) Polymerase (PARP) inhibitor daily for 3 to 10 days between consecutive administrations of the liposomal irinotecan wherein the PARP inhibitor starting at least 2 days after the liposomal irinotecan and ending at least 1 day prior to the administration of additional liposomal irinotecan, wherein the patient has been diagnosed with ovarian cancer.

2. The method according to claim 1, wherein each administration of liposomal irinotecan is administered as a dose of 70 $mg/m^2$ (free base).

3. The method of claim 2, wherein the patient does not have a BRCA1 or a BRCA2 mutation and wherein the PARP inhibitor is selected from the group consisting of niraparib, olaparib, veliparib, rucaparib and talazoparib.

4. The method according to claim 2, wherein the PARP inhibitor is administered on each of consecutive days 5 to 10.

5. The method of claim 4, wherein the patient does not have a BRCA1 or a BRCA2 mutation and wherein the PARP inhibitor is selected from the group consisting of niraparib, olaparib, veliparib, rucaparib and talazoparib.

6. A method of treating a patient with cancer and having a tumor, the method comprising i) administering to the patient an effective amount of liposomal irinotecan, wherein the liposomal irinotecan is a unilamellar lipid bilayer vesicle, which encapsulates irinotecan sucrosofate salt and the vesicle is composed of 1,2-distearoyl-sn-glycero-3-phosphochline, cholesterol, and methoxy-terminated polyethylene glycol(MW 2000)-distearoylphosphatidylethanolamine, at a weight ratio of 6.81 mg:2.22 mg:0.12 mg; and ii) administering to the patient an effective amount of a PARP inhibitor selected from the group consisting of niraparib, olaparib, veliparib, rucaparib and talazoparib, wherein the PARP inhibitor is administered after an effective irinotecan plasma clearing interval, wherein the patient has been diagnosed with ovarian cancer.

7. The method of claim 6, wherein the effective irinotecan plasma clearing interval is from about 48 to about 120 hours.

8. The method of claim 7, wherein the effective irinotecan plasma clearing interval is 2, 3, 4 or 5 days.

9. The method of claim 8, wherein the patient does not have a BRCA1 or a BRCA2 mutation.

10. The method of claim 9, wherein the effective amount of MM-398 liposomal irinotecan is 70 $mg/m^2$ (free base) administered during a 90 minute infusion.

11. The method of claim 10, wherein each administration of the PARP inhibitor is administered at a dose of from about 20 mg/day to about 800 mg/day.

12. A method of treating a patient diagnosed with ovarian cancer and having a solid tumor, the method comprising administering to the patient an antineoplastic therapy in a 28-day treatment cycle, the antineoplastic therapy consisting of:

i) intravenously administering to the patient an effective amount of a liposomal irinotecan only on days 1 and 15 of the treatment cycle, the liposomal irinotecan having an irinotecan terminal elimination half-life of about 26.8 hours and a maximal irinotecan plasma concentration of about 38.0 micrograms/ml; and ii) administering an effective amount of a PARP inhibitor to the patient on days 5-12 and 19-25 or 3-12 and 17-25 of the treatment cycle.

13. The method of claim 12, wherein the PARP inhibitor is selected from the group consisting of niraparib, olaparib, veliparib, rucaparib and talazoparib.

14. The method of claim 13, wherein the therapeutically effective amount of the liposomal irinotecan is 70 $mg/m^2$ (free base) administered during a 90 minute infusion.

15. The method of claim 14, further comprising administering one or more subsequent 28-day treatment cycles of the antineoplastic therapy to the patient in the absence of disease progression or unacceptable toxicity during the prior treatment cycle of the antineoplastic therapy.

16. The method of claim 15, wherein the patient does not have a BRCA1 or a BRCA2 mutation.

17. The method of claim 16, wherein each administration of the PARP inhibitor is administered at a dose of from about 20 mg/day to about 800 mg/day.

* * * * *

UNITED STATES PATENT AND TRADEMARK OFFICE

CERTIFICATE OF CORRECTION

PATENT NO. : 10,478,428 B2
APPLICATION NO. : 15/852551
DATED : November 19, 2019
INVENTOR(S) : Sarah F. Blanchette et al.

It is certified that error appears in the above-identified patent and that said Letters Patent is hereby corrected as shown below:

In the Claims

Column 34, Claim 1, Line 58, “PARP inhibitor starting at least 2 days” should read --PARP inhibitor is administered starting at least 2 days--.

Signed and Sealed this
Seventeenth Day of March, 2020

Andrei Iancu
*Director of the United States Patent and Trademark Office*